(12) United States Patent
Zhou et al.

(10) Patent No.: US 11,208,407 B2
(45) Date of Patent: Dec. 28, 2021

(54) SUBSTITUTED PHENYL COMPOUNDS AS INDOLEAMINE 2,3-DIOXYGENASE (IDO) INHIBITORS

(71) Applicant: Merck Sharp & Dohme Corp., Rahway, NJ (US)

(72) Inventors: Hua Zhou, Acton, MA (US); Abdelghani Achab, Melrose, MA (US); Xavier Fradera, Brookline, MA (US); Yongxin Han, Needham, MA (US); Derun Li, Brighton, MA (US); Meredeth A. McGowan, Boston, MA (US); Nunzio Sciammetta, Sudbury, MA (US); David L. Sloman, Brookline, MA (US); Wensheng Yu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/631,191

(22) PCT Filed: Jul. 30, 2018

(86) PCT No.: PCT/US2018/044273
§ 371 (c)(1),
(2) Date: Jan. 15, 2020

(87) PCT Pub. No.: WO2019/027855
PCT Pub. Date: Feb. 7, 2019

(65) Prior Publication Data
US 2020/0216443 A1     Jul. 9, 2020

Related U.S. Application Data

(60) Provisional application No. 62/540,314, filed on Aug. 2, 2017.

(51) Int. Cl.
*C07D 471/04*       (2006.01)
*C07D 235/14*       (2006.01)

(52) U.S. Cl.
CPC ......... *C07D 471/04* (2013.01); *C07D 235/14* (2013.01)

(58) Field of Classification Search
CPC .. A61K 31/4439; A61K 45/06; C07D 401/08; C07D 401/14; C07D 471/04
USPC ...................................................... 514/303
See application file for complete search history.

(56) References Cited

U.S. PATENT DOCUMENTS

| | | | |
|---|---|---|---|
| 8,580,829 B2 | 11/2013 | Bartolozzi et al. | |
| 9,174,980 B2 | 11/2015 | Bartolozzi et al. | |
| 2010/0022543 A1* | 1/2010 | Melvin, Jr. | C07D 277/24 514/236.8 |
| 2013/0225615 A1* | 8/2013 | Hadd | C07D 403/12 514/266.23 |
| 2016/0333009 A1 | 11/2016 | Bartlett et al. | |
| 2016/0376270 A1 | 12/2016 | Bates et al. | |
| 2018/0186787 A1* | 7/2018 | Cowley | C07D 471/04 |
| 2018/0258075 A1* | 9/2018 | Cowley | A61P 9/00 |
| 2018/0362482 A1* | 12/2018 | Han | A61P 31/14 |
| 2019/0144433 A1* | 5/2019 | Han | A61K 45/06 514/252.01 |
| 2020/0024236 A1* | 1/2020 | Lewis | A61K 31/423 |
| 2020/0095212 A1* | 3/2020 | Liu | A61P 27/00 |
| 2020/0102278 A1* | 4/2020 | Guo | A61P 25/28 |
| 2020/0215042 A1* | 7/2020 | Zhou | C07D 401/14 |
| 2020/0216425 A1* | 7/2020 | Han | A61K 31/4418 |
| 2020/0239423 A1* | 7/2020 | White | C07D 305/08 |
| 2020/0277252 A1* | 9/2020 | McGowan | C07D 285/06 |
| 2020/0290996 A1* | 9/2020 | White | C07D 213/85 |

FOREIGN PATENT DOCUMENTS

| | | | | |
|---|---|---|---|---|
| WO | WO-2012020725 A1 * | 2/2012 | ........... | C07D 413/04 |
| WO | WO-2017139414 A1 * | 8/2017 | ........... | C07D 257/04 |
| WO | WO-2018011747 A1 * | 1/2018 | ........... | C07D 413/04 |
| WO | WO-2018039512 A1 * | 3/2018 | ........... | C07D 471/04 |

(Continued)

OTHER PUBLICATIONS

Brochez; European Journal of Cancer 2017, 76, 167-182. doi: 10.1016/j.ejca.2017.01.011 (Year: 2017).*

(Continued)

*Primary Examiner* — Daniel R Carcanague

(74) *Attorney, Agent, or Firm* — Yong Zhao; Catherine D. Fitch

(57) ABSTRACT

Disclosed herein is a compound of formula (I), or a pharmaceutically acceptable salt thereof: (I) Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

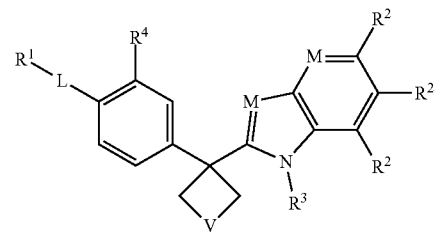

16 Claims, No Drawings

(56) References Cited

FOREIGN PATENT DOCUMENTS

| WO | WO-2019027856 A1 | * | 2/2019 | ........... C07D 401/08 |
| WO | WO-2019101188 A1 | * | 5/2019 | ......... C07D 491/056 |
| WO | WO-2019111107 A1 | * | 6/2019 | .............. A61P 31/14 |
| WO | WO-2019141153 A1 | * | 7/2019 | ......... A61K 31/4709 |
| WO | WO-2020251871 A2 | * | 12/2020 | ........... C07D 471/04 |

OTHER PUBLICATIONS

Prendergast; Cancer Res 2017, 77, 6795-6811. doi: 10.1158/0008-5472.CAN-17-2285 (Year: 2017).*
Pubchem, Compound Summary for CID 122186635, Create Date Oct. 26, 1926.
European Search Report for PCTUS2018044273, dated Feb. 3, 3021, 6 pages.

* cited by examiner

SUBSTITUTED PHENYL COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2018/044273, filed Jul. 30, 2018, which claims the benefit of U.S. Provisional Application No. 62/540,314, filed Aug. 2, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt thereof:

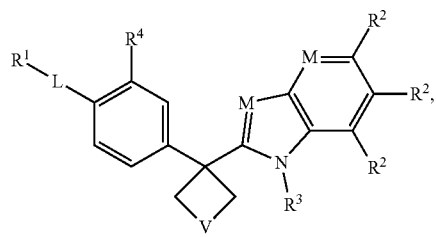

(I)

wherein:
L is selected from (1) a bond, (2) —NHC(O)—, (3) —C(O)NH—, (4) —NH— and (5) —NHC(O)O—; each occurrence of M is independently selected from (1) —$CR^a$═ and (2) —N═; wherein each $R^a$ is independently selected from (a) H, (b) halogen and (c) $C_{1-6}$ alkyl;
V is selected from (1) —$CR^bR^b$, (2) —$NR^c$— and (3) —O—; wherein each occurrence of $R^b$ is independently selected from (a) H, (b) —OH, (c) halogen and (d) $C_{1-6}$ alkyl; and $R^c$ is selected from (a) H and (b) $C_{1-6}$ alkyl;
$R^1$ is selected from (1) $C_{1-6}$ alkyl, (2) $C_{3-6}$ cycloalkyl, (3) aryl and (4) 5- or 6-membered heteroaryl; wherein:
the $C_{1-6}$ alkyl of (1) is optionally substituted with —$NH_2$; and
each of the aryl of (3) and the heteroaryl of (4) is optionally substituted with 1 to 3 substituents independently selected from: (a) halogen, (b) —CN, (c) —$NH_2$, (d) $C_{1-6}$ alkyl optionally substituted with 1 to 3 substituents independently selected from halogen, —OH, —$NH_2$ and $C_{3-6}$ cycloalkyl, (e) —O—$C_{1-6}$ alkyl optionally substituted with 1 to 3 halogens and (f) $C_{3-6}$ cycloalkyl; each occurrence of $R^2$ is independently selected from (1) H, (2) —OH, (3) halogen, (4) —CN and (5) $C_{1-6}$ alkyl; wherein the $C_{1-6}$ alkyl of (5) is optionally substituted with 1 to 3 substituents independently selected from (a) —OH and (b) halogen;
$R^3$ is selected from (1) H and (2) $C_{1-6}$ alkyl optionally substituted with (a) halogen or (b) —OH; and
$R^4$ is selected from (1) H, (2) halogen, (3) —CN, (4) $C_{2-6}$ alkenyl and (5) $C_{1-6}$ alkyl optionally substituted with —OH.
In one embodiment of the compound of formula (I), or a pharmaceutically acceptable salt thereof:
L is selected from (1) a bond, (2) —NHC(O)— and (3) —C(O)NH—;
each occurrence of M is independently selected from (1) —$CR^a$═ and (2) —N═; wherein each occurrence of $R^a$ is independently selected from (a) H, (b) halogen and (c) $C_{1-6}$ alkyl;
V is selected from (1) —$CR^bR^b$—, (2) —$NR^c$— and (3) —O—; wherein each occurrence of $R^b$ is independently selected from (a) H, (b) —OH, (c) halogen and (d) $C_{1-6}$ alkyl; and $R^c$ is selected from (a) H and (b) $C_{1-6}$ alkyl;
$R^1$ is selected from (1) $C_{1-6}$ alkyl, (2) $C_{3-6}$ cycloalkyl, (3) aryl and (4) 5- or 6-membered heteroaryl; wherein the $C_{1-6}$ alkyl is optionally substituted with —$NH_2$; and the aryl and heteroaryl is optionally substituted with 1 to 3 substituents independently selected from (a) halogen, (b) —CN, (c) —$CF_3$, (d) —$NH_2$, (e) $C_{1-6}$ alkyl and (f) $C_{3-6}$ cycloalkyl;
each occurrence of $R^2$ is independently selected from (1) H, (2) —OH, (3) halogen, (4) —CN and (5) $C_{1-6}$ alkyl; wherein the $C_{1-6}$ alkyl is optionally substituted with 1 to 3 substituents independently selected from (a) —OH and (b) halogen; and
$R^3$ is selected from (1) H and (2) $C_{1-6}$ alkyl optionally substituted with halogen or —OH.
In one embodiment of the compound of formula (I), or a pharmaceutically acceptable salt thereof:
L is selected from (1) —NHC(O)— and (2) —C(O)NH—;
each occurrence of M is independently selected from (1) —$CR^a$═ and (2) —N═; wherein $R^a$ is selected from (a) H, (b) halogen and (c) $C_{1-6}$ alkyl;
V is selected from (1) —$CR^bR^b$— and (2) —$NR^c$—; wherein each occurrence of $R^b$ is independently selected from (a) H, (b) —OH, (c) halogen and (d) $C_{1-6}$ alkyl; and R is selected from (a) H and (b) $C_{1-6}$ alkyl;
$R^1$ is selected from (1) $C_{1-6}$ alkyl, (2) $C_{3-6}$ cycloalkyl, (3) aryl and (4) 5- or 6-membered heteroaryl; wherein the aryl and heteroaryl is optionally substituted with 1 to 3 substituents independently selected from (a) halogen, (b) —CN, (c) —CF$_3$, (d) —NH$_2$, (e) C$_{1-6}$ alkyl and (f) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^3$ is selected from (1) H and (2) C$_{1-6}$ alkyl.
In one embodiment of the compound of formula (I), or a pharmaceutically acceptable salt thereof:
each M is —N═;
V is —CR$^b$R$^b$—; wherein each occurrence of R$^b$ is independently selected from (a) H, (b) —OH, (c) halogen and (d) C$_{1-6}$ alkyl;
R$^1$ is selected from (1) C$_{1-6}$ alkyl, (2) C$_{3-6}$ cycloalkyl, (3) aryl and (4) 5- or 6-membered heteroaryl; wherein the aryl and heteroaryl is optionally substituted with 1 to 3 substituents independently selected from (a) halogen, (b) —CN, (c) —CF$_3$, (d) —NH$_2$, (e) C$_{1-6}$ alkyl and (f) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^3$ is H.
In one embodiment of the compound of formula (I), or a pharmaceutically acceptable salt thereof:
L is selected from (1) a bond, (2) —NHC(O)— and (3) —C(O)NH—;
each occurrence of M is independently selected from (1) —CR$^a$═ and (2) —N═; wherein R$^a$ is selected from (a) H, (b) halogen and (c) methyl;
V is selected from (1) —CR$^b$R$^b$— and (2) —O—; wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—C$_{1-6}$ alkyl optionally substituted with 1 to 3 halogens and (g) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens;
R$^3$ is selected from (1) H and (2) C$_{1-6}$ alkyl; and
R$^4$ is selected from (1) H, (2) halogen, (3) —CN and (4) C$_{1-6}$ alkyl optionally substituted with —OH.
In one embodiment of the compound of formula (I), or a pharmaceutically acceptable salt thereof:
each occurrence of M is independently selected from (1) —CH═ and (2) —N═;
V is selected from (1) —CR$^b$R$^b$— and (2) —O—, wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—CHF$_2$ and (g) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens;
R$^3$ is H; and
R$^4$ is selected from (1) H, (2) halogen, (3) —CN and (4) C$_{1-4}$ alkyl optionally substituted with —OH.
In one embodiment of the compound of formula (I), or a pharmaceutically acceptable salt thereof:

L is selected from (1) —NHC(O)— and (2) —C(O)NH—;
V is selected from (1) —CH$_2$—, (2) —CHF—, (3) —CF$_2$— and (4) —O—;
R$^1$ is selected from (1) C$_{1-4}$ alkyl, (2) C$_{3-6}$ cycloalkyl, (3) phenyl and (4) 5- or 6-membered heteroaryl selected from isoxazolyl, oxadiazolyl, oxazolyl, oxoimidazolidinyl, pyranyl, pyrazinyl, pyrazolyl, pyridazinyl, pyridinyl, pyrimidinyl and pyrrolyl; wherein the phenyl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—CHF$_2$ and (g) C$_{3-6}$ cycloalkyl; and
each occurrence of R$^2$ is independently selected from (1) H, (2) halogen, (3) —CN, (4) —CH$_3$ (5) ethyl and (6) —CF$_3$.
In one embodiment of the compound of formula (I), or a pharmaceutically acceptable salt thereof:
L is selected from (1) —NHC(O)— and (2) —C(O)NH—;
V is selected from (1) —CH$_2$—, (2) —CHF—, (3) —CF$_2$— and (4) —O—;
R$^1$ is selected from (1) C$_{1-4}$ alkyl, (2) cyclopropyl, (3) phenyl and (4) 5- or 6-membered heteroaryl selected from pyrazinyl, pyrazolyl, pyridazinyl, pyridinyl and pyrimidinyl; wherein the phenyl of (3) and the heteroaryl of (4) is optionally substituted with 1 to 3 substituents independently selected from (a) halogen, (b) —CN, (c) —CF$_3$, (d) —NH$_2$, (e) —CH$_3$, (f) —CH$_2$OH, (g) —O—CHF$_2$ and (h) cyclopropyl; and
each occurrence of R$^2$ is independently selected from (1) H, (2) halogen, (3) —CN, (4) —CH$_3$ and (5) —CF$_3$, and
R$^4$ is selected from (1) H, (2) halogen, (3) —CN, (4) —CH$_3$ and (5) —CH$_2$OH.
In one embodiment of the compound of formula (I), or a pharmaceutically acceptable salt thereof, the compound is of formula (Ia):

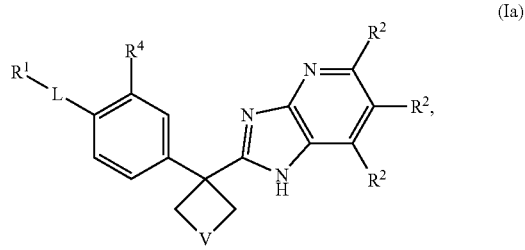

(Ia)

wherein:
L is selected from (1) a bond, (2) —NHC(O)— and (3) —C(O)NH— and (4) —NHC(O)O—;
V is selected from (1) —CR$^b$R$^b$— and (2) —O—, wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —NH$_2$, (d) C$_{1-6}$ alkyl optionally substituted with 1 to 3 substituents independently selected from halogen and —OH, (e) —O—C$_{1-6}$ alkyl optionally substituted with 1 to 3 halogens and (f) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^4$ is selected from (1) H, (2) halogen, (3) —CN and (4) C$_{1-4}$ alkyl optionally substituted with —OH.

In one embodiment of the compound of formula (Ia), or a pharmaceutically acceptable salt thereof:
L is selected from (1) —NHC(O)— and (2) —C(O)NH—;
V is selected from (1) —CR$^b$R$^b$— and (2) —O—; wherein each occurrence of R$^b$ is independently selected from (a) H and (b) halogen;
R$^1$ is selected from (1) C$_{3-6}$ cycloalkyl, (2) phenyl and (3) 5- or 6-membered heteroaryl selected from isoxazolyl, oxadiazolyl, oxazolyl, oxoimidazolidinyl, pyranyl, pyrazinyl, pyrazolyl, pyridazinyl, pyridinyl, pyrimidinyl and pyrrolyl; wherein each of the phenyl of (2) and the heteroaryl of (3) is optionally substituted with 1 to 3 substituents independently selected from (a) halogen, (b) —CN, (c) —CF$_3$, (d) C$_{1-6}$ alkyl optionally substituted with —OH, (e) —O—CHF$_2$ and (f) cyclopropyl;
each occurrence of R$^2$ is independently selected from (1) H, (2) halogen, (3) —CN, (4) —CH$_3$ and (5) —CF$_3$; and
R$^4$ is selected from (1) H, (2) halogen, (3) —CN, (4) —CH$_3$ and (5) —CH$_2$OH.

In one embodiment of the compound of formula (Ia), or a pharmaceutically acceptable salt thereof:
V is selected from (1) —CH$_2$—, (2) —CHF—, (3) —CF$_2$— and (4) —O—;
R$^1$ is selected from (1) C$_{3-6}$ cycloalkyl, (2) phenyl and (3) 5- or 6-membered heteroaryl selected from pyrazinyl, pyrazolyl, pyridazinyl, pyridinyl and pyrimidinyl; wherein the phenyl of (2) and the heteroaryl of (3) is optionally substituted with 1 to 3 substituents independently selected from (a) halogen, (b) —CN, (c) —CF$_3$, (d) —CH$_3$ (e) —CH$_2$OH, (f) —O—CHF$_2$ and (g) cyclopropyl; each occurrence of R$^2$ is independently selected from (1) H, (2) halogen, (3) —CN and (4) —CF$_3$; and
R$^4$ is selected from (1) H, (2) halogen, (3) —CN and (4) —CH$_2$OH.

In one embodiment of the compound of formula (Ia), or a pharmaceutically acceptable salt thereof:
R$^1$ is selected from (1) C$_{3-6}$ cycloalkyl, (2) phenyl and (3) 5- or 6-membered heteroaryl selected from pyrazolyl, pyridinyl and pyrimidinyl; wherein the phenyl of (2) and the heteroaryl of (3) is optionally substituted with 1 to 3 substituents independently selected from (a) halogen, (b) —CN, (c) —CF$_3$, (d) —CH$_3$, (e) —CH$_2$OH, (f) —O—CHF$_2$ and (g) cyclopropyl.

In one embodiment of the compound of formula (I), or a pharmaceutically acceptable salt thereof, the compound is of formula (Ib):

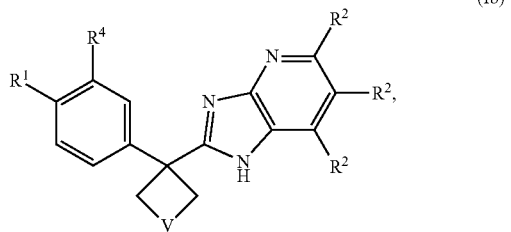

wherein:
V is selected from (1) —CR$^b$R$^b$— and (2) —O—; wherein each occurrence of R$^b$ is independently selected from (a) H, (b) —OH and (c) halogen;
R$^1$ is selected from (1) C$_{3-6}$ cycloakyl, (2) aryl and (3) 5- or 6-membered heteroaryl; wherein the aryl of (2) and the heteroaryl of (3) is optionally substituted with 1 to 3 substituents independently selected from (a) halogen, (b) —CN, (c) C$_{1-6}$ alkyl optionally substituted with 1 to 3 substituents independently selected from halogen and —OH, (d) —O—C$_{1-6}$ alkyl optionally substituted with 1 to 3 halogens and (e) C$_{3-6}$ cycloakyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^4$ is selected from (1) H, (2) halogen, (3) —CN and (4) —CH$_2$OH.

In one embodiment of the compound of formula (Ib), or a pharmaceutically acceptable salt thereof:
V is selected from (1) —CH$_2$—, (2) —CHF—, (3) —CF$_2$— and (4) —O—;
R$^1$ is a 5- or 6-membered heteroaryl selected from pyrazolyl, pyridinyl and pyrimidinyl; wherein the heteroaryl is optionally substituted with 1 to 3 substituents independently selected from (a) halogen, (b) —CN, (c) —CF$_3$, (d) C$_{1-6}$ alkyl, (e) —O—CHF$_2$ and (f) C$_{3-6}$ cycloakyl; each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^4$ is H.

In one embodiment of the compound of formula (Ib), or a pharmaceutically acceptable salt thereof:
V is selected from (1) —CH$_2$—, (2) —CHF—, (3) —CF$_2$— and (4) —O—;
R$^1$ is pyridinyl, optionally substituted with 1 to 3 substituents independently selected from (a) halogen, (b) —CN, (c) —CF$_3$, (d) —CH$_3$, (e) —O—CHF$_2$ and (f) cyclopropyl; and each occurrence of R$^2$ is independently selected from (1) H, (2) halogen, (3) —CN and (4) —CF$_3$.

In one embodiment, a compound disclosed herein is selected from the group consisting of the compounds exemplified in Examples 1 to 52; or a pharmaceutically acceptable salt thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkenyl" refers to both branched- and straight-chain unsaturated aliphatic hydrocarbon groups of 2 to 12 carbon atoms and having at least one carbon-carbon double bond.

Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a monocyclic saturated carbocyclic ring having the specified number of carbon atoms. For example, $C_{3-6}$ cycloalkyl refers to a cycloalkyl group as defined herein having 3 to 6 carbon atoms. Examples of cycloalkyl include, but are not limited to, cyclopropyl, cyclobutyl, cyclopentyl, and cyclohexyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. An aromatic heterocyclyl is also referred to as a "heteroaryl". In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, a heterocyclyl is a 5, or 6-membered heteroaryl group. Suitable 5, or 6-membered heteroaryl groups include, but are not limited to, 5- or 6-membered heteroaryl selected from isoxazolyl, oxadiazolyl, oxazolyl, oxoimidazolidinyl, pyranyl, pyrazinyl, pyrazolyl, pyridazinyl, pyridinyl, pyrimidinyl and pyrrolyl.

In one embodiment, a 5, or 6-membered heteroaryl group is selected from pyrazinyl, pyrazolyl, pyridazinyl, pyridinyl and pyrimidinyl. In one embodiment, 5, or 6-membered heteroaryl group is selected from pyrazolyl, pyridinyl and pyrimidinyl. In yet another embodiment, a 5, or 6-membered heteroaryl group is pyridinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as C, $^{18}F$, $^{15}O$ and $^{13}N$, may be particularly desirable for PET or SPECT studies.

Isotopically-labeled compounds disclosed herein can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of the compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pregelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL

The following examples are intended to be illustrative only and not limiting in any way. Abbreviations used are those conventional in the art or the following.

ACN acetonitrile
aq. Aqueous
° C. degree Celsius
Celite® diatomaceous earth ($SiO_2$)
DAST (dimethylamino)sulfur trifluoride
DCM dichloromethane
DIEA N,N-diisopropylethylamine
DMA dimethylamine
DMF N,N-dimethylformamide
DMSO dimethylsulfoxide
dppf 1,1'-bis(diphenylphosphino)ferrocene
EDC N-(3-dimethylaminopropyl)-N'-ethylcarbodiimide hydrochloride
EI electron ionization
EMEM Eagle's minimal essential medium
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HPLC high pressure liquid chromatography
kg kilogram
L liter
LC liquid chromatography
LCMS liquid chromatography and mass spectrometry
mCPBA 3-chloroperbenzoic acid
MeOH methanol
MS mass spectrometry
MTBE methyl tert-butyl ether
min minutes
mL milliliter(s)
m/z mass to charge ratio
nm nanometer
nM nanomolar
N normal
NBS N-bromosuccinimide
NCS N-chlorosuccinimide
$Pd_2(dba)_3$ tris(dibenzylideneacetone)dipalladium(0)
$Pd(dppf)_2Cl_2$ [1,1'-bis(diphenylphosphino)ferrocene]dichloropalladium(II)
$PdCl_2(dtbpf)$ [1,1'-bis(di-tert-butylphosphino)ferrocene]dichloropalladium(II)
PE petroleum ether
PS polystyrene
RPMI medium Roswell Park Memorial Institute medium
RT or rt room temperature
sat. saturated
t-BuOH tert-butanol
TBDMSCl tert-butyldimethylsilyl chloride
TBNF tetra-n-butylammonium fluoride
TEA triethyl amine
TFA trifluoroacetic acid
THF tetrahydrofuran
TLC thin layer chromatography
TMSOK potassium trimethylsilanolate
uL microliter(s)

The following examples are intended to be illustrative only and not limiting in any way. Abbreviations used are those conventional in the art or the following.

General Synthetic Schemes

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

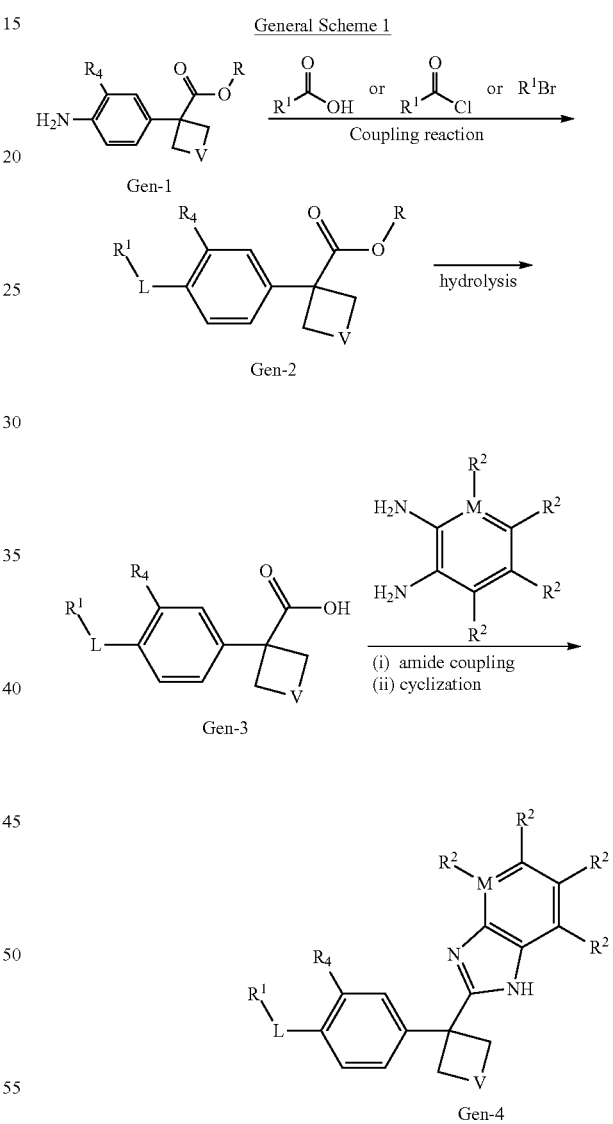

In General Scheme 1, commercially available or synthetically prepared Gen-1 is coupled with an acid, acid chloride or aryl bromide to generate Gen-2, which is converted to Gen-3 through ester hydrolysis. Gen-3 is elaborated to Gen-4 by amide coupling with diverse phenyl or heterocyclic diamines, followed by dehydrative cyclization. The representative compounds are described in more detail below.

General Scheme 2

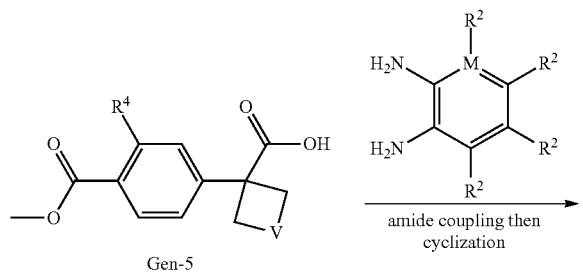

Gen-5

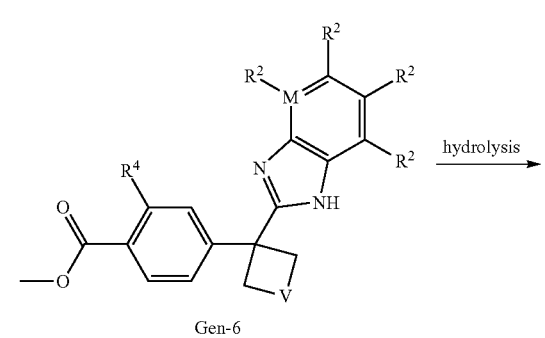

Gen-6

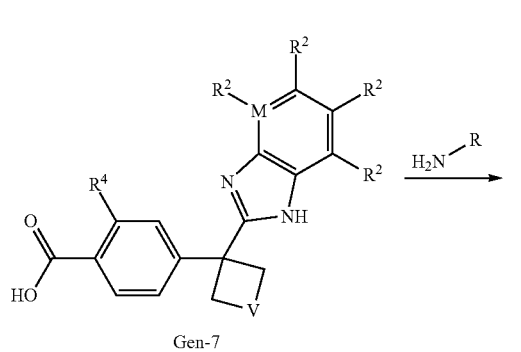

Gen-7

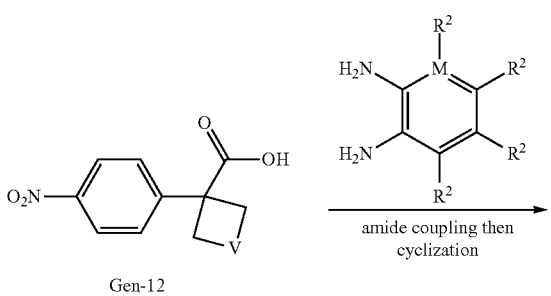

Gen-8

In General Scheme 2, commercially available or synthetically prepared Gen-5 is elaborated to Gen-6 by amide coupling with diverse phenyl or heterocyclic diamines, followed by dehydrative cyclization. Gen-6 is converted to Gen-7 through ester hydrolysis, then reacted with different amines to generate Gen-8. The representative compounds are described in more detail below.

General Scheme 3

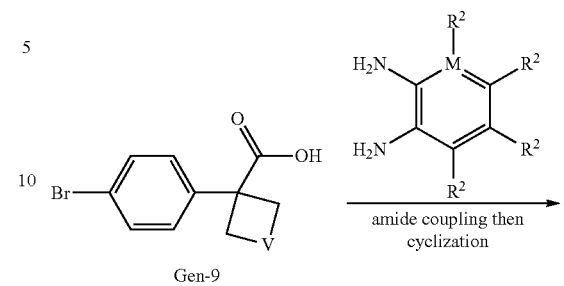

Gen-9

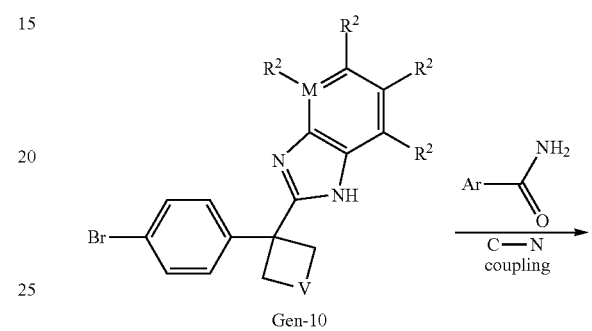

Gen-10

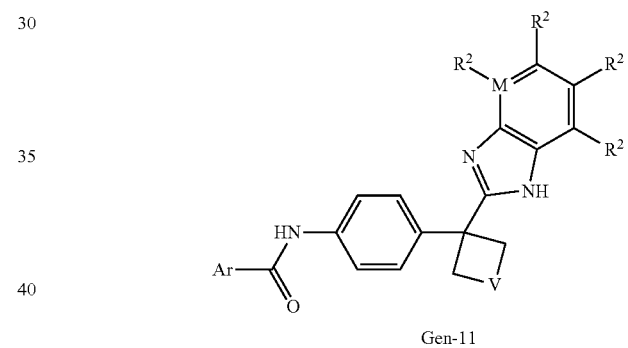

Gen-11

In General Scheme 3, commercially available or synthetically prepared Gen-9 is elaborated to Gen-10 by amide coupling with diverse phenyl or heterocyclic diamines, followed by dehydrative cyclization. Gen-10 is converted to Gen-11 through CuI catalyzed C—N coupling reaction with diversed aryl amides. The representative compounds are described in more detail below.

General Scheme 4

Gen-12

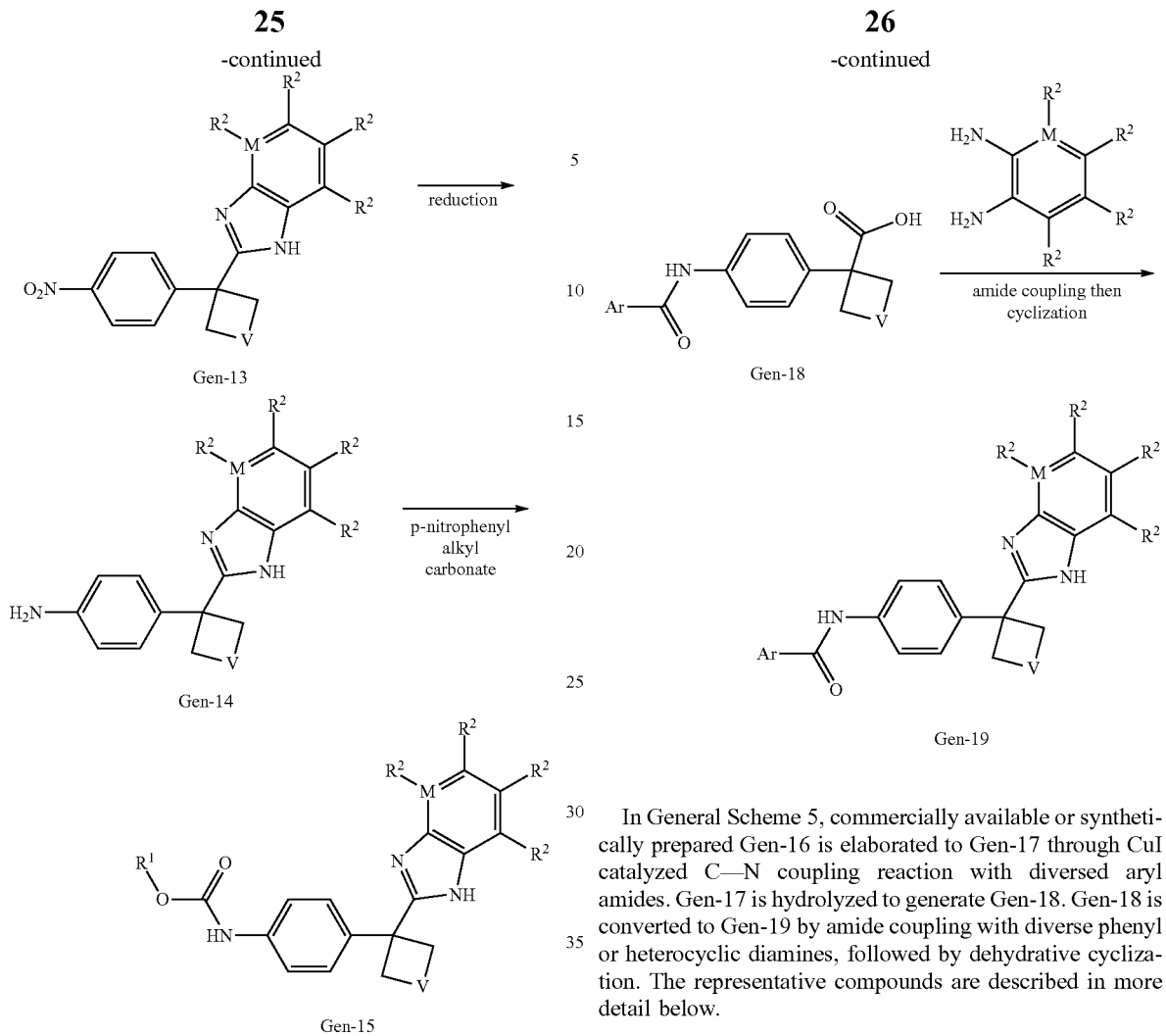

In General Scheme 4, commercially available or synthetically prepared Gen-12 is elaborated to Gen-13 by amide coupling with diverse phenyl or heterocyclic diamines, followed by dehydrative cyclization. Gen-13 is reduced to Gen-14 followed by reaction with p-nitrophenyl alkyl carbonate to give Gen-15. The representative compounds are described in more detail below.

In General Scheme 5, commercially available or synthetically prepared Gen-16 is elaborated to Gen-17 through CuI catalyzed C—N coupling reaction with diversed aryl amides. Gen-17 is hydrolyzed to generate Gen-18. Gen-18 is converted to Gen-19 by amide coupling with diverse phenyl or heterocyclic diamines, followed by dehydrative cyclization. The representative compounds are described in more detail below.

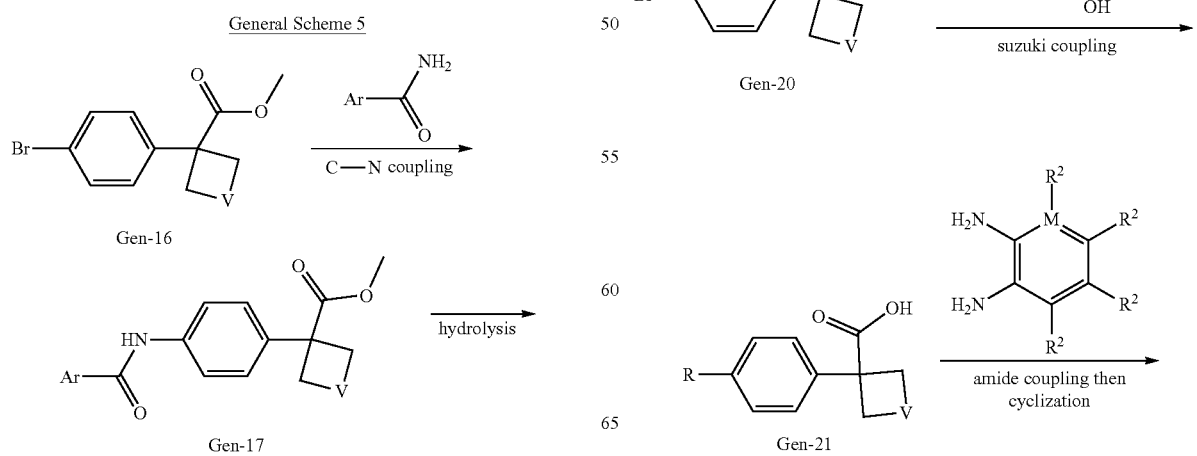

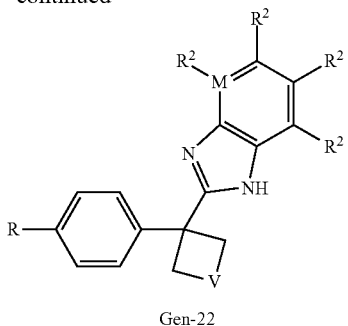

Gen-22

In General Scheme 6, commercially available or synthetically-prepared Gen-20 is coupled with boronic esters or boronic acids to generate Gen-21, which is elaborated to Gen-22 by amide coupling with diverse phenyl or heterocyclic diamines, followed by dehydrative cyclization. The representative compounds are described in more detail below.

General Scheme 7

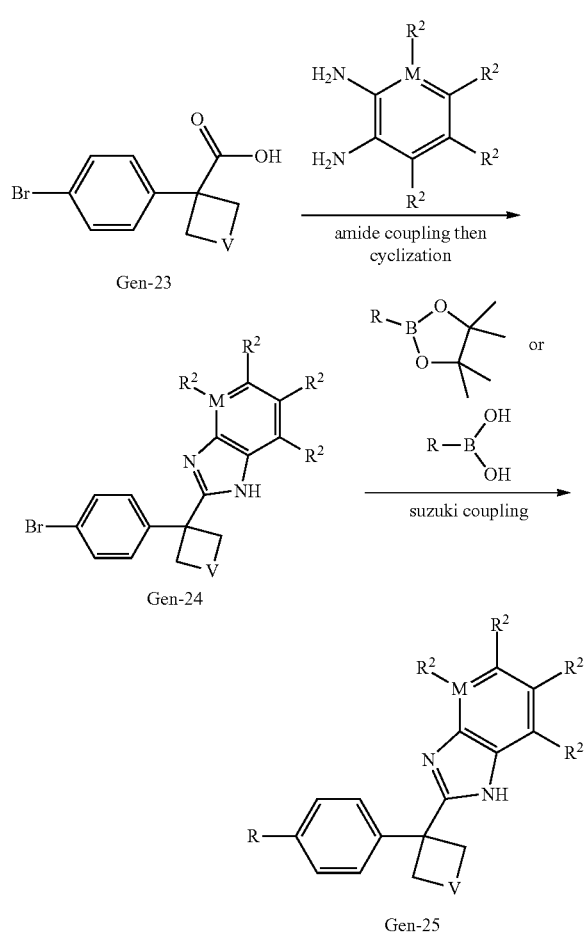

In General Scheme 7, commercially available or synthetically prepared Gen-23 is elaborated to Gen-24 by amide coupling with diverse phenyl or heterocyclic diamines, followed by dehydrative cyclization. Gen-24 is converted to Gen-25 through suzuki coupling with diverse boronic esters or boronic acids. The representative compounds are described in more detail below.

EXAMPLES

Example 1: 3-Chloro-N-(4-(1-(6-(trifluoromethyl)-1H-imidazo[4,5-b]pyridin-2-yl)cyclobutyl)phenyl)benzamide (Ex. 1)

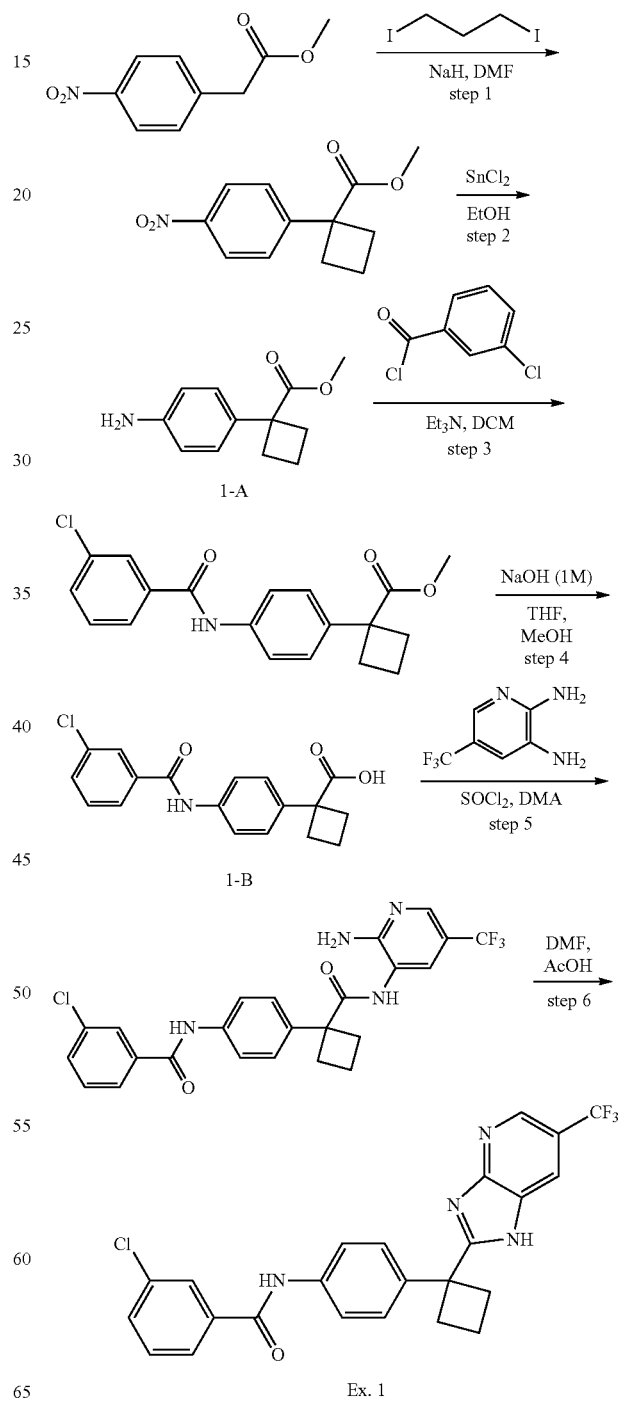

Ex. 1

Step 1: Methyl 1-(4-nitrophenyl)cyclobutane-1-carboxylate

Methyl 2-(4-nitrophenyl)acetate (6.0 g, 31 mmol) was dissolved in DMF (100 mL). The solution was cooled to 0° C. in an ice bath. NaH (2.50 g, 62.5 mmol, 60% in mineral oil) was added slowly and cautiously. The resulting mixture was allowed to warm to RT and stirred for 15 min. The mixture was cooled again to 0° C. and 1,3-diiodopropane (6.0 mL, 52 mmol) was added dropwise. The resulting mixture was allowed to stir at 0° C. for 30 min, then 0° C. to 10° C. for 1.5 h. The solution was cooled to 0° C. and quenched with water. The reaction mixture was extracted with DCM (30 mL×3). The combined organic layers were washed with water, brine, dried over $Na_2SO_4$, filtered and concentrated in vacuo to afford a residue. The residue was purified by column chromatography on silica gel (EtOAc in hexane, 0-20% gradient) to afford methyl 1-(4-nitrophenyl) cyclobutanecarboxylate.

Step 2: Methyl 1-(4-aminophenyl)cyclobutane-1-carboxylate (I-A)

To a flask were added methyl 1-(4-nitrophenyl)cyclobutanecarboxylate (966 mg, 4.11 mmol), ethanol (10 mL) and tin(II)chloride (3115 mg, 16.43 mmol). The resulting mixture was stirred at 85° C. for 4 h. After cooling to RT, the mixture was adjusted to pH~10 with concentrated aq. NaOH (1M). The mixture was extracted with EtOAc (50 mL×3). The combined organic layers were washed with water, brine, dried over $Na_2SO_4$, filtered and concentrated in vacuo to afford methyl 1-(4-aminophenyl)cyclobutanecarboxylate (I-A). MS (EI) m/z 206 $[M+H]^+$.

Step 3: Methyl 1-(4-(3-chlorobenzamido)phenyl)cyclobutane-1-carboxylate

To the solution of I-A (846 mg, 4.12 mmol) in DCM (10 mL) at 0° C., was added $Et_3N$ (700 μl, 5.02 mmol), then 3-chlorobenzoyl chloride (600 μl, 4.69 mmol) was added dropwise. The mixture was allowed to warm to RT and stirred for 18 h. The reaction mixture was concentrated in vacuo and purified by column chromatography on silica gel (EtOAc in hexane, 0-20% gradient) to afford methyl 1-(4-(3-chlorobenzamido)phenyl)cyclobutanecarboxylate. MS (EI) m/z 344 $[M+H]^+$.

Step 4: 1-(4-(3-Chlorobenzamido)phenyl)cyclobutane-1-carboxylic Acid (I-B)

To the solution of methyl 1-(4-(3-chlorobenzamido)phenyl)cyclobutanecarboxylate (1.04 g, 3.02 mmol) in THF (12 mL), were added MeOH (5 mL) and NaOH (10 mL, 10 mmol, 1M). The mixture was stirred at RT for 18 h. The organic solvent was removed in vacuo and the aq. residue was adjusted to pH~3 by adding HCl (1 M). The aq. solution was extracted with EtOAc (30 mL×3). The combined organic layers were washed with brine, dried over $Na_2SO_4$ and concentrated in vacuo to afford 1-(4-(3-chlorobenzamido)phenyl)cyclobutanecarboxylic acid (I-B). MS (EI) m/z 330 $[M+H]^+$.

Step 5: N-(4-(1-((2-amino-5-(trifluoromethyl)pyridin-3-yl)carbamoyl)cyclobutyl)phenyl)-3-chlorobenzamide To the solution of I-B (499 mg, 1.51 mmol) in DMA (2.5 mL) at −5° C. was added thionyl chloride (0.14 mL, 1.9 mmol). After stirring for 40 min at −5° C., a solution of 5-(trifluoromethyl)pyridine-2,3-diamine (295 mg, 1.66 mmol) in DMA (3 mL) was added to this reaction mixture. The reaction mixture was stirred at RT for 18 h. The reaction was quenched with water and extracted with DCM. Solid precipitated out from the organic phase, which was collected via filtration to afford N-(4-(1-((2-amino-5-(trifluoromethyl)pyridin-3-yl)carbamoyl)cyclobutyl)phenyl)-3-chlorobenzamide. MS (EI) m/z 489 $[M+H]^+$.

Step 6: 3-Chloro-N-(4-(1-(6-(trifluoromethyl)-1H-imidazo[4,5-b]pyridin-2-yl)cyclobutyl)phenyl)benzamide (Ex. 1)

To a vial were added N-(4-(1-((2-amino-5-(trifluoromethyl)pyridin-3-yl)carbamoyl)cyclobutyl)phenyl)-3-chlorobenzamide (739 mg, 1.51 mmol), DMF (2400 μl) and acetic acid (600 μl). The mixture was irradiated in the microwave at 130° C. for 12 h. The solvent was removed in vacuo, and the residue was basified with sat. $NaHCO_3$ and extracted with DCM (20 mL×3). The organic phase was washed with brine, dried over $Na_2SO_4$ and concentrated in vacuo to afford a crude product. The crude product was recrystallized from DCM to afford the title compound (Ex. 1). $^1$H NMR (600 MHz, DMSO-$d_6$) δ 13.34 (s, 1H), 10.29 (s, 1H), 8.59 (s, 1H), 8.32 (s, 1H), 7.94 (s, 1H), 7.85 (d, J=7.4 Hz, 1H), 7.68 (d, J=7.6 Hz, 2H), 7.61 (d, J=7.3 Hz, 1H), 7.51 (t, J=7.8 Hz, 1H), 7.32 (d, J=8.2 Hz, 2H), 3.09-2.93 (m, 2H), 2.78-2.59 (m, 2H), 2.06-1.81 (m, 2H). MS (EI) m/z 471 $[M+H]^+$.

Example 2: 3-Chloro-N-(4-(1-(6-cyano-1H-imidazo[4,5-b]pyridin-2-yl)cyclobutyl)phenyl)benzamide (Ex. 2)

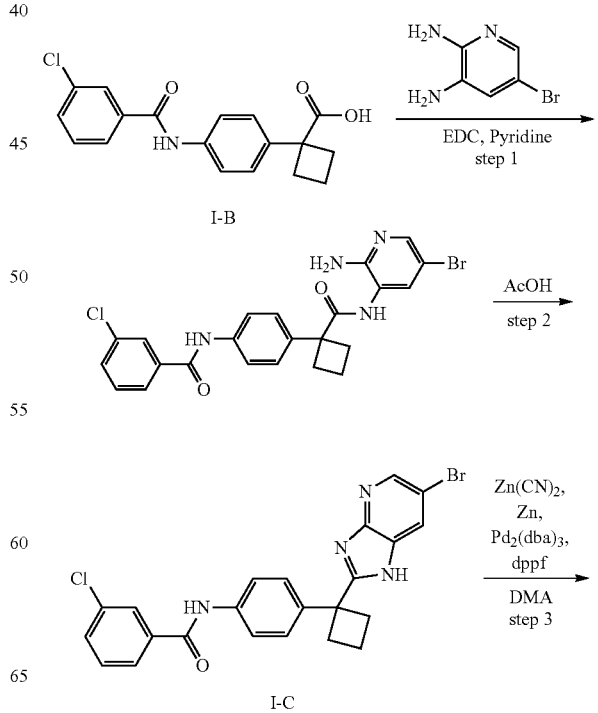

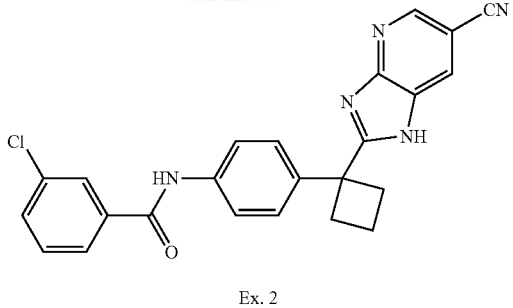

Ex. 2

Step 1: N-(4-(1-((2-amino-5-bromopyridin-3-yl)carbamoyl)cyclobutyl)phenyl)-3-chlorobenzamide To a stirred solution of 5-bromopyridine-2,3-diamine (473 mg, 2.52 mmol) and 1-(4-(3-chlorobenzamido)phenyl)cyclobutanecarboxylic acid (830 mg, 2.52 mmol) in pyridine (5 mL) was added EDC (1447 mg, 7.550 mmol) at 20° C. The reaction mixture was stirred at 30° C. for 3 h. After cooling down to RT, the reaction mixture was diluted with water (40 mL) and extracted with EtOAc (40 mL×3). The organic layers were combined, washed with brine (50 mL), dried over $Na_2SO_4$, filtered and concentrated in vacuo to give crude N-(4-(1-((2-amino-5-bromopyridin-3-yl)carbamoyl)cyclobutyl)phenyl)-3-chlorobenzamide. MS (EI) m/z 499 $[M+H]^+$.

Step 2: N-(4-(1-(6-bromo-1H-imidazo[4,5-b]pyridin-2-yl)cyclobutyl)phenyl)-3-chlorobenzamide (I-C)

To a flask were added N-(4-(1-((2-amino-5-bromopyridin-3-yl)carbamoyl)cyclobutyl) phenyl)-3-chlorobenzamide (840 mg, 1.681 mmol) and AcOH (10 mL). The reaction mixture was stirred at 120° C. for 18 h. The solvent was removed in vacuo to give N-(4-(1-(6-bromo-1H-imidazo[4,5-b]pyridin-2-yl)cyclobutyl)phenyl)-3-chlorobenzamide (I-C). MS (EI) m/z 481 $[M+H]^+$.

Step 3: 3-Chloro-N-(4-(1-(6-cyano-1H-imidazo[4,5-b]pyridin-2-yl)cyclobutyl)phenyl)benzamide (Ex. 2)

To a solution of I-C (550 mg, 1.14 mmol) in DMA (2 mL) were added zinc (15 mg, 0.23 mmol), $Zn(CN)_2$ (134 mg, 1.14 mmol), $Pd_2(dba)_3$ (21 mg, 0.023 mmol) and dppf (38 mg, 0.069 mmol). The reaction mixture was irradiated in the microwave at 120° C. for 30 min. After cooling to RT, water (30 mL) was added, the reaction mixture was extracted with EtOAc (20 mL×3). The organic layers were combined, washed with brine, dried over $Na_2SO_4$, filtered and concentrated in vacuo to afford a residue, which was purified by reversed phase HPLC, eluting with water (0.05% ammonia hydroxide v/v)-ACN, followed by lyophilization to give the title compound (Ex. 2). $^1$H NMR (400 MHz, $CD_3OD$) δ 8.70-8.56 (m, 1H), 8.38-8.11 (m, 1H), 7.93 (s, 1H), 7.84 (d, J=7.9 Hz, 1H), 7.69 (d, J=7.3 Hz, 2H), 7.61-7.55 (m, 1H), 7.53-7.46 (m, 1H), 7.42 (d, J=8.4 Hz, 2H), 3.20-2.95 (m, 2H), 2.95-2.75 (m, 2H), 2.25-2.00 (m, 2H). MS (EI) m/z 428 $[M+H]^+$.

Example 3: 3-Cyano-N-(4-(1-(6-cyano-1H-imidazo[4,5-b]pyridin-2-yl)cyclobutyl)phenyl)benzamide (Ex. 3)

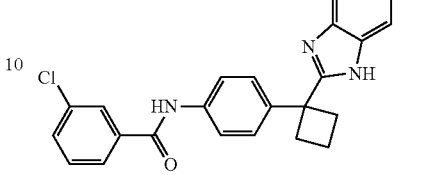

I-C

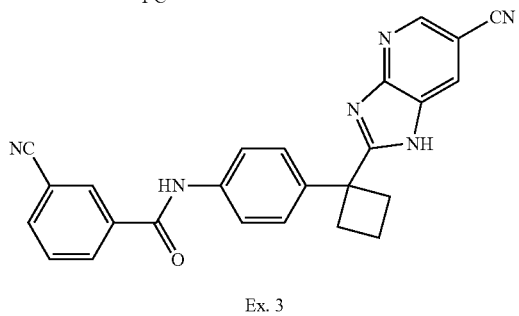

Ex. 3

To a vial were added dppf (2.0 mg, 3.6 μmol), zinc (1.0 mg, 0.015 mmol), $Pd_2(dba)_3$ (1.0 mg, 1.1 μmol), I-C (30 mg, 0.062 mmol), $Zn(CN)_2$ (15 mg, 0.13 mmol) and DMA (2 mL). The reaction mixture was irradiated in the microwave at 150° C. for 30 min, then purified by reversed phase HPLC, eluting with water (0.1% TFA)-ACN, followed by lyophilization to afford the title compound (Ex. 3). $^1$H NMR (400 MHz, $CD_3OD$) δ 8.68 (s, 1H), 8.29 (d, J=15.4 Hz, 2H), 8.20 (d, J=7.4 Hz, 1H), 7.92 (d, J=6.6 Hz, 1H), 7.66-7.75 (m, 3H), 7.44 (d, J=8.3 Hz, 2H), 3.25-3.00 (m, 2H), 2.83-2.95 (m, 2H), 2.05-2.24 (m, 2H); MS (EI) m/z 419 $[M+H]^+$.

Example 4: N-(4-(1-(1H-benzo[d]imidazol-2-yl)cyclobutyl)phenyl)-3-chlorobenzamide (Ex. 4)

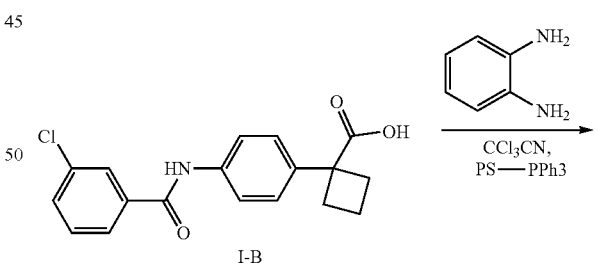

I-B

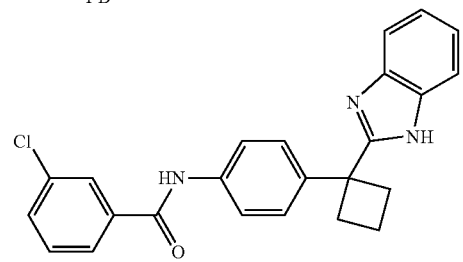

Ex. 4

To a vial were added 1-(4-(3-chlorobenzamido)phenyl) cyclobutanecarboxylic acid (14 mg, 0.042 mmol), benzene-1,2-diamine (5.5 mg, 0.051 mmol), trichloroacetonitrile (23 mg, 0.16 mmol), PS—PPh₃ (33.2 mg, 0.126 mmol), THF (600 μl) and DIEA (15 μl, 0.084 mmol). The mixture was irradiated in the microwave at 100° C. for 15 min. Then the mixture was filtered and purified by reversed phase HPLC, eluting with water (0.1% TFA)-ACN to afford the title compound as a TFA salt (Ex. 4). ¹H NMR (600 MHz, DMSO-d₆) δ 10.37 (s, 1H), 7.94 (s, 1H), 7.85 (d, J=7.7 Hz, 1H), 7.76 (d, J=8.4 Hz, 2H), 7.70-7.57 (m, 3H), 7.53 (t, J=7.9 Hz, 1H), 7.41 (d, J=8.0 Hz, 4H), 3.09-2.95 (m, 2H), 2.78 (q, J=8.6 Hz, 2H), 2.11-1.87 (m, 2H); MS (EI) m/z 402 [M+H]⁺.

Example 5: N-(4-(1-(1H-imidazo[4,5-b]pyridin-2-yl)cyclobutyl)phenyl)-3-chlorobenzamide (Ex. 5)

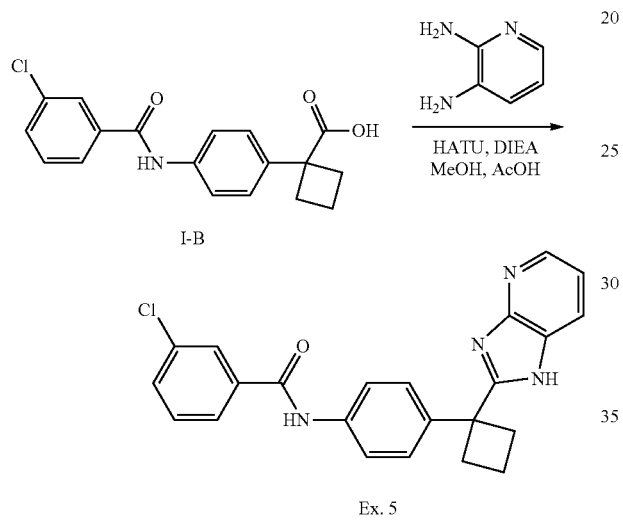

To a vial were added I-B (10 mg, 0.030 mmol), pyridine-2,3-diamine (3.6 mg, 0.033 mmol), HATU (14 mg, 0.036 mmol), DMF (300 μl) and DIEA (20 μl, 0.11 mmol). The mixture was heated at 80° C. for 3 h. The solvent was removed in vacuo, then the residue was dissolved into MeOH (400 uL) and acetic acid (100 μL). The mixture was irradiated in the microwave at 130° C. for 11 h. The mixture was filtered and purified by reversed phase HPLC, eluting with ACN/water (0.1% TFA) to afford the title compound as a TFA salt (Ex. 5). ¹H NMR (600 MHz, DMSO-d₆) δ 10.31 (s, 1H), 8.45-8.30 (m, 1H), 8.04 (d, J=7.6 Hz, 1H), 7.94 (s, 1H), 7.85 (d, J=7.7 Hz, 1H), 7.70 (d, J=8.3 Hz, 2H), 7.62 (d, J=7.7 Hz, 1H), 7.52 (t, J=7.8 Hz, 1H), 7.40-7.25 (m, 3H), 3.08-2.90 (m, 2H), 2.70 (q, J=8.9 Hz, 2H), 2.07-1.84 (m, 2H). MS (EI) m/z 403 [M+H]⁺.

Example 6: 3-Cyano-N-(4-(1-(6-(trifluoromethyl)-3H-imidazo[4,5-b]pyridin-2-yl)cyclobutyl)phenyl) benzamide

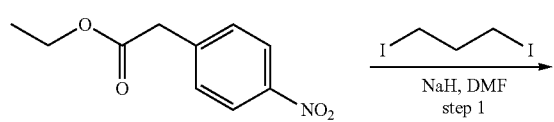

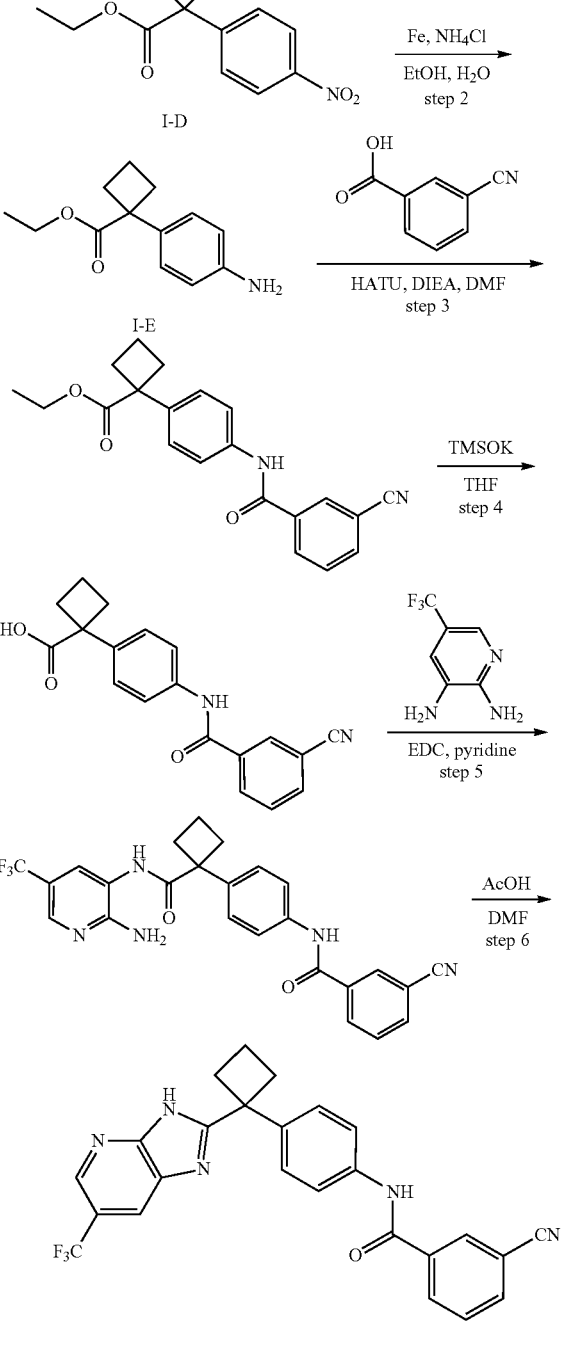

Step 1: Ethyl 1-(4-nitrophenyl)cyclobutanecarboxylate (I-D)

To a solution of ethyl 2-(4-nitrophenyl)acetate (9.0 g, 43 mmol) in DMF (100 mL) was added NaH (3.6 g, 90 mmol, 60% in oil) at 0° C. Then the reaction mixture was allowed to warm to RT and stirred for 15 min. The mixture was cooled to 0° C. again and 1,3-diiodopropane (10 mL, 89 mmol) was added. The resulting mixture was stirred at 0° C. for 30 min, then warmed to RT and stirred at RT for 1 h. The reaction was diluted with NH₄Cl (sat., 200 mL), extracted with EtOAc. The combined organic layers were washed with brine, dried over Na₂SO₄, filtered and concentrated in vacuo to afford a residue, which was purified by column chromatography on silica gel (EtOAc in petroleum ether: 0-5% gradient) to give the title compound (I-D). $^1$H NMR (400 MHz, CDCl₃) δ 8.23-8.12 (m, 2H), 7.52-7.38 (m, 2H), 4.18-4.04 (m, 2H), 2.94-2.82 (m, 2H), 2.57-2.45 (m, 2H), 2.18-2.04 (m, 1H), 2.00-1.75 (m, 1H), 1.22-1.12 (m, 3H).

Step 2: Ethyl 1-(4-aminophenyl)cyclobutane-1-carboxylate (I-E)

To a solution of I-D (22 g, 88 mmol) in ethanol (200 mL) and water (50 mL) were added iron (14.8 g, 265 mmol) and NH₄Cl (47.2 g, 883 mmol) at RT. After the addition was finished, the mixture was stirred under reflux for 2 h. Then the salt was removed by filtration. The filtrate was concentrated in vacuo. The residue was diluted with water and extracted with ethyl acetate. The combined organic layers were washed with brine, dried over Na₂SO₄, filtered and concentrated in vacuo to give the crude title compound (I-E), which was used directly in next step without further purification. MS (EI) m/z 220 [M+H]⁺.

Step 3: Ethyl 1-(4-(3-cyanobenzamido)phenyl)cyclobutane-1-carboxylate

To a stirred solution of 3-cyanobenzoic acid (15.3 g, 104 mmol) in DMF (250 mL) was added HATU (49.4 g, 130 mmol) and DIEA (45.4 mL, 260 mmol) at RT. After the addition was finished, the reaction was stirred at RT for 30 min, followed by the addition of I-E (19 g, 87 mmol). The reaction mixture was stirred at RT for 16 h. The reaction was diluted with water, extracted with ethyl acetate. The combined organic layers were washed with brine, dried over Na₂SO₄, filtered and concentrated in vacuo to afford a residue, which was purified by column chromatography on silica gel (EtOAc in petroleum ether: 0-50% gradient) to give the title compound. MS (EI) m/z 371 [M+Na]⁺.

Step 4: 1-(4-(3-Cyanobenzamido)phenyl)cyclobutane-1-carboxylic Acid

To a solution of ethyl 1-(4-(3-cyanobenzamido)phenyl)cyclobutanecarboxylate (17.0 g, 48.8 mmol) in THF (200 mL) was added TMSOK (12.5 g, 98.0 mmol) at RT. After addition was finished, the mixture was stirred at RT for 16 h. The reaction was diluted with water, 3 N HCl was added to adjust pH~4, then extracted with ethyl acetate. The combined organic layers were washed with brine, dried over Na₂SO₄, filtered and concentrated in vacuo to give crude title compound, which was used directly in the next step without further purification. MS (EI) m/z 321 [M+H]⁺.

Step 5: N-(4-(1-((2-amino-5-(trifluoromethyl)pyridin-3-yl)carbamoyl)cyclobutyl)phenyl)-3-cyanobenzamide To a stirred solution of 1-(4-(3-cyanobenzamido)phenyl)cyclobutanecarboxylic acid (65 mg, 0.20 mmol) in pyridine (2 mL) was added EDC (97 mg, 0.51 mmol) and 5-(trifluoromethyl)pyridine-2,3-diamine (30 mg, 0.17 mmol) at RT. After the addition was finished, the mixture was stirred at 40° C. for 16 h. The reaction was diluted with water and extracted with ethyl acetate. The combined organic layers were washed with brine, dried over Na₂SO₄, filtered and concentrated in vacuo to afford a residue, which was purified by reversed phase HPLC, eluting with water (0.1% TFA)-ACN to give the title compound. MS (EI) m/z 480 [M+H]⁺.

Step 6: 3-Cyano-N-(4-(1-(6-(trifluoromethyl)-3H-imidazo[4,5-b]pyridin-2-yl)cyclobutyl)phenyl)benzamide (Ex. 6)

To a stirred solution of N-(4-(1-((2-amino-5-(trifluoromethyl)pyridin-3-yl)carbamoyl)cyclobutyl)phenyl)-3-cyanobenzamide (30 mg, 0.063 mmol) in DMF (80 mL) was added acetic acid (3.6 µl, 0.063 mmol) at RT. After the addition was finished, the reaction was stirred at 130° C. for 16 h. The solvent was removed in vacuo. The residue was purified by reversed phase HPLC, eluting with water (0.1% TFA)-ACN to afford the title compound as a TFA salt (Ex. 6). $^1$H NMR (400 MHz, CD₃OD) δ 8.71 (s, 1H), 8.28-8.25 (m, 2H), 8.21-8.19 (d, J=8.0 Hz, 1H,), 7.94-7.92 (d, J=7.6 Hz, 1H), 7.75-7.72 (m, 2H), 7.71-7.69 (m, 1H), 7.48-7.46 (d, J=8.8 Hz, 2H), 3.12-3.08 (m, 2H), 2.92-2.86 (m, 2H), 2.18-2.12 (m, 2H); MS (EI) m/z 462 [M+H]⁺.

Examples 7-10

Examples 7-10 were made using similar procedures as for Example 6.

| Ex. # | Structure | Chemical Name | Mass [M + H]+ |
|---|---|---|---|
| 7 | 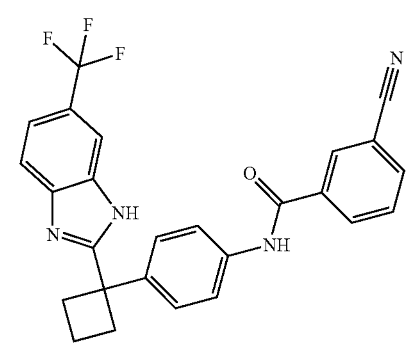 [SMILES: N#Cc1cccc(C(=O)Nc2ccc(C3(c4nc5ccc(C(F)(F)F)cc5[nH]4)CCC3)cc2)c1] | 3-cyano-N-(4-{1-[6-(trifluoromethyl)-1H-benzimidazol-2-yl]cyclobutyl}phenyl)benzamide | Calc'd 461, Found 461 |

-continued
| Ex. # | Structure | Chemical Name | Mass [M + H]+ |
|---|---|---|---|
| 8 | 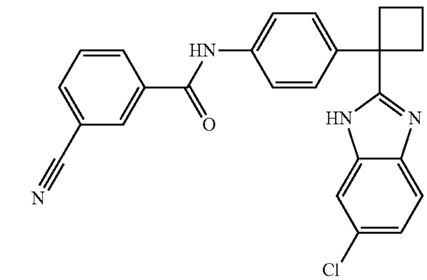 [SMILES: N#Cc1cccc(C(=O)Nc2ccc(C3(c4nc5ccc(Cl)cc5[nH]4)CCC3)cc2)c1] | N-{4-[1-(7-chloro-1H-benzimidazol-2-yl)cyclobutyl]phenyl}-3-cyanobenzamide | Calc'd 427, found 427 |
| 9 | 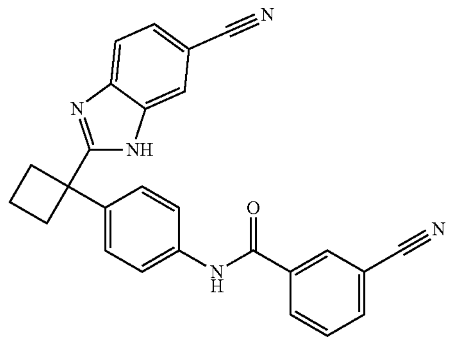 [SMILES: N#Cc1cccc(C(=O)Nc2ccc(C3(c4nc5ccc(C#N)cc5[nH]4)CCC3)cc2)c1] | 3-cyano-N-{4-[1-(7-cyano-1H-benzimidazol-2-yl)cyclobutyl]phenyl}benzamide | Calc'd 418, found 418 |
| 10 | 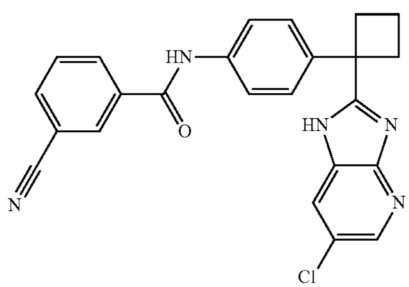 [SMILES: N#Cc1cccc(C(=O)Nc2ccc(C3(c4nc5ncc(Cl)cc5[nH]4)CCC3)cc2)c1] | N-{4-[1-(6-chloro-1H-imidazo[4,5-b]pyridin-2-yl)cyclobutyl]phenyl}-3-cyanobenzamide | Calc'd 428, found 428 |
Example 11: N-(4-(3-(6-chloro-1H-benzo[d]imidazol-2-yl)oxetan-3-yl)phenyl)-3-cyanobenzamide (Ex. 11)
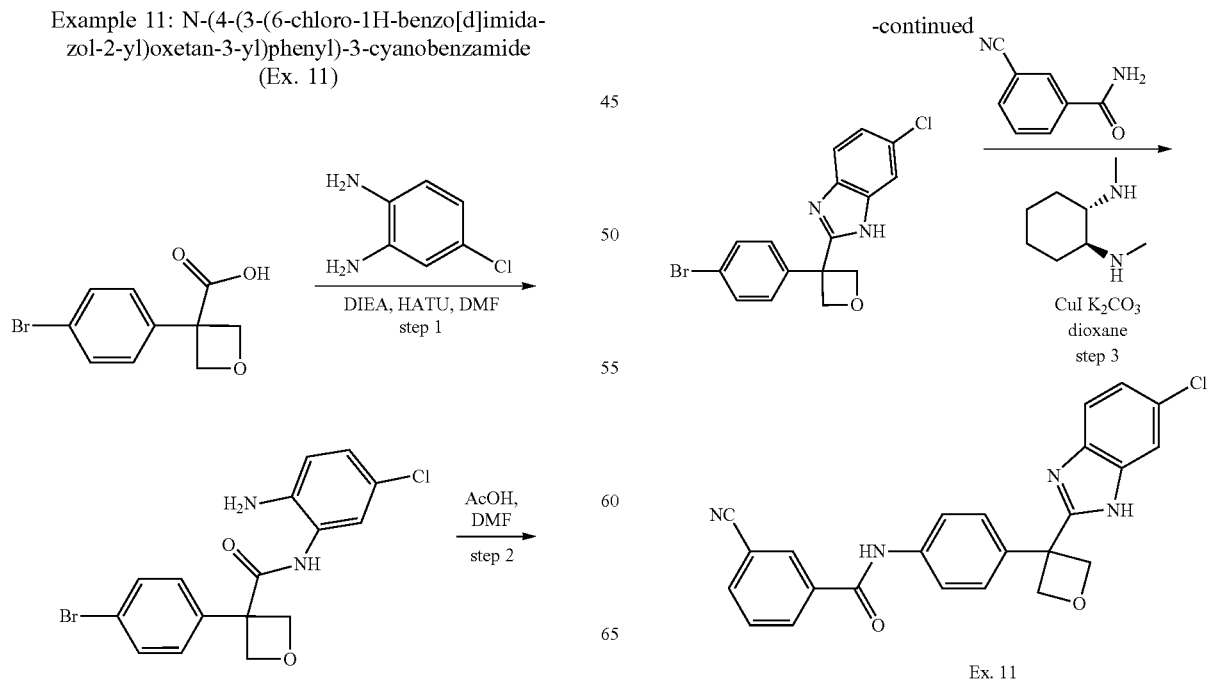
Ex. 11

Step 1: N-(2-amino-5-chlorophenyl)-3-(4-bromphenyl)oxetane-3-carboxamide

To a flask were added 3-(4-bromphenyl)oxetane-3-carboxylic acid (997 mg, 3.88 mmol), 4-chlorobenzene-1,2-diamine (664 mg, 4.65 mmol), HATU (2212 mg, 5.820 mmol), DMF (18 ml) and DIEA (2.0 ml, 11 mmol). The mixture was stirred at RT for 18 h. The solvent was evaporated in vacuo to afford a residue, which was purified by column chromatography on silica gel (EtOAc in hexane, 0-50% gradient) to afford the title compound. MS (EI) m/z 381 [M+H]+.

Step 2: 2-(3-(4-Bromophenyl)oxetan-3-yl)-6-chloro-1H-benzo[d]imidazole

To a vial containing N-(2-amino-5-chlorophenyl)-3-(4-bromophenyl)oxetane-3-carboxamide (590 mg, 1.55 mmol) were added DMF (5 ml) and acetic acid (1.25 ml). The mixture was irradiated in microwave at 150° C. for 1 h. The solvent was evaporated in vacuo to afford a residue. To the residue were added EtOAc and NaHCO₃ (sat.), the organic phase were washed with brine, dried over Na₂SO₄, filtered and concentrated in vacuo to afford a crude title compound, which was used in next step directly. MS (EI) m/z 363 [M+H]+.

Step 3: N-(4-(3-(6-chloro-1H-benzo[d]imidazol-2-yl)oxetan-3-yl)phenyl)-3-cyanobenzamide (Ex. 11)

To a vial were added 2-(3-(4-bromophenyl)oxetan-3-yl)-6-chloro-1H-benzo[d]imidazole (50 mg, 0.14 mmol), 3-cyanobenzamide (24.1 mg, 0.165 mmol), (1S,2S)—N,N'-dimethylcyclohexane-1,2-diamine (7.8 mg, 0.055 mmol), copper(I) iodide (5.2 mg, 0.028 mmol), K₂CO₃ (44 mg, 0.32 mmol) and dioxane (700 µl). The mixture was evacuated and backfilled with N₂ for 4 times, then heated at 120° C. for 17 h. The mixture was filtered and purified by reversed phase HPLC, eluting with water (0.1% TFA)-ACN to afford the title compound as a TFA salt (Ex. 11). ¹H NMR (499 MHz, DMSO-d₆) δ 10.50 (s, 1H), 8.40 (s, 1H), 8.24 (d, J=7.1 Hz, 1H), 8.07 (d, J=6.8 Hz, 1H), 7.88-7.70 (m, 3H), 7.71-7.50 (m, 2H), 7.38 (d, J=7.5 Hz, 2H), 7.27 (d, J=7.9 Hz, 1H), 5.36 (d, J=4.9 Hz, 2H), 5.15 (d, J=5.0 Hz, 2H); MS (EI) m/z 429 [M+H]+.

Example 12: 3-Bromo-N-(4-(1-(6-bromo-3H-imidazo[4,5-b]pyridin-2-yl)cyclobutyl)-2-chlorophenyl)benzamide (Ex. 12)

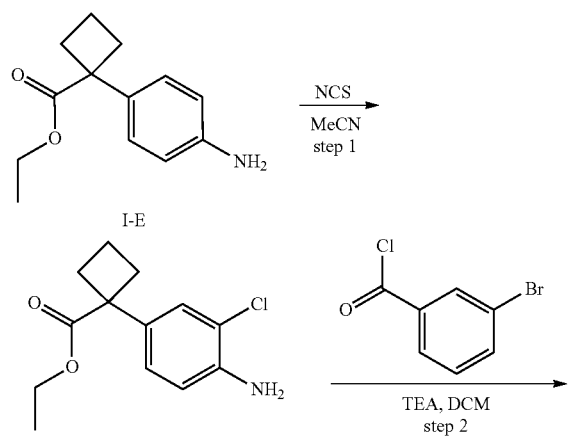

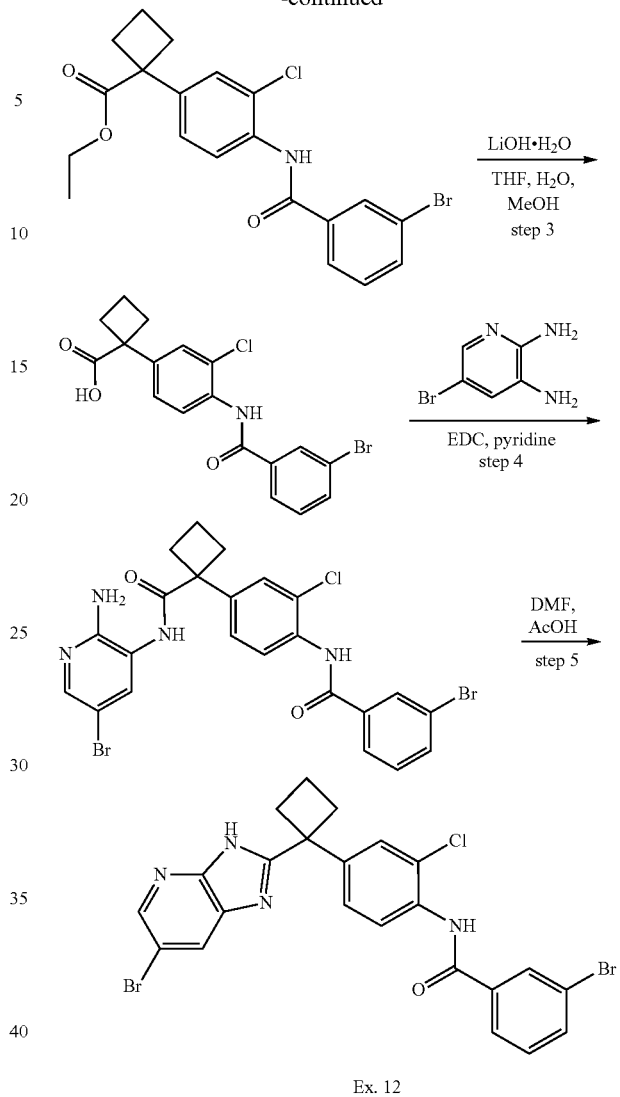

Step 1: Ethyl 1-(4-amino-3-chlorophenyl)cyclobutane-1-carboxylate

To a stirred solution of I-E (1.0 g, 4.6 mmol) in acetonitrile (20 mL) was added NCS (0.61 g, 4.6 mmol) at 0° C. After the addition was finished, the reaction was stirred at RT for 15 h. Then the solvent was removed in vacuo. The residue was diluted with water and extracted with EtOAc. The combined organic layers were washed with brine, dried over Na₂SO₄, filtered and concentrated in vacuo to afford a residue, which was purified by column chromatography on silica gel (EtOAc in petroleum ether: 0-2% gradient) to give the title compound. MS (EI) m/z 254 [M+H]+.

Step 2: Ethyl 1-(4-(3-bromobenzamido)-3-chlorophenyl)cyclobutane-1-carboxylate To a stirred solution of ethyl 1-(4-amino-3-chlorophenyl)cyclobutane-1-carboxylate (0.70 g, 2.8 mmol) in DCM (10 mL) were added TEA (1.2 mL) and the solution of 3-bromobenzoyl chloride (0.666 g, 3.03 mmol) in DCM (5 mL)

at 0° C. After the addition was finished, the reaction was stirred at 0° C. for 2 h. The mixture was diluted with water, and extracted with DCM. The combined organic layers were washed with brine, dried over Na$_2$SO$_4$, filtered and concentrated in vacuo to afford a residue, which was purified by reversed phase HPLC, eluting with water (0.2% formic acid)-ACN to give the title compound. MS (EI) m/z 436 [M+H]$^+$.

Step 3: 1-(4-(3-Bromobenzamido)-3-chlorophenyl) cyclobutanecarboxylic Acid

To a stirred solution of ethyl 1-(4-(3-bromobenzamido)-3-chlorophenyl)cyclobutanecarboxylate (0.65 g, 1.5 mmol) in THF (2 mL), MeOH (2 mL) and water (1 mL) was added lithium hydroxide hydrate (0.187 g, 4.47 mmol) at RT. The mixture was stirred at RT for 15 h. The solvent was removed in vacuo. The residue was diluted with water, adjusted to pH ~3 with 3 M HCl, extracted with EtOAc. The combined organic layers were washed with brine, dried over Na$_2$SO$_4$, filtered and concentrated in vacuo to give the title compound, which was used in the next step without further purification. MS (EI) m/z 408 [M+H]$^+$.

Step 4: N-(4-(1-((2-amino-5-bromopyridin-3-yl) carbamoyl)cyclobutyl)-2-chlorophenyl)-3-bromobenzamide To a stirred solution of 1-(4-(3-bromobenzamido)-3-chlorophenyl)cyclobutanecarboxylic acid (0.59 g, 1.4 mmol) in pyridine (5 mL) was added 5-bromopyridine-2,3-diamine (0.271 g, 1.44 mmol) and EDC (0.830 g, 4.33 mmol) at RT. After the addition was finished, the reaction was stirred at 40° C. for 15 h. The mixture was diluted with water, extracted with EtOAc. The combined organic layers were washed with brine, dried over Na$_2$SO$_4$, filtered and concentrated in vacuo to afford a residue, which was purified by reversed phase HPLC, eluting with water (0.2% formic acid)-ACN to give the title compound. MS (EI) m/z 577 [M+H]$^+$.

Step 5: 3-Bromo-N-(4-(1-(6-bromo-3H-imidazo[4,5-b]pyridin-2-yl)cyclobutyl)-2-chlorophenyl) benzamide (Ex. 12)

N-(4-(1-((2-amino-5-bromopyridin-3-yl)carbamoyl)cyclobutyl)-2-chlorophenyl)-3-bromobenzamide (420 mg, 0.726 mmol) was dissolved in DMF (4 mL) and AcOH (1 mL). The solution was heated to 130° C. for 18 h. The reaction mixture was cooled to RT, diluted with water, extracted with EtOAc. The combined organic layers were washed with brine, dried over Na$_2$SO$_4$, filtered and concentrated in vacuo to afford the title compound (Ex. 12). $^1$H NMR (400 MHz, CD$_3$OD) δ 8.44 (s, 1H), 8.12-8.11 (d, J=2.0 Hz, 2H), 7.94-7.93 (d, J=2.0 Hz, 1H), 7.77-7.76 (m, 1H), 7.71-7.69 (d, J=8.4 Hz, 1H), 7.60 (s, 1H), 7.47-7.43 (m, 2H), 3.09-3.07 (m, 2H), 2.88-2.85 (m, 2H), 2.17-2.09 (m, 2H); MS (EI) m/z 559 [M+H]$^+$.

Example 13 and Example 14: N-(2-chloro-4-(1-(6-cyano-3H-imidazo[4,5-b]pyridin-2-yl)cyclobutyl) phenyl)-3-cyanobenzamide and 3-cyano-N-(2-cyano-4-(1-(6-cyano-3H-imidazo[4,5-b]pyridin-2-yl) cyclobutyl)phenyl)benzamide (Ex. 13 and Ex. 14)

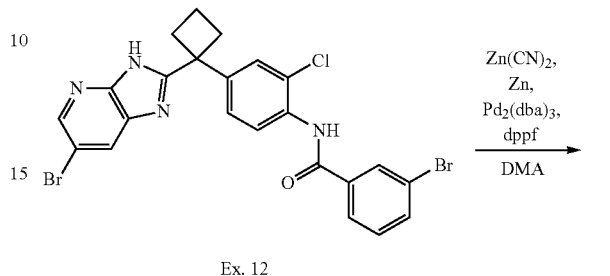

Ex. 12

Ex. 13

Ex. 14

To a stirred solution of Ex. 12 (100 mg, 0.180 mmol), Zn(CN)$_2$ (45 mg, 0.38 mmol) in DMA (2 mL) was added Zn (5.0 mg, 0.076 mmol), Pd$_2$(dba)$_3$ (5 mg, 0.005 mmol) and dppf (10 mg, 0.018 mmol). After the addition was finished, the reaction was irradiated in microwave at 120° C. for 45 min. The reaction mixture was cooled to RT, filtered and purified by reversed phase HPLC, eluting with water (0.1% TFA)-ACN to afford the title compounds as TFA salts (Ex. 13 and Ex. 14).

Example 13: $^1$H NMR (400 MHz, CD$_3$OD) δ 8.67 (s, 1H), 8.40-8.30 (m, 2H), 8.23 (d, J=7.45 Hz, 1H), 7.95 (d, J=7.45 Hz, 1H), 7.75-7.67 (m, 2H), 7.60 (s, 1H), 7.42 (d, J=8.33 Hz, 1H), 3.20-3.00 (m, 2H), 2.92-2.80 (m, 2H), 2.22-2.05 (m, 2H); MS (EI) m/z 453 [M+H]$^+$.

Example 14: $^1$H NMR (400 MHz, CD$_3$OD) δ 8.65 (s, 1H), 8.35-8.22 (m, 3H), 8.02-7.85 (m, 2H), 7.79-7.62 (m, 3H), 3.37-3.10 (m, 2H), 2.96-2.81 (m, 2H), 2.23-2.07 (m, 2H); MS (EI) m/z 444 [M+H]$^+$.

Example 15: 3-Cyano-N-(4-(1-(6-cyano-3H-imidazo[4,5-b]pyridin-2-yl)cyclobutyl)-2-methylphenyl)benzamide (Ex. 15)

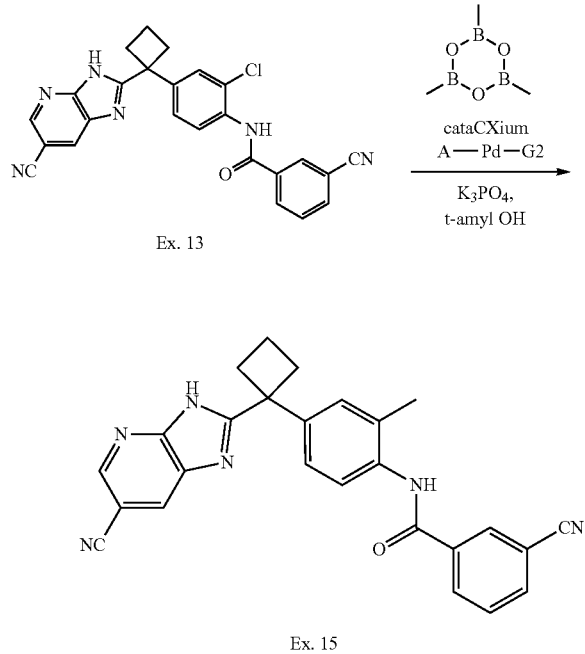

A mixture of Ex. 13 (45 mg, 0.10 mmol), 2,4,6-trimethyl-1,3,5,2,4,6-trioxatriborinane (25 mg, 0.20 mmol), 1.5 M Cs$_2$CO$_3$ (0.2 mL) and cataCXium A Pd G2 (Chloro[(di(1-adamantyl)-N-butylphosphine)-2-(2-aminobiphenyl)]palladium(II), 16 mg, 0.025 mmol) in 2-methylbutan-2-ol was stirred at 100° C. for 18 h, then the catalyst was removed by filtration. The filtrate was concentrated in vacuo. The residue was purified by reversed phase HPLC, eluting with water (0.1% TFA)-ACN to afford the title compound as a TFA salt (Ex. 15). $^1$H NMR (400 MHz, CD$_3$OD) δ 8.64 (d, J=1.3 Hz, 1H), 8.31-8.23 (m, 3H), 7.96-7.94 (m, 1H), 7.74-7.70 (m, 1H), 7.37-7.33 (m, 3H), 3.10-3.07 (m, 2H), 2.91-2.84 (m, 2H), 2.29 (s, 3H), 2.20-2.09 (m, 2H); MS (ESI) m/z: 433 [M+H]$^+$.

Example 16: N-(4-(1-(6-bromo-3H-imidazo[4,5-b]pyridin-2-yl)cyclobutyl)-2-fluorophenyl)-3-cyanobenzamide (Ex. 16)

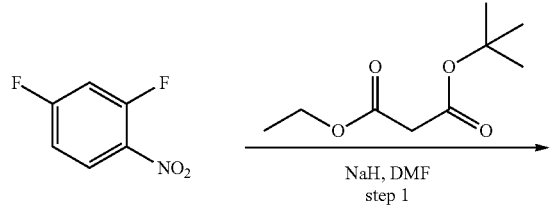

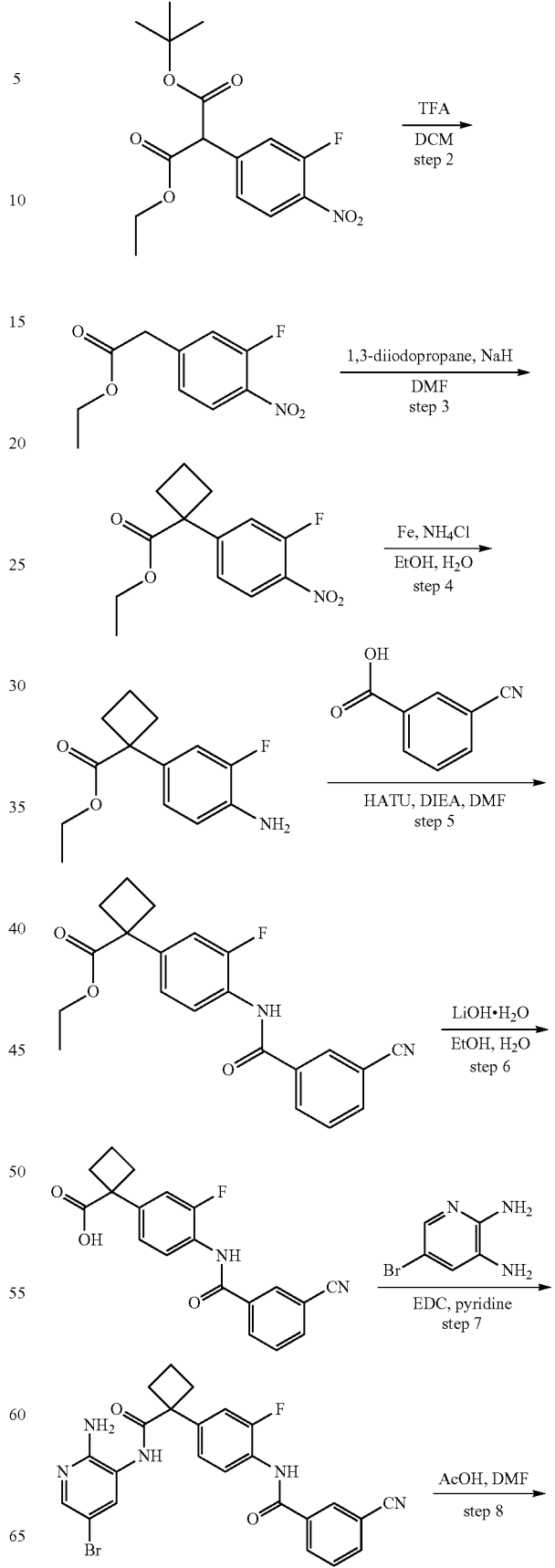

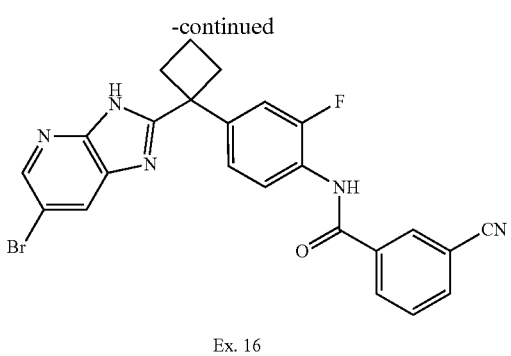

Ex. 16

Step 1: 1-(Tert-butyl) 3-ethyl 2-(3-fluoro-4-nitrophenyl)malonate

To a suspension of NaH (5.28 g, 132 mmol, 60%) in dry DMF (80 mL), tert-butyl ethyl malonate (23.66 g, 125.7 mmol) was added dropwise at 0° C. After stirring at 0° C. for 10 min, a solution of 2,4-difluoro-1-nitrobenzene (10.00 g, 62.85 mmol) in DMF (20 mL) was added dropwise. After the addition was finished, the reaction was stirred at RT for 16 h. The reaction was quenched with NH$_4$Cl (sat.), extracted with ethyl acetate. The combined organic layers were washed with brine, dried over Na$_2$SO$_4$, filtered and concentrated in vacuo to afford residue, which was purified by column chromatography on silica gel (EtOAc in petroleum ether: 0-5% gradient) to give 1-(tert-butyl) 3-ethyl 2-(3-fluoro-4-nitrophenyl)malonate (2.9 g, 14.0% yield) as an oil.

Step 2: Ethyl 2-(3-fluoro-4-nitrophenyl)acetate

To a stirred mixture of 1-(tert-butyl) 3-ethyl 2-(3-fluoro-4-nitrophenyl)malonate (2.90 g, 8.86 mmol) in DCM (30.0 mL) was added TFA (15.0 mL) in one portion at RT. After the addition was finished, the reaction mixture was stirred at 60° C. for 48 h. The mixture was cooled to RT and the solvent was removed in vacuo. The residue was re-dissolved in ethyl acetate (15.0 mL), and washed with NaHCO$_3$ (sat.), brine, dried over Na$_2$SO$_4$, filtered and concentrated in vacuo. The residue was purified by column chromatography on silica gel (EtOAc in petroleum ether: 5-10% gradient) to give the title compound.

Step 3: Ethyl 1-(3-fluoro-4-nitrophenyl)cyclobutane-1-carboxylate

To a stirred solution of ethyl 2-(3-fluoro-4-nitrophenyl)acetate (1.4 g, 6.2 mmol) in DMF (10.0 mL) was added NaH (518 mg, 13.0 mmol, 60%) at 0° C. The reaction was stirred at RT for 15 min. Then the reaction mixture was cooled to 0° C., 1,3-diiodopropane (3.65 g, 12.0 mmol) was added dropwise to the reaction mixture. After the addition was finished, the reaction mixture was stirred at RT for 1 h. The reaction was quenched with NH$_4$Cl (sat.) and extracted with ethyl acetate. The combined organic layers were washed with brine, dried over Na$_2$SO$_4$, filtered and concentrated in vacuo to afford residue, which was purified by column chromatography on silica gel (EtOAc in petroleum ether: 0-5% gradient) to give the title compound. $^1$H NMR (400 MHz, CDCl$_3$) δ 8.08-8.01 (m, 1H), 7.25-7.17 (m, 2H), 4.17-4.11 (m, 2H), 2.93-2.84 (m, 2H), 2.54-2.44 (m, 2H), 2.17-2.10 (m, 1H), 1.97-1.86 (m, 1H), 1.20 (t, J=7.24 Hz, 3H).

Step 4: Ethyl 1-(4-amino-3-fluorophenyl)cyclobutane-1-carboxylate

To a stirred suspension of ethyl 1-(3-fluoro-4-nitrophenyl)cyclobutane-1-carboxylate (800 mg, 3.00 mmol), NH$_4$Cl (1.6 g, 30 mmol) in EtOH (40 mL) and water (10 mL) was added Fe (834 mg, 15.0 mmol) at RT. The reaction mixture was stirred under reflux for 4 h. The mixture was filtered through a Celite® pad, rinsed with hot EtOH. The filtrate was concentrated in vacuo. The residue was diluted with water, and extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-20% gradient) to give the title compound. MS(EI) m/z 238 [M+H]$^+$.

Step 5: Ethyl 1-(4-(3-cyanobenzamido)-3-fluorophenyl)cyclobutane-1-carboxylate To a stirred solution of ethyl 1-(4-amino-3-fluorophenyl)cyclobutanecarboxylate (300 mg, 1.26 mmol), 3-cyanobenzoic acid (205 mg, 1.39 mmol) and DIEA (0.7 mL, 4 mmol) in DMF (1.5 mL) was added HATU (529 mg, 1.39 mmol) at RT. The reaction was stirred at RT for 2 h, then poured into water, extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-20% gradient) to give the title compound. MS (EI) m/z 367 [M+H]$^+$.

Step 6: 1-(4-(3-Cyanobenzamido)-3-fluorophenyl)cyclobutane-1-carboxylic Acid To a stirred solution of ethyl 1-(4-(3-cyanobenzamido)-3-fluorophenyl)cyclobutane carboxylate (450 mg, 1.23 mmol) in THF (1.0 mL), EtOH (1.0 mL) and water (0.5 mL) was added lithium hydroxide hydrate (258 mg, 6.14 mmol) at RT. The reaction was stirred at RT for 16 h. Then organic solvent was removed in vacuo. The aqueous solution was diluted with water, adjusted to pH~5 with 3 M HCl, extracted with EtOAc. The combined organic layers were washed with brine, dried over Na$_2$SO$_4$, filtered and concentrated in vacuo to give the crude title compound, which was used in the next step without further purification. MS (EI) m/z 339 [M+H]$^+$.

Step 7: N-(4-(1-((2-amino-5-bromopyridin-3-yl)carbamoyl)cyclobutyl)-2-fluorophenyl)-3-cyanobenzamide To a stirred solution of 1-(4-(3-cyanobenzamido)-3-fluorophenyl)cyclobutane-1-carboxylic acid (250 mg, 0.739 mmol) and 5-bromopyridine-2,3-diamine (139 mg, 0.739 mmol) in pyridine (3.0 mL) was added EDC (425 mg, 2.22 mmol) at RT. After the addition was finished, the reaction was stirred at RT for 16 h. The solvent was removed in vacuo. The residue was purified by prep-TLC (Petroleum ether:ethyl acetate=1:1 as eluent) to give the title compound. MS (EI) m/z 508 [M+H]$^+$.

Step 8: N-(4-(1-(6-bromo-3H-imidazo[4,5-b]pyridin-2-yl)cyclobutyl)-2-fluorophenyl)-3-cyanobenzamide (Ex. 16)

To a stirred solution of N-(4-(1-((2-amino-5-bromopyridin-3-yl)carbamoyl)cyclobutyl)-2-fluorophenyl)-3-cyanobenzamide (150 mg, 0.295 mmol) in DMF (4.0 mL) was added acetic acid (1.0 mL) at RT. After the addition was finished, the reaction was stirred at 130° C. for 36 h. The solvent was removed in vacuo. The residue was purified by reversed phase HPLC, eluting with water (0.1% TFA)-ACN to afford the title compound as a TFA salt (Ex. 16). $^1$H NMR (400 MHz, CDCl$_3$) δ 8.32 (t, J=8.3 Hz, 1H), 8.23 (s, 1H), 8.19 (s, 1H), 8.14 (d, J=10.9 Hz, 1H), 8.12-8.08 (m, 2H), 7.85 (d, J=7.4 Hz, 1H), 7.64 (t, J=7.8 Hz, 1H), 7.25-7.13 (m, 2H), 3.16-3.07 (m, 2H), 2.83-2.75 (m, 2H), 2.31-2.21 (m, 1H), 2.14-2.07 (m, 1H); MS (EI) m/z 490 [M+H]$^+$.

Example 17: 3-Cyano-N-(4-(1-(6-cyano-3H-imidazo[4,5-b]pyridin-2-yl)cyclobutyl)-2-fluorophenyl)benzamide (Ex. 17)

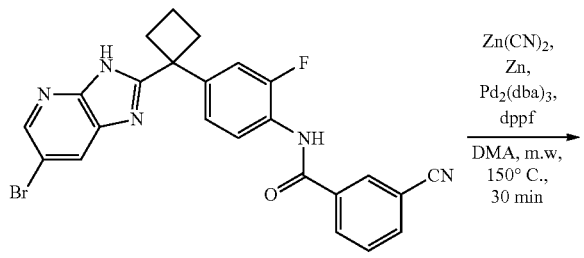

Ex. 16

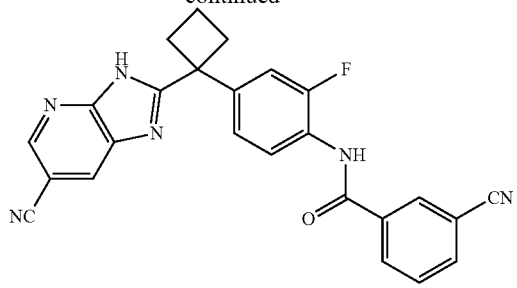

Ex. 17

To a solution of Ex. 16 (50 mg, 0.10 mmol), dppf (5.0 mg, 9.0 μmol) and zinc (2 mg, 0.03 mmol) in DMA (1.0 mL) were added dicyanozinc (10 mg, 0.085 mmol) and Pd$_2$(dba)$_3$ (3.0 mg, 3.3 μmol) at RT. After the addition was finished, the reaction mixture was irradiated at 150° C. in microwave for 45 min. The reaction mixture was cooled down to RT, poured into water and extracted with ethyl acetate. The combined organic layers were washed with brine, dried over Na$_2$SO$_4$, filtered and concentrated in vacuo to afford a residue, which was purified by reversed phase HPLC, eluting with water (0.1% TFA)-ACN to afford the title compound as a TFA salt (Ex. 17). $^1$H NMR (400 MHz, CD$_3$OD) δ 8.69 (s, 1H), 8.31 (d, J=14.5 Hz, 2H), 8.22 (d, J=7.5 Hz, 1H), 7.94 (s, 1H), 7.80-7.68 (m, 2H), 7.36-7.25 (m, 2H), 3.16-3.04 (m, 2H), 2.94-2.81 (m, 2H), 2.21-2.05 (m, 2H); MS (EI) m/z 437 [M+H]$^+$.

Examples 18-19

Examples 18-19 were made by using similar procedures for Example 16.

| Ex. # | Structure | Chemical Name | Mass [M + H]+ |
|---|---|---|---|
| 18 | ![structure] | N-{4-[1-(6-chloro-3H-imidazo[4,5-b]pyridin-2-yl)cyclobutyl]-2-fluorophenyl}-3-cyanobenzamide | Calc'd 446, found 446 |
| 19 | ![structure] | 3-cyano-N-(2-fluoro-4-{1-[6-(trifluoromethyl)-3H-imidazo[4,5-b]pyridin-2-yl]cyclobutyl}phenyl)benzamide | Calc'd 480, found 480 |

Example 20: 2-(1-(4-((1-Methyl-1H-pyrazol-3-yl)amino)-3-vinylphenyl)cyclobutyl)-3H-imidazo[4,5-b]pyridine-6-carbonitrile (Ex. 20)

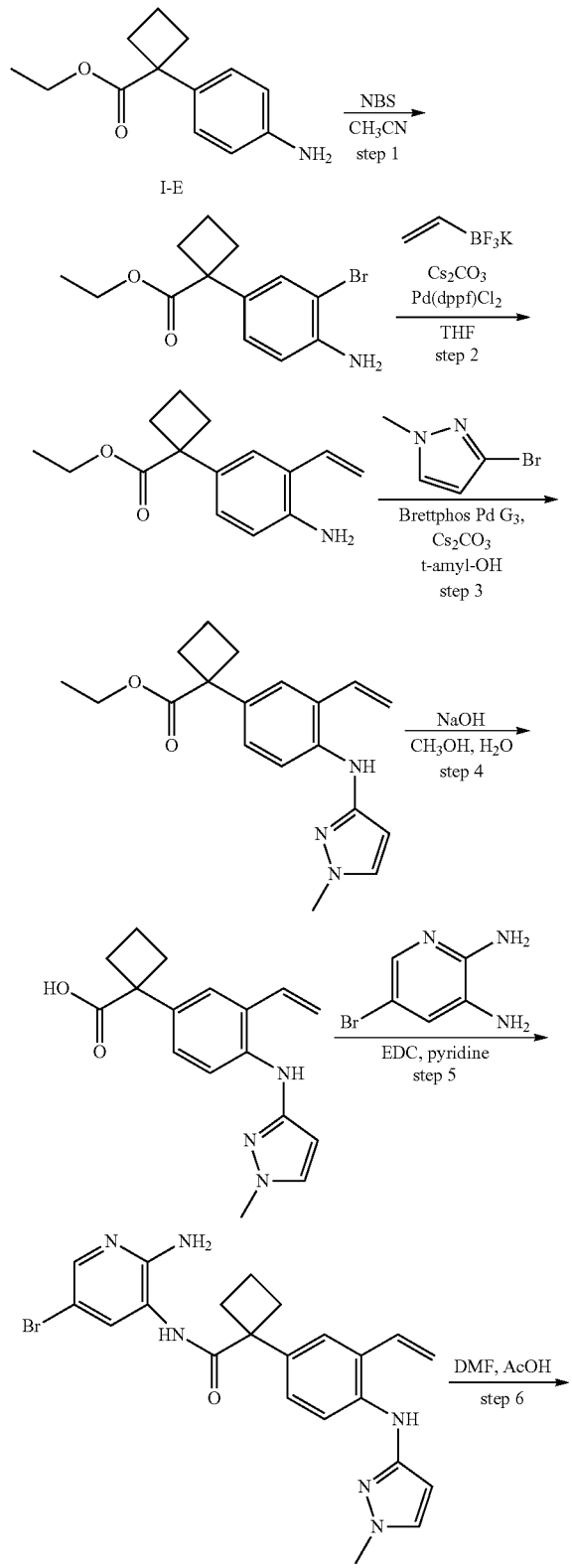

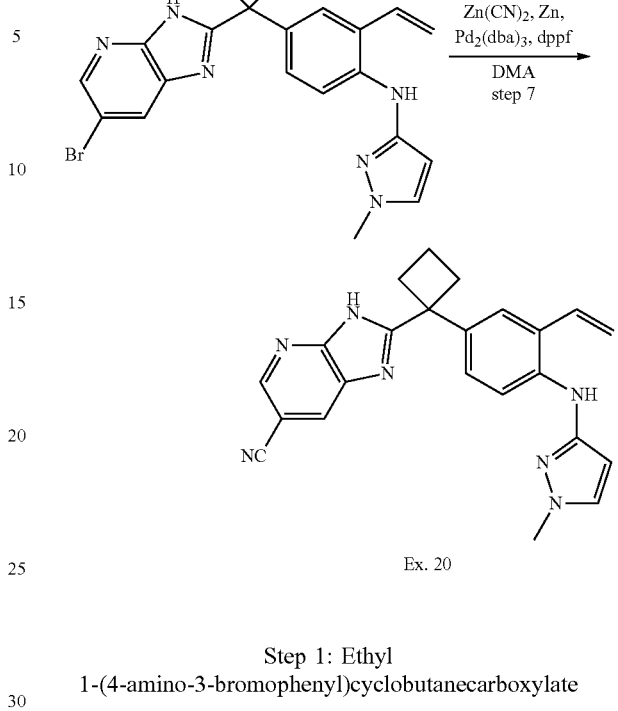

Ex. 20

Step 1: Ethyl 1-(4-amino-3-bromophenyl)cyclobutanecarboxylate

To a stirred solution of I-E (2.0 g, 9.1 mmol) in CH$_3$CN (50 mL) was added NBS (1.64 g, 9.21 mmol) at 0° C. After the addition was finished, the reaction was stirred at RT for 12 h. The reaction was quenched with Na$_2$SO$_3$ (sat.) and extracted with EtOAc. The combined organic layers were washed with brine, dried over Na$_2$SO$_4$ filtered and concentrated in vacuo to afford a residue, which was purified by column chromatography on silica gel (EtOAc/petroleum ether=1:5 as eluent) to give the title compound. MS (EI) m/z 298 [M+H]$^+$.

Step 2: Ethyl 1-(4-amino-3-vinylphenyl)cyclobutane-1-carboxylate

To a stirred solution of ethyl 1-(4-amino-3-bromophenyl)cyclobutanecarboxylate (800 mg, 2.68 mmol), potassium vinyltrifluoroborate (500 mg, 3.75 mmol) in THF (20 mL) were added Cs$_2$CO$_3$ (2800 mg, 8.810 mmol), Pd(dppf)Cl$_2$ (300 mg, 0.410 mmol) at RT. After the addition was finished, the reaction mixture was stirred at 65° C. for 16 h. The reaction mixture was cooled to RT, filtered through a Celite® and the filtrate was concentrated in vacuo. The residue was dissolved in EtOAc, washed with brine, dried over anhydrous sodium sulfate, filtered and concentrated in vacuo, and further purified by column chromatography on silica gel (EtOAc in petroleum ether: 0-30% gradient) to give the title compound. MS (EI) m/z 246 [M+H]$^+$.

Step 3: Ethyl 1-(4-((1-methyl-1H-pyrazol-3-yl)amino)-3-vinylphenyl)cyclobutane-1-carboxylate To the mixture of 3-bromo-1-methyl-1H-pyrazole (236 mg, 1.47 mmol), ethyl 1-(4-amino-3-vinylphenyl) cyclobutanecarboxylate (540 mg, 2.20 mmol), Cs$_2$CO$_3$ (1410 mg, 4.41 mmol) in t-amyl alcohol (5 mL) was added Brettphos Pd G3 ([(2-di-cyclohexylphosphino-3,6-dimethoxy-2',4',6'- triisopropyl-1,1'-biphenyl)-2-(2'-amino-1,1'-biphenyl)]palladium(II) methanesulfonate methanesulfonate, 120 mg, 0.130 mmol) under nitrogen atmosphere at RT. After the addition was finished, the reaction mixture was stirred at 105° C. for 16 h. The reaction mixture was cooled to RT and diluted with EtOAc, washed with brine. The organic phase was dried over anhydrous sodium sulfate, filtered and concentrated in vacuo. The residue was purified by column chromatography on silica gel (EtOAc in petroleum ether: 0-30% gradient) to give the title compound. MS (EI) m/z 326 [M+H]$^+$.

Step 4: 1-(4-((1-Methyl-1H-pyrazol-3-yl)amino)-3-vinylphenyl)cyclobutane-1-carboxylic Acid To a stirred solution of ethyl 1-(4-((1-methyl-1H-pyrazol-3-yl)amino)-3-vinylphenyl) cyclobutanecarboxylate (180 mg, 0.550 mmol in MeOH (3 mL), water (1 mL) was added NaOH (177 mg, 4.43 mmol) at RT. The reaction was stirred at RT for 16 h. The solvent was removed in vacuo. The residue was dissolved in water, and adjusted the pH to ~3 with 1M HCl, extracted with EtOAc. The combined organic layers were washed with brine, dried over Na$_2$SO$_4$, filtered and concentrated in vacuo to give the title compound, which was used directly in the next step without further purification. MS (EI) m/z 298 [M+H]$^+$.

Step 5: N-(2-amino-5-bromopyridin-3-yl)-1-(4-((1-methyl-1H-pyrazol-3-yl)amino)-3-vinylphenyl)cyclobutane-1-carboxamide To a stirred solution of 1-(4-((1-methyl-1H-pyrazol-3-yl)amino)-3-vinylphenyl) cyclobutanecarboxylic acid (110 mg, 0.370 mmol), 5-bromopyridine-2,3-diamine (174 mg, 0.925 mmol) in pyridine (4 mL) was added EDC (177 mg, 0.925 mmol) at RT. The reaction was stirred at RT for 12 h. The solvent was removed in vacuo and the residue was purified by pre-TLC (Petroleum ether/EtOAc=1:1) to give the title compound. MS (EI) m/z 467 [M+H]$^+$.

Step 6: N-(4-(1-(6-bromo-3H-imidazo[4,5-b]pyridin-2-yl)cyclobutyl)-2-vinylphenyl)-1-methyl-1H-pyrazol-3-amine To a stirred solution of N-(2-amino-5-bromopyridin-3-yl)-1-(4-((1-methyl-1H-pyrazol-3-yl)amino)-3-vinylphenyl) cyclobutanecarboxamide (100 mg, 0.214 mmol) in DMF (4 mL) was added acetic acid (1 mL) at RT. After the addition was finished, the reaction was stirred at 130° C. for 16 h. The solvent was removed in vacuo. The residue was diluted with water, adjusted pH to ~8 with NaHCO$_3$ (sat.), and extracted with EtOAc. The combined organic layers were washed with brine, dried over Na$_2$SO$_4$, filtered and concentrated in vacuo to give the title compound, which was used in the next step without further purification. MS (EI) m/z 449 [M+H]$^+$.

Step 7: 2-(1-(4-((1-Methyl-1H-pyrazol-3-yl)amino)-3-vinylphenyl)cyclobutyl)-3H-imidazo[4,5-b]pyridine-6-carbonitrile (Ex. 20)

To the mixture of dicyanozinc (25 mg, 0.21 mmol), zinc (20 mg, 0.31 mmol), Pd$_2$(dba)$_3$ (9.0 mg, 9.8 µmol), dppf (27 mg, 0.049 mmol) in DMA (0.5 mL) was added N-(4-(1-(6-bromo-3H-imidazo[4,5-b]pyridin-2-yl)cyclobutyl)-2-vinylphenyl)-1-methyl-1H-pyrazol-3-amine (20 mg, 0.045 mmol) at RT. After the addition was finished, the reaction was irradiated in microwave at 150° C. for 45 min. The reaction mixture was cooled to RT and filtered. The filtrate was concentrated in vacuo to afford a residue, which was purified by reversed phase HPLC, eluting with water (0.1% TFA)-ACN to afford the title compound as a TFA salt (Ex. 20). $^1$H NMR (400 MHz, CD$_3$OD) δ 8.65 (d, J=1.8 Hz, 1H), 8.26 (d, J=1.8 Hz, 1H), 7.53 (d, J=2.2 Hz, 1H), 7.47 (d, J=2.6 Hz, 1H), 7.34 (d, J=8.4 Hz, 1H), 7.24 (dd, J=8.4, 2.2 Hz, 1H), 6.84-7.07 (m, 1H), 5.85 (d, J=2.6 Hz, 1H), 5.71 (dd, J=17.6, 1.4 Hz, 1H), 5.30 (d, J=12.2 Hz, 1H), 3.74 (s, 3H), 3.12-3.01 (m, 2H), 2.90-2.80 (m, 2H), 2.17-2.03 (m, 2H). MS (EI) m/z 396 [M+H]$^+$.

Example 21: 2-(1-(3-(Hydroxymethyl)-4-((1-methyl-1H-pyrazol-3-yl)amino)phenyl)cyclobutyl)-3H-imidazo[4,5-b]pyridine-6-carbonitrile (Ex. 21)

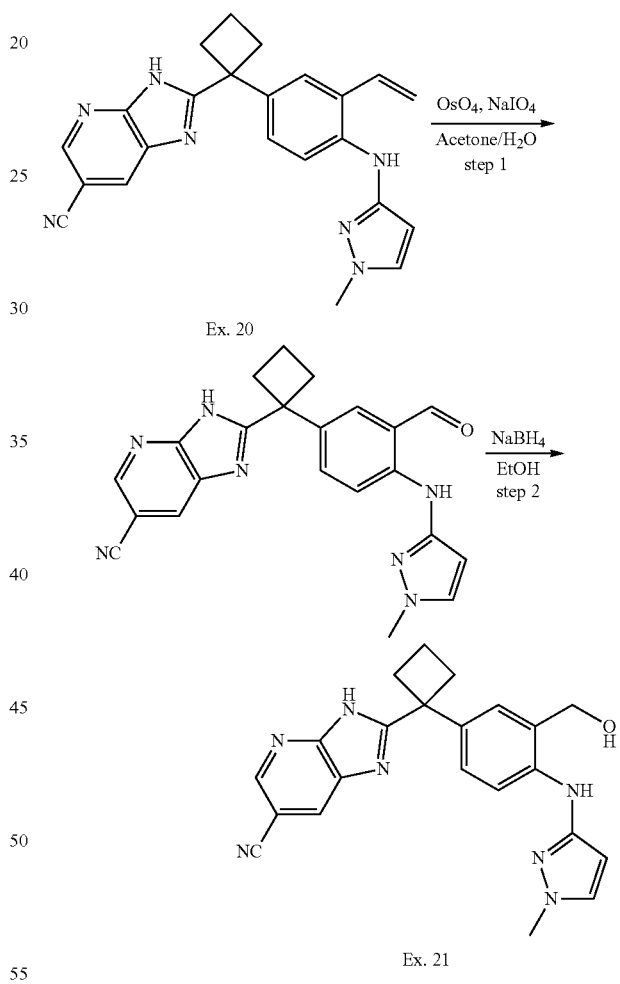

Ex. 21

Step 1: 2-(1-(3-Formyl-4-((1-methyl-1H-pyrazol-3-yl)amino)phenyl)cyclobutyl)-3H-imidazo[4,5-b]pyridine-6-carbonitrile To a stirred solution of Ex. 20 (30 mg, 0.076 mmol) in acetone (4 mL), water (2 mL) was added OsO$_4$ (4.0 µl, 7.6 µmol) at 0° C. The reaction was stirred at 0° C. for 15 min, followed by the addition of NaIO$_4$ (48.7 mg, 0.228 mmol) at 0° C. After the addition was finished, the reaction was stirred at RT for 45 min. The reaction was quenched with Na$_2$SO$_3$ (sat.), and extracted with DCM. The combined organic layers were washed with brine, dried over Na₂SO₄, filtered and concentrated in vacuo to give the title compound, which was used in the next step without further purification. MS (ESI) m/z: 398 [M+H]⁺.

Step 2: 2-(1-(3-(Hydroxymethyl)-4-((1-methyl-1H-pyrazol-3-yl)amino)phenyl)cyclobutyl)-3H-imidazo[4,5-b]pyridine-6-carbonitrile (Ex. 21)

To a stirred solution of 2-(1-(3-formyl-4-((1-methyl-1H-pyrazol-3-yl)amino)phenyl)cyclobutyl)-3H-imidazo[4,5-b]pyridine-6-carbonitrile (25 mg, 0.063 mmol) in ethanol (2 mL) was added NaBH₄ (5.0 mg, 0.13 mmol) at 0° C. After the addition was finished, the reaction was stirred at RT for 30 min. The reaction mixture was diluted with DCM and the organic layer was washed with brine, dried over anhydrous sodium sulfate, filtered and concentrated in vacuo to afford a residue, which was purified by by reversed phase HPLC, eluting with water (0.1% TFA)-ACN to afford the title compound as a TFA salt (Ex. 21). ¹H NMR (400 MHz, CD₃OD) δ 8.61 (d, J=1.4 Hz, 1H), 8.22 (s, 1H), 7.50-7.35 (m, 2H), 7.29-7.19 (m, 2H), 5.91 (d, J=2.4 Hz, 1H), 4.62 (s, 2H), 3.75 (s, 3H), 3.25-2.95 (m, 2H), 2.90-2.71 (m, 2H), 2.12-1.95 (m, 2H). MS (EI) m/z 400 [M+H]⁺.

Example 22: Cyclopropyl (4-(1-(6-cyano-3H-imidazo[4,5-b]pyridin-2-yl)cyclobutyl)phenyl)carbamate (Ex. 22)

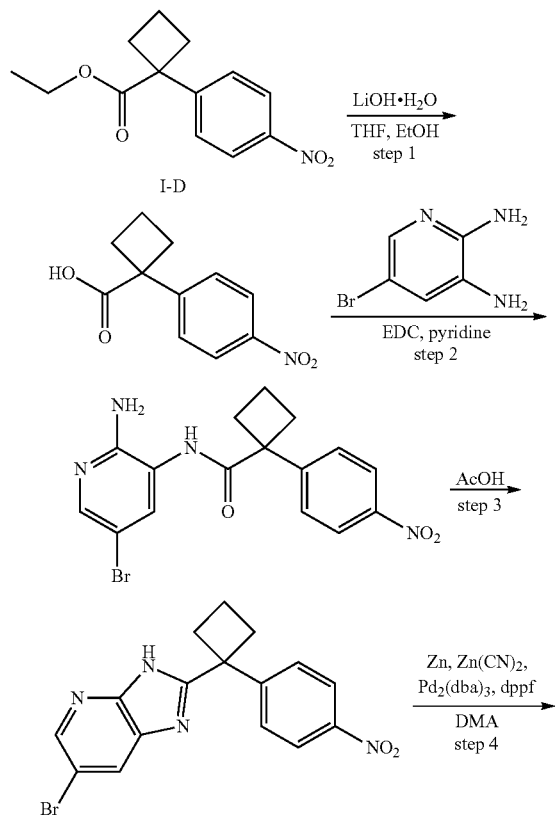

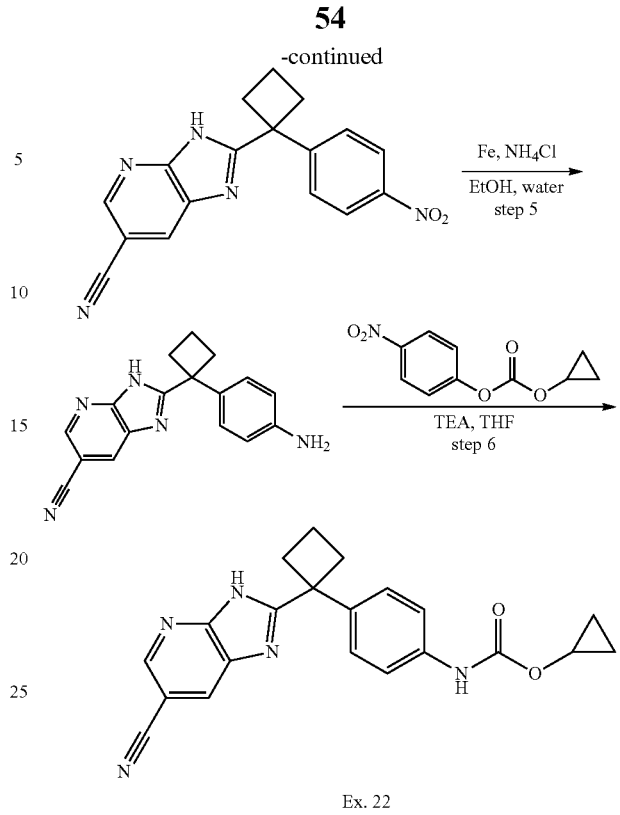

Ex. 22

Step 1: 1-(4-Nitrophenyl)cyclobutane-1-carboxylic Acid

To a stirred solution of I-D (5.0 g, 20 mmol) in THF (1.0 mL), EtOH (1.0 mL) and water (0.5 mL) was added LiOH (2.40 g, 100 mmol) at RT. The reaction was stirred at RT for 20 h. The solvent was removed in vacuo. The residue was diluted with water, adjusted to pH ~4 with 6 N HCl, and extracted with ethyl acetate. The combined organic layers were washed with brine, dried over Na₂SO₄, filtered and concentrated in vacuo to give the crude title compound (4.0 g, 18.08 mmol) as a solid, which was used in the next step without further purification.

Step 2: N-(2-amino-5-bromopyridin-3-yl)-1-(4-nitrophenyl)cyclobutane-1-carboxamide To a stirred solution of 1-(4-nitrophenyl)cyclobutanecarboxylic acid (1.0 g, 4.52 mmol) in pyridine (10.0 mL) were added EDC (2.60 g, 13.6 mmol) and 5-bromopyridine-2,3-diamine (0.90 g, 4.8 mmol) at RT. The mixture was stirred at RT for 3 h. The solvent was removed in vacuo. The residue was diluted with water, extracted with ethyl acetate. The combined organic layers were washed with brine, dried over Na₂SO₄, filtered and concentrated in vacuo to afford a residue, which was purified by column chromatography on silica gel (EtOAc in petroleum ether: 0-50% gradient) to give the title compound. MS (EI) m/z 391 [M+H]⁺.

Step 3: 6-Bromo-2-(1-(4-nitrophenyl)cyclobutyl)-3H-imidazo[4,5-b]pyridine

A mixture of N-(2-amino-5-bromopyridin-3-yl)-1-(4-nitrophenyl)cyclobutanecarboxamide (480 mg, 1.23 mmol) and acetic acid (10.0 mL) was stirred at 130° C. for 8 h. The solvent was removed in vacuo. Ethyl acetate (10.0 mL) and petroleum ether (5.0 mL) were added to the residue. After stirring at RT for 1 h, some solid was precipitated out. The solid was collected and washed with a solution (ethyl acetate/petroleum ether=1/1), dried in vacuo to give the title compound. MS (EI) m/z 373 [M+H]+.

Step 4: 2-(1-(4-Nitrophenyl)cyclobutyl)-3H-imidazo [4,5-b]pyridine-6-carbonitrile To a solution of 6-bromo-2-(1-(4-nitrophenyl)cyclobutyl)-3H-imidazo[4,5-b]pyridine (280 mg, 0.750 mmol), dppf (35 mg, 0.063 mmol) and zinc (10 mg, 0.15 mmol) in DMA (5.0 mL) were added dicyanozinc (176 mg, 1.50 mmol) and Pd$_2$(dba)$_3$ (20 mg, 0.022 mmol) at RT. After the addition was finished, the reaction mixture was irradiated in microwave at 150° C. for 45 min. The reaction was cooled to RT, diluted with water and extracted with ethyl acetate. The combined organic layers were washed with brine, dried over Na$_2$SO$_4$, filtered and concentrated in vacuo to afford a residue, which was purified by column chromatography on silica gel (EtOAc in petroleum ether: 0-5% gradient) to give the title compound. MS (EI) m/z 320 [M+H]+.

Step 5: 2-(1-(4-Aminophenyl)cyclobutyl)-3H-imidazo[4,5-b]pyridine-6-carbonitrile To a stirred solution of 2-(1-(4-nitrophenyl)cyclobutyl)-3H-imidazo[4,5-b]pyridine-6-carbonitrile (180 mg, 0.564 mmol) and NH$_4$Cl (302 mg, 5.64 mmol) in ethanol (20.0 mL) and water (5 mL) was added iron (157 mg, 2.82 mmol) at RT. After the addition was finished, the reaction was stirred at 80° C. for 16 h. The reaction mixture was filtered. The filtrate was concentrated in vacuo to afford a residue, which was purified by prep-TLC (petroleum ether/ethyl acetate=1:1 as eluent) to give the title compound. MS (ESI) m/z 290 [M+H]+.

Step 6: Cyclopropyl (4-(1-(6-cyano-3H-imidazo[4, 5-b]pyridin-2-yl)cyclobutyl)phenyl)carbamate (Ex. 22)

To a stirred solution of 2-(1-(4-aminophenyl)cyclobutyl)-3H-imidazo[4,5-b]pyridine-6-carbonitrile (30 mg, 0.10 mmol) and TEA (105 mg, 1.03 mmol) in THF (5.0 ml) was added cyclopropyl (4-nitrophenyl) carbonate (35 mg, 0.16 mmol) at 0° C. After the addition was finished, the reaction was stirred at 50° C. for 20 h. Then the solvent was removed in vacuo. The residue was purified by prep-TLC (petroleum ether/ethyl acetate=1:1 as eluent) to give crude product, which was re-purified by reversed phase HPLC, eluting with water (0.2% formic acid)-ACN to afford the title compound as a TFA salt (Ex. 22). $^1$H NMR (400 MHz, CDCl$_3$) δ 8.47 (s, 1H), 8.26 (s, 1H), 7.44 (d, J=8.3 Hz, 2H), 7.33 (d, J=8.8 Hz, 2H), 6.65 (s, 1H), 4.16 (t, J=4.6 Hz, 1H), 3.19-2.97 (m, 2H), 2.90-2.72 (m, 2H), 2.40-2.25 (m, 1H), 2.12-2.04 (m, 1H), 0.80-0.66 (m, 4H); MS (EI) m/z 374 [M+H]+.

Example 23: N-(4-(1-(6-chloro-1H-benzo[d]imidazol-2-yl)-3-hydroxycyclobutyl)phenyl)-3-cyanobenzamide (Ex. 23)

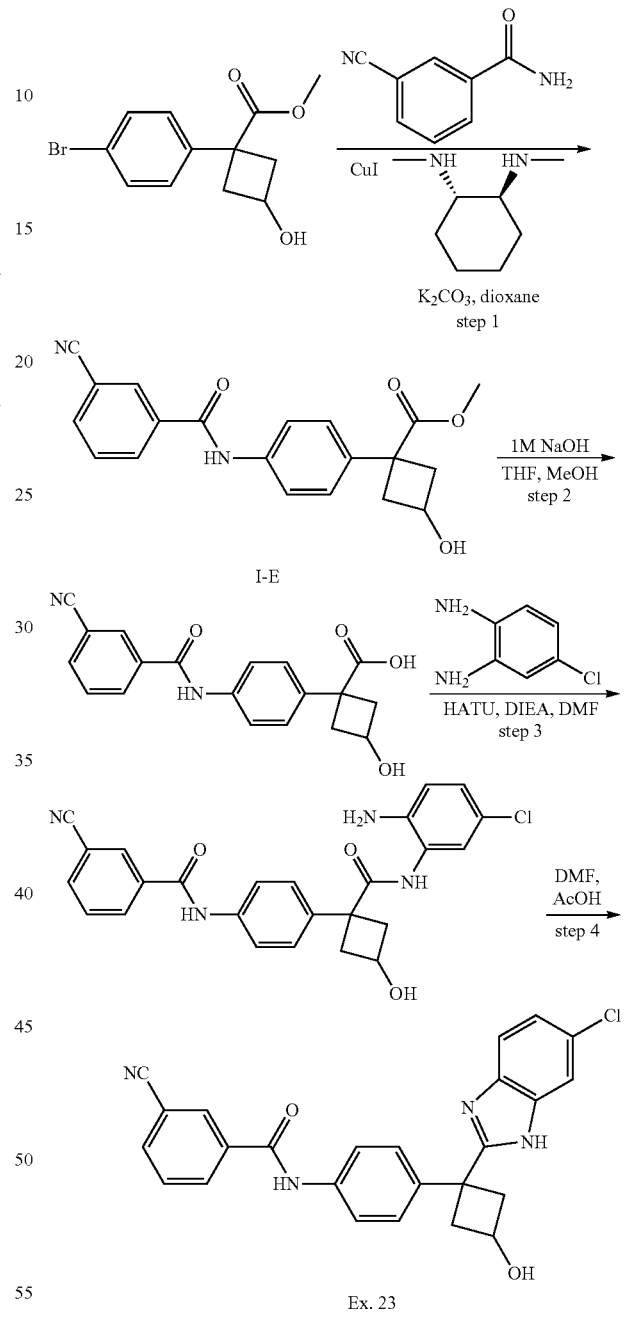

Step 1: Methyl 1-(4-(3-cyanobenzamido)phenyl)-3-hydroxycyclobutane-1-carboxylate To a vial were added methyl 1-(4-bromophenyl)-3-hydroxycyclobutanecarboxylate (335.8 mg, 1.178 mmol), 3-cyanobenzamide (258 mg, 1.77 mmol), copper(I) iodide (40.4 mg, 0.212 mmol), (1S,2S)—N1,N2-dimethylcyclohexane-1,2-diamine (80 mg, 0.56 mmol), K$_2$CO$_3$ (331 mg, 2.39 mmol) and dioxane (6 mL). The mixture was evacuated and backfilled with $N_2$ for 4 times, then heated at 120° C. for 17 h. The mixture was diluted with water and EtOAc. After extraction, the combined organic layers were washed with brine, dried over $Na_2SO_4$, filtered and concentrated in vacuo to afford a residue, which was purified by column chromatography on silica gel (EtOAc in hexane: 0-100% gradient) to afford the title compound. MS (EI) m/z 373 [M+Na]+.

Step 2: 1-(4-(3-Cyanobenzamido)phenyl)-3-hydroxycyclobutane-1-carboxylic Acid

To a vial containing methyl 1-(4-(3-cyanobenzamido)phenyl)-3-hydroxycyclobutanecarboxylate (173 mg, 0.494 mmol) were added THF (3 mL), MeOH (1.5 mL) and NaOH (1M, 0.7 mmol, 0.7 mL). The mixture was stirred at RT for 20 h. The solvent was removed in vacuo. The residue was diluted with water and adjusted to pH~3 with HCl (1M). Some solid was precipitated out, which was the desired product. Filtration afforded the title compound. MS (EI) m/z 337 [M+H]+.

Step 3: N-(4-(1-((2-amino-5-chlorophenyl)carbamoyl)-3-hydroxycyclobutyl)phenyl)-3-cyanobenzamide To a flask were added 1-(4-(3-cyanobenzamido)phenyl)-3-hydroxycyclobutanecarboxylic acid (153 mg, 0.455 mmol), 4-chlorobenzene-1,2-diamine (130 mg, 0.910 mmol), HATU (346 mg, 0.910 mmol), DMF (4.5 mL) and DIEA (250 µl, 1.43 mmol). The mixture was stirred at RT for 20 h. The solvent was evaporated in vacuo. The residue was purified by column chromatography on silica gel (MeOH in DCM: 0-10% gradient) to afford the title compound. MS (EI) m/z 461 [M+H]+.

Step 4: N-(4-(1-(6-chloro-1H-benzo[d]imidazol-2-yl)-3-hydroxycyclobutyl)phenyl)-3-cyanobenzamide (Ex. 23)

To a vial containing N-(4-(1-((2-amino-5-chlorophenyl)carbamoyl)-3-hydroxycyclobutyl)phenyl)-3-cyanobenzamide (210 mg, 0.456 mmol) were added DMF (2400 µl) and acetic acid (600 µl). The mixture was irradiated in microwave at 150° C. for 2 h. The mixture was filtered and purified by reversed phase HPLC, eluting with water (0.1% TFA)-ACN to afford the title compound as a TFA salt (Ex. 23). $^1$H NMR (499 MHz, DMSO-$d_6$) δ 10.48 (s, 1H), 8.39 (s, 1H), 8.24 (d, J=7.7 Hz, 1H), 8.08 (d, J=7.6 Hz, 1H), 7.86-7.64 (m, 4H), 7.61 (d, J=8.5 Hz, 1H), 7.50 (d, J=8.4 Hz, 2H), 7.36 (d, J=8.0 Hz, 1H), 4.13 (dd, J=14.1, 7.0 Hz, 1H), 3.13 (s, 2H), 2.92-2.74 (m, 2H); MS (EI) m/z 443 [M+H]+.

Example 24: 3-Chloro-N-(4-(1-(6-chloro-1H-imidazo[4,5-b]pyridin-2-yl)-3,3-difluorocyclobutyl)phenyl)benzamide (Ex. 24)

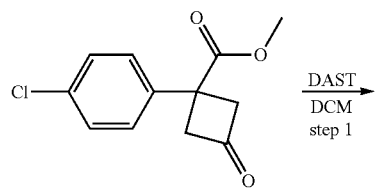

Step 1: Methyl 1-(4-chlorophenyl)-3,3-difluorocyclobutane-1-carboxylate

To a solution of methyl 1-(4-chlorophenyl)-3-oxocyclobutanecarboxylate (800 mg, 3.35 mmol) in DCM (21 mL), was added a solution of DAST (1.3 ml, 9.8 mmol) in DCM (8 mL) at 0° C. The mixture was warmed to RT and stirred at RT for 16 h. The mixture was quenched with NaHCO$_3$ (sat.) and extracted with DCM. The combined organic layers were washed with brine, dried over Na$_2$SO$_4$, filtered and concentrated in vacuo to afford residue, which was purified by column chromatography on silica gel (EtOAc in hexane: 0-10% gradient) to afford the title compound. $^1$H NMR (600 MHz, Chloroform-d) δ 7.32 (d, J=8.3 Hz, 2H), 7.22 (d, J=8.3 Hz, 2H), 3.67 (s, 3H), 3.54-3.34 (m, 2H), 3.00 (q, J=13.7 Hz, 2H).

Step 2: Methyl 1-(4-aminophenyl)-3,3-difluorocyclobutane-1-carboxylate

To a vial were added methyl 1-(4-chlorophenyl)-3,3-difluorocyclobutanecarboxylate (285 mg, 1.09 mmol), Pd$_2$(dba)$_3$ (120 mg, 0.131 mmol), and toluene (5000 μl). The mixture was evacuated and back filled with N$_2$ for 3 times. Then tri-tert-butylphosphane, 10% weight in hexane (265 mg, 0.131 mmol) and LiHMDS (1500 μl, 1.500 mmol) were added. The mixture was evacuated and back filled with N$_2$ for 3 times. The resulting solution was stirred at RT for 17 h. The mixture was diluted with Et$_2$O, and the silylamide was deprotected by adding 1 drop of 1 N HCl. The mixture was transferred to a separatory funnel and washed with 1N NaOH. The organic layer was washed with brine, dried over Na$_2$SO$_4$, filtered and concentrated in vacuo to afford a residue, which was purified by column chromatography on silica gel (EtOAc in hexane: 0-50% gradient) to afford the title compound. MS (EI) m/z 242 [M+H]$^+$.

Step 3: Methyl 1-(4-(3-chlorobenzamido)phenyl)-3,3-difluorocyclobutane-1-carboxylate Methyl 1-(4-aminophenyl)-3,3-difluorocyclobutanecarboxylate (28.8 mg, 0.119 mmol) was dissolved into DCM (1000 μl) and cooled to 0° C. using an ice bath. Et$_3$N (50 μl, 0.36 mmol) and 3-chlorobenzoyl chloride (22.9 μl, 0.179 mmol) were added to the solution dropwise at 0° C. The mixture was stirred at RT for 18 h. The mixture was purified by column chromatography on silica gel (EtOAc in hexane: 0-20% gradient) to afford the title compound. MS (EI) m/z 380 [M+H]$^+$.

Step 4: 1-(4-(3-Chlorobenzamido)phenyl)-3,3-difluorocyclobutane-1-carboxylic Acid To the vial containing methyl 1-(4-(3-chlorobenzamido)phenyl)-3,3-difluorocyclobutanecarboxylate (36 mg, 0.094 mmol) were added MeOH (200 μl), THF (600 μl) and NaOH (1M, 150 μl, 0.150 mmol). The mixture was stirred at RT for 17 h. The organic solvent was removed in vacuo. The aqueous solution was adjusted to pH~3 with 1M HCl. Some solid precipitated out, which is the desired product. Filtration afforded the title compound. MS (EI) m/z 366 [M+H]$^+$.

Step 5: N-(4-(1-((2-amino-5-chloropyridin-3-yl)carbamoyl)-3,3-difluorocyclobutyl)phenyl)-3-chlorobenzamide To a vial were added 1-(4-(3-chlorobenzamido)phenyl)-3,3-difluorocyclobutanecarboxylic acid (30 mg, 0.083 mmol), 5-chloropyridine-2,3-diamine (17.8 mg, 0.124 mmol), HATU (63.0 mg, 0.166 mmol), DMF (600 μl) and DIEA (60 μl, 0.34 mmol). The mixture was stirred at RT for 20 h. The solvent was removed in vacuo to afford a residue, which was purified by column chromatography on silica gel (EtOAc in hexane: 0-70% gradient) to afford the title compound. MS (EI) m/z 491 [M+H]$^+$.

Step 6: 3-Chloro-N-(4-(1-(6-chloro-1H-imidazo[4,5-b]pyridin-2-yl)-3,3-difluorocyclobutyl)phenyl)benzamide (Ex. 24)

To a vial containing N-(4-(1-((2-amino-5-chloropyridin-3-yl)carbamoyl)-3,3-difluorocyclobutyl)phenyl)-3-chlorobenzamide (41 mg, 0.083 mmol) were added DMF (400 μl) and acetic acid (100 μl). The mixture was irradiated in microwave at 150° C. for 3 h. The mixture was filtered and purified by reversed phase HPLC, eluting with water (0.1% TFA)-ACN to afford the title compound as a TFA salt (Ex. 24). $^1$H NMR (600 MHz, DMSO-d$_6$) δ 10.34 (s, 1H), 8.28 (s, 1H), 8.05 (s, 1H), 7.94 (s, 1H), 7.85 (d, J=7.7 Hz, 1H), 7.72 (d, J=8.4 Hz, 2H), 7.62 (d, J=7.8 Hz, 1H), 7.52 (t, J=7.8 Hz, 1H), 7.40 (d, J=8.4 Hz, 2H), 3.69 (q, J=12.9 Hz, 2H), 3.37 (q, J=13.3 Hz, 2H). MS (EI) m/z 473 [M+H]$^+$.

Example 25: N-(4-(1-(6-chloro-1H-benzo[d]imidazol-2-yl)-3-fluorocyclobutyl)phenyl)-3-cyanobenzamide (Ex. 25)

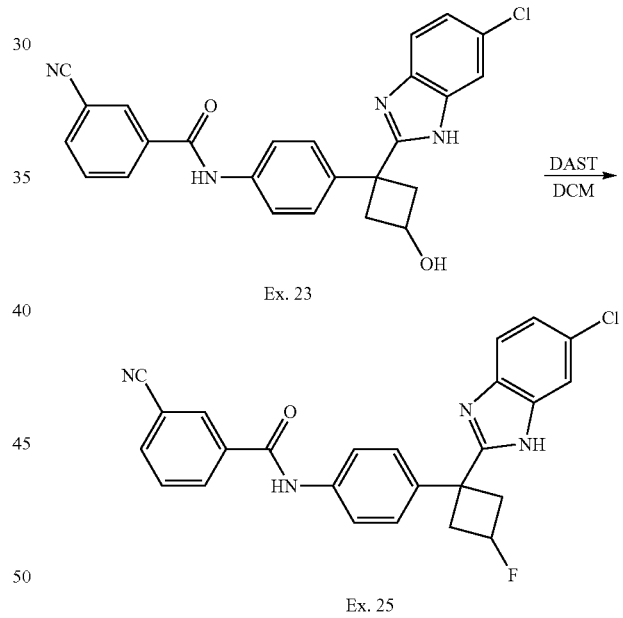

To the solution of Ex. 23 (16 mg, 0.028 mmol) in DCM (500 μl) at −78° C. was added DAST (10 μl, 0.076 mmol). The mixture was stirred at −78° C. for 2 h. The reaction was quenched with NaHCO$_3$ (sat.) and diluted with DCM. The organic layer was washed with brine, dried over Na$_2$SO$_4$, filtered and concentrated in vacuo to afford a residue, which was purified by column chromatography on silica gel (EtOAc in hexane: 0-50% gradient) to afford the title compound as a TFA salt (Ex. 25). $^1$H NMR (600 MHz, DMSO-d$_6$) δ 10.42 (s, 1H), 8.35 (s, 1H), 8.20 (d, J=7.8 Hz, 1H), 8.03 (d, J=7.6 Hz, 1H), 7.81-7.64 (m, 3H), 7.57 (s, 1H), 7.51 (d, J=8.5 Hz, 1H), 7.31 (d, J=8.3 Hz, 2H), 7.21 (d, J=8.4 Hz, 1H), 5.18 (dt, J=55.8, 6.7 Hz, 1H), 3.59-3.36 (m, 2H), 2.93-2.72 (m, 2H); MS (EI) m/z 445 [M+H]$^+$.

Example 26: 3-Cyano-N-(4-(1-(6-cyano-1H-benzo[d]imidazol-2-yl)-3-fluorocyclobutyl)phenyl)benzamide (Ex. 26)

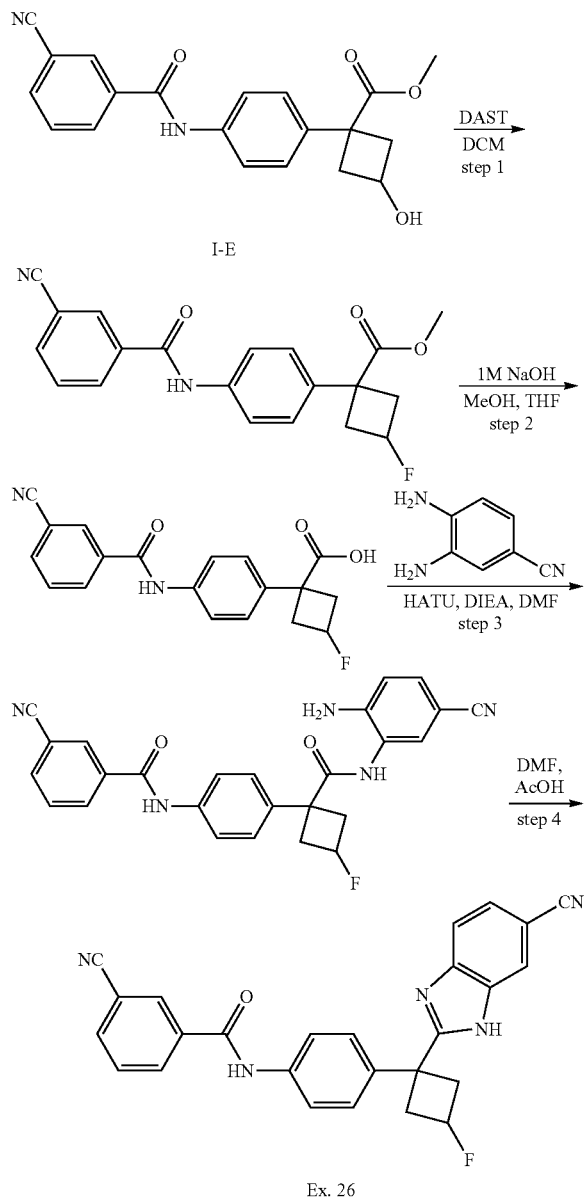

Step 1: Methyl 1-(4-(3-cyanobenzamido)phenyl)-3-fluorocyclobutane-1-carboxylate A solution of I-E (518.7 mg, 1.480 mmol) in DCM (10 ml) was treated with solution of DAST (597 mg, 3.70 mmol) in DCM (1 ml) at −78° C. The reaction was stirred at −78° C. for 1.5 h, then quenched with NaHCO$_3$ (sat.) and diluted with DCM. The organic layer was dried over Na$_2$SO$_4$, filtered and concentrated in vacuo to afford a residue, which was purified by column chromatography on silica gel (EtOAc in hexane: 0-50% gradient) to afford the title compound. MS (EI) m/z 353 [M+H]$^+$.

Step 2: 1-(4-(3-Cyanobenzamido)phenyl)-3-fluorocyclobutane-1-carboxylic Acid To a vial containing methyl 1-(4-(3-cyanobenzamido)phenyl)-3-fluorocyclobutanecarboxylate (312 mg, 0.885 mmol) were added THF (6 mL), MeOH (2 mL) and NaOH (1M, 1.3 mL, 1.3 mmol) The mixture was stirred at RT for 18 h. The organic solvent was evaporated in vacuo. The aqueous solution was adjusted to pH ~3 by HCl (1M). Some solid precipitated out, which was the desired product. After filtration, the reaction afforded the title compound. MS (EI) m/z 339 [M+H]$^+$.

Step 3: N-(4-(1-((2-amino-5-cyanophenyl)carbamoyl)-3-fluorocyclobutyl)phenyl)-3-cyanobenzamide To a flask were added 1-(4-(3-cyanobenzamido)phenyl)-3-fluorocyclobutanecarboxylic acid (60 mg, 0.18 mmol), 3,4-diaminobenzonitrile (47.2 mg, 0.355 mmol), HATU (135 mg, 0.355 mmol), DMF (1500 µL) and DIEA (100 µL, 0.573 mmol). The mixture was stirred at RT for 18 h. The solvent was removed in vacuo to afford a residue, which was purified by column chromatography on silica gel (EtOAc in hexane: 0-70% gradient) to afford the title compound. MS (EI) m/z 454 [M+H]$^+$.

Step 4: 3-Cyano-N-(4-(1-(6-cyano-1H-benzo[d]imidazol-2-yl)-3-fluorocyclobutyl) phenyl)benzamide (Ex. 26)

To a vial containing N-(4-(1-((2-amino-5-cyanophenyl)carbamoyl)-3-fluorocyclobutyl)phenyl)-3-cyanobenzamide (71.6 mg, 0.158 mmol) were added DMF (800 µL) and acetic acid (200 µL). The mixture was irradiated in microwave at 150° C. for 2 h. The mixture was filtered and purified by reversed phase HPLC, eluting with water (0.1% TFA)-ACN to afford the title compound as a TFA salt (Ex. 26). $^1$H NMR (600 MHz, DMSO-d$_6$) δ 10.45 (s, 1H), 8.39 (t, J=1.4 Hz, 1H), 8.24 (dt, J=8.0, 1.3 Hz, 1H), 8.11-8.01 (m, 2H), 7.81-7.72 (m, 3H), 7.65 (d, J=8.3 Hz, 1H), 7.57 (dd, J=8.3, 1.5 Hz, 1H), 7.39-7.31 (m, 2H), 5.22 (ddt, J=55.9, 13.9, 6.9 Hz, 1H), 3.58-3.48 (m, 2H), 2.91-2.79 (m, 2H); MS (EI) m/z 436 [M+H]$^+$.

Example 27: N-(3-chlorophenyl)-4-(1-(6-(trifluoromethyl)-1H-imidazo[4,5-b]pyridin-2-yl)cyclobutyl)benzamide (Ex. 27)

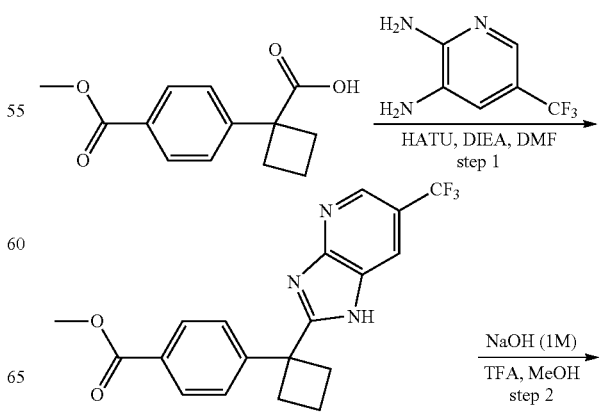

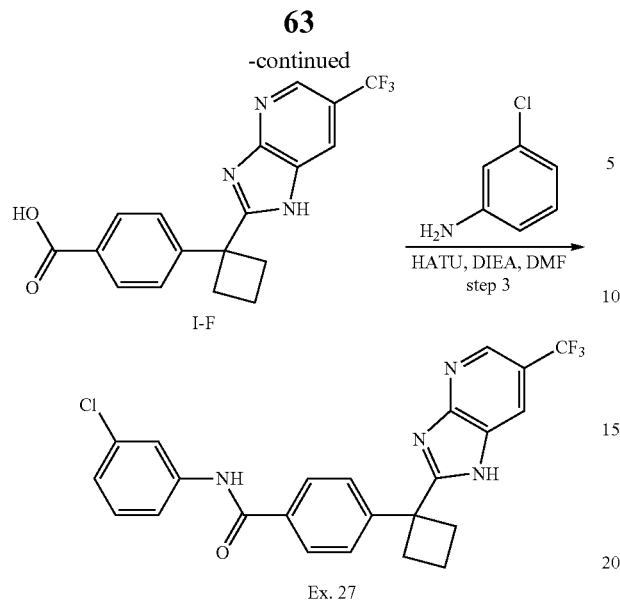

I-F

Ex. 27

Step 1: Methyl 4-(1-(6-(trifluoromethyl)-1H-imidazo[4,5-b]pyridin-2-yl)cyclobutyl)benzoate To a vial were added 1-(4-(methoxycarbonyl)phenyl)cyclobutanecarboxylic acid (25 mg, 0.11 mmol), 5-(trifluoromethyl)pyridine-2,3-diamine (28.4 mg, 0.160 mmol), HATU (60.9 mg, 0.160 mmol), DMF (800 µl) and DIEA (70 µl, 0.40 mmol). The mixture was heated at 130° C. for 20 h. The mixture was filtered and purified by reversed phase HPLC, eluting with ACN/water (0.1% TFA) to afford the title compound as the TFA salt. MS (EI) m/z 376 [M+H]+.

Step 2: 4-(1-(6-(Trifluoromethyl)-1H-imidazo[4,5-b]pyridin-2-yl)cyclobutyl)benzoic Acid (I-F)

To a vial containing methyl 4-(1-(6-(trifluoromethyl)-1H-imidazo[4,5-b]pyridin-2-yl)cyclobutyl)benzoate (18 mg, 0.038 mmol) were added MeOH (100 µl), THF (300 µl) and NaOH (200 µl, 0.200 mmol). The mixture was stirred at RT for 18 h. The organic solvent was removed in vacuo, and the aq. residue was adjusted to pH ~3 by adding aq. HCl (1M). The solvent was removed in vacuo to afford the title compound (I-F). MS (EI) m/z 362 [M+H]+.

Step 3: N-(3-chlorophenyl)-4-(1-(6-(trifluoromethyl)-1H-imidazo[4,5-b]pyridin-2-yl)cyclobutyl)benzamide (Ex. 27)

To a vial were added I-F (13 mg, 0.036 mmol), 3-chloroaniline (25 mg, 0.20 mmol), HATU (20 mg, 0.054 mmol), DMF (400 µl) and DIEA (50 µl, 0.29 mmol). The mixture was stirred at RT for 18 h. The mixture was filtered and purified by reversed phase HPLC, eluting with ACN/water (0.1% TFA) to afford the title compound as a TFA salt (Ex. 6). 1H NMR (600 MHz, DMSO-d6) δ 10.30 (s, 1H), 8.61 (s, 1H), 8.28 (s, 1H), 7.97-7.79 (m, 3H), 7.63 (d, J=8.1 Hz, 1H), 7.50 (d, J=8.1 Hz, 2H), 7.32 (t, J=8.1 Hz, 1H), 7.10 (d, J=7.8 Hz, 1H), 3.14-2.99 (m, 2H), 2.73 (q, J=9.0 Hz, 2H), 2.11-1.81 (m, 2H). MS (EI) m/z 471 [M+H]+.

Example 28: 4-(1-(6-Cyano-1H-imidazo[4,5-b]pyridin-2-yl)-3,3-difluorocyclobutyl)-N-cyclohexylbenzamide (Ex. 28)

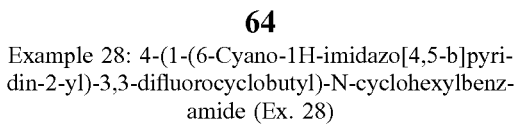

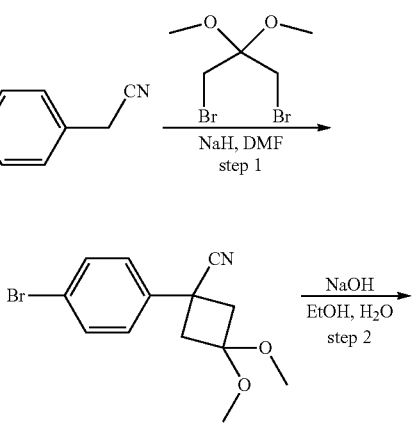

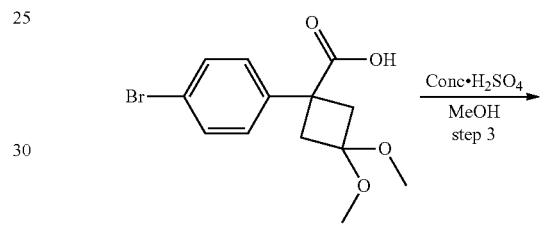

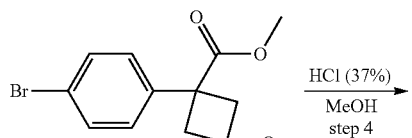

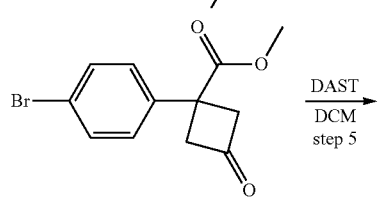

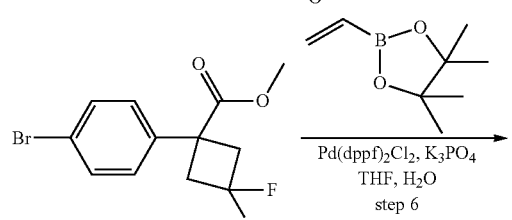

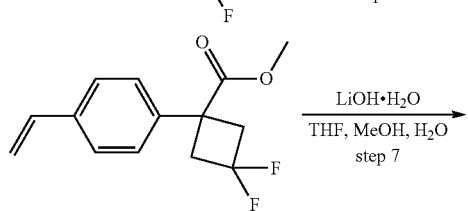

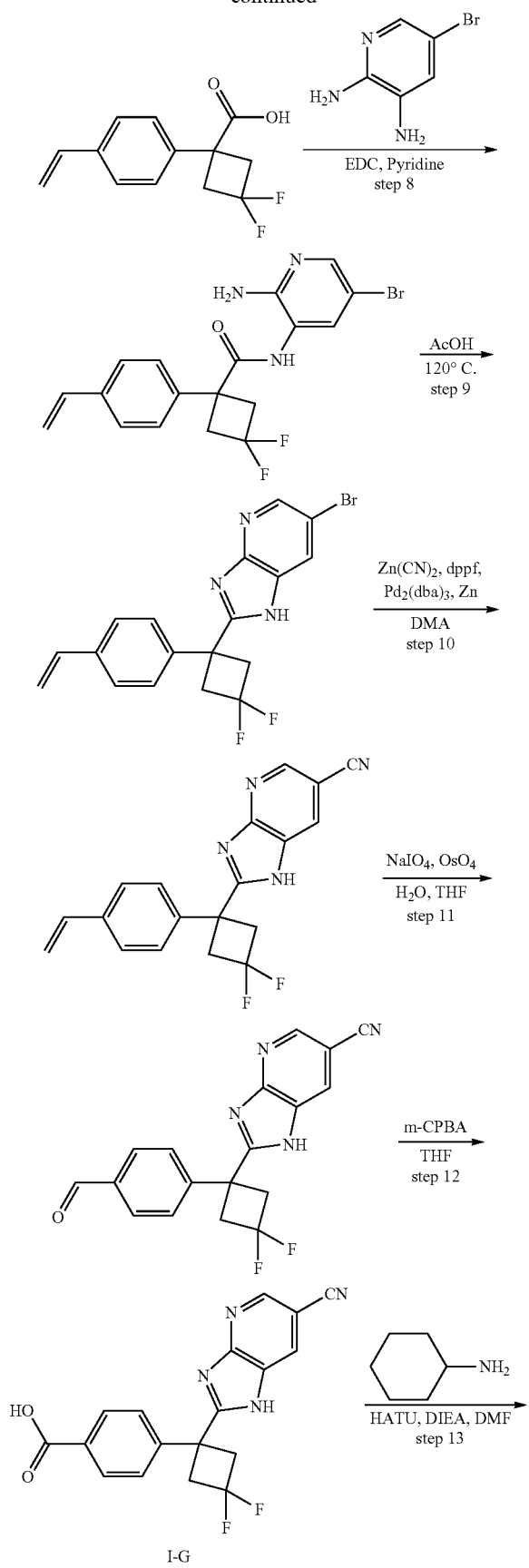

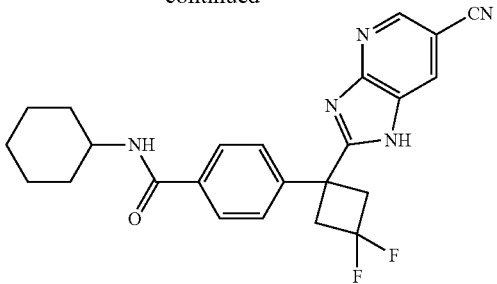

Ex. 28

Step 1: 1-(4-Bromophenyl)-3,3-dimethoxycyclobutane-1-carbonitrile

To a suspension of NaH (4.08 g, 102 mmol) (60% in oil) in DMF (50 mL) was added a solution of 2-(4-bromophenyl)acetonitrile (10 g, 51 mmol) in DMF (50 mL) dropwise at 0° C., followed by the addition of 1,3-dibromo-2,2-dimethoxypropane (13.4 g, 51.0 mmol) at 0° C. The mixture was stirred at 60° C. for 18 h. After cooling to RT, the reaction was quenched by adding water (250 mL) and extracted with EtOAc (150 mL×3). The organic layers were combined, washed with brine, dried over $Na_2SO_4$, filtered and concentrated in vacuo to afford a residue, which was purified by column chromatography on silica gel (PE:ethyl acetate=40:1 to 30:1) to give the title compound. MS (EI) m/z 296 $[M+H]^+$.

Step 2: 1-(4-Bromophenyl)-3,3-dimethoxycyclobutane-1-carboxylic acid

To a solution of 1-(4-bromophenyl)-3,3-dimethoxycyclobutanecarbonitrile (9.3 g, 31 mmol) in EtOH (80 mL) and water (80 mL) was added NaOH (12 mL, 31 mmol) (10% in water) at 15° C. The reaction was stirred and heated at 80° C. for 15 h, then cooled to RT. EtOH was removed in vacuo, and the aqueous solution was extracted with EtOAc. The aqueous layer was acidified with aq. HCl (10%) to pH ~3, then extracted with EtOAc (50 mL×3). The combined organic layers were washed with brine, dried over anhydrous $Na_2SO_4$, filtered and concentrated in vacuo to afford the title compound. $^1$H NMR (400 MHz, DMSO-$d_6$) δ 12.42 (s, 1H), 7.56-7.50 (m, 2H), 7.27-7.22 (m, 2H), 3.06 (s, 3H), 3.00 (s, 3H), 2.95 (d, J=13.4 Hz, 2H), 2.46 (d, J=13.2 Hz, 2H).

Step 3: Methyl 1-(4-bromophenyl)-3,3-dimethoxycyclobutane-1-carboxylate

To a solution of 1-(4-bromophenyl)-3,3-dimethoxycyclobutanecarboxylic acid (2.5 g, 7.9 mmol) in MeOH (50 mL) was added conc. $H_2SO_4$ (3.5 mL, 37 mmol) with stirring at RT. The reaction mixture was stirred at RT for 18 h, then concentrated in vacuo to remove the solvent, diluted with water (30 mL) and extracted by ethyl acetate (30 mL×3). The combined organic layers were washed with brine, dried over anhydrous $Na_2SO_4$, filtered and concentrated in vacuo to afford a residue, which was purified by column chromatography on silica gel (PE/ethyl acetate=40:1 to 20:1) to give the title compound. $^1$H NMR (400 MHz, CDCl$_3$) δ 7.47-7.42 (m, 2H), 7.20-7.16 (m, 2H), 3.65 (s, 3H), 3.19 (s, 3H), 3.10 (s, 3H), 3.13-3.10 (m, 2H), 2.56-2.47 (m, 2H).

Step 4: Methyl 1-(4-bromophenyl)-3-oxocyclobutane-1-carboxylate

To a solution of methyl 1-(4-bromophenyl)-3,3-dimethoxycyclobutanecarboxylate (3.50 g, 10.6 mmol) in MeOH (30 mL) was added conc. HCl (8 mL) at RT. The reaction mixture was stirred at RT for 16 h, then concentrated in vacuo. The residue was purified by column chromatography on silica gel (PE/ethyl acetate=50:1 to 25:1) to give the title compound. $^1$H NMR (400 MHz, CDCl$_3$) δ 7.52 (d, J=8.6 Hz, 2H), 7.24 (d, J=8.6 Hz, 2H), 3.95-3.88 (m, 2H), 3.71 (s, 3H), 3.57-3.49 (m, 2H).

Step 5: Methyl 1-(4-bromophenyl)-3,3-difluorocyclobutane-1-carboxylate

To a solution of methyl 1-(4-bromophenyl)-3-oxocyclobutanecarboxylate (2.53 g, 8.94 mmol) in DCM (25 mL) was added DAST (2.36 mL, 17.9 mmol) with stirring at 0° C. under N$_2$ atmosphere. After the addition was complete, the reaction mixture was stirred at RT for 16 h, then quenched with sat. NaHCO$_3$ (20 mL) slowly, extracted with DCM (30 mL×3). The combined organic layers were washed with brine, dried over anhydrous Na$_2$SO$_4$, filtered and concentrated in vacuo to afford a residue, which was purified by column chromatography on silica gel (PE:ethyl acetate=60:1 to 50:1) to give the title compound. $^1$H NMR (400 MHz, CDCl$_3$) δ 7.49 (d, J=8.6 Hz, 2H), 7.18 (d, J=8.6 Hz, 2H), 3.69 (s, 3H), 3.53-3.41 (m, 2H), 3.08-2.94 (m, 2H).

Step 6: Methyl 3,3-difluoro-1-(4-vinylphenyl)cyclobutane-1-carboxylate

To a stirred solution of methyl 1-(4-bromophenyl)-3,3-difluorocyclobutanecarboxylate (2.0 g, 6.5 mmol) in THF (15 mL) and water (1.5 mL) were added 4,4,5,5-tetramethyl-2-vinyl-1,3,2-dioxaborolane (1.21 g, 7.87 mmol), K$_3$PO$_4$ (4.17 g, 19.7 mmol) and Pd(dppf)$_2$Cl$_2$ (0.480 g, 0.655 mmol) at RT under N$_2$. The reaction mixture was stirred at 80° C. under N$_2$ for 16 h, then cooled to RT. The reaction mixture was poured into water (30 mL) and extracted with EtOAc (30 mL×4). The combined organic layers were washed with brine, dried over anhydrous Na$_2$SO$_4$, filtered and concentrated in vacuo to afford a residue, which was purified by column chromatography on silica gel (PE/ethyl acetate=100:1) to give the title compound. $^1$H NMR (400 MHz, CDCl$_3$) δ 7.42-7.38 (m, 2H), 7.29-7.27 (m, 1H), 7.26-7.24 (m, 1H), 6.70 (dd, J=17.6, 10.8 Hz, 1H), 5.75 (dd, J=17.6, 0.8 Hz, 1H), 5.27 (dd, J=10.8, 0.8 Hz, 1H), 3.68 (s, 3H), 3.40-3.53 (m, 2H), 2.98-3.12 (m, 2H).

Step 7: 3,3-Difluoro-1-(4-vinylphenyl)cyclobutane-1-carboxylic Acid

To a stirred solution of methyl 3,3-difluoro-1-(4-vinylphenyl)cyclobutane-1-carboxylate (1.4 g, 5.6 mmol) in THF (5 mL), MeOH (5 mL) and water (2.5 mL) was added lithium hydroxide hydrate (932 mg, 22.2 mmol). The reaction mixture was stirred at RT for 16 h, then diluted with water (10 mL), acidified to pH~3 by adding aq. HCl (3 M) and extracted with EtOAc (30 mL×2). The combined organic layers were washed with brine, dried over anhydrous Na$_2$SO$_4$, filtered and concentrated in vacuo to afford the title compound. $^1$H NMR (400 MHz, CDCl$_3$) δ 7.41 (d, J=8.4 Hz, 2H), 7.30-7.25 (m, 2H), 6.70 (dd, J=17.6, 11.0 Hz, 1H), 5.75 (d, J=17.6 Hz, 1H), 5.28 (d, J=11.0 Hz, 1H), 3.55-3.41 (m, 2H), 3.14-3.00 (m, 2H).

Step 8: N-(2-amino-5-bromopyridin-3-yl)-3,3-difluoro-1-(4-vinylphenyl)cyclobutane-1-carboxamide To a solution of 3,3-difluoro-1-(4-vinylphenyl)cyclobutanecarboxylic acid (800 mg, 3.36 mmol) in pyridine (8 mL) was added EDC (1931 mg, 10.07 mmol) and 5-bromopyridine-2,3-diamine (695 mg, 3.69 mmol). The reaction mixture was stirred at RT for 18 h, then stirred at 30° C. for another 7 h. The reaction mixture was poured into water (30 mL) and extracted with EtOAc (40 mL×3). The combined organic layers were washed with brine, dried over anhydrous Na$_2$SO$_4$, filtered and concentrated in vacuo to afford a residue, which was purified by column chromatography on silica gel (eluting with PE:ethyl acetate=5:1 to 3:1) to give the title compound. $^1$H NMR (400 MHz, CDCl$_3$) δ 7.99 (d, J=2.0 Hz, 1H), 7.66 (d, J=1.6 Hz, 1H), 7.54 (d, J=8.2 Hz, 2H), 7.36 (d, J=8.2 Hz, 2H), 6.74 (dd, J=17.6, 11.0 Hz, 1H), 6.59 (br s, 1H), 5.83 (d, J=17.6 Hz, 1H), 5.36 (d, J=10.8 Hz, 1H), 4.15 (br s, 2H), 3.59 (q, J=13.2 Hz, 2H), 3.21-3.04 (m, 2H).

Step 9: 6-Bromo-2-(3,3-difluoro-1-(4-vinylphenyl)cyclobutyl)-1H-imidazo[4,5-b]pyridine A solution of N-(2-amino-5-bromopyridin-3-yl)-3,3-difluoro-1-(4-vinylphenyl)cyclobutanecarboxamide (460 mg, 1.13 mmol) in AcOH (8 mL) was stirred at 120° C. for 17 h. The reaction mixture was cooled down to RT and concentrated in vacuo to afford a residue, which was purified by column chromatography on silica gel (eluting with PE/ethyl acetate=15:1) to give the title compound. $^1$H NMR (400 MHz, CDCl$_3$) δ 10.29 (br s, 1H), 8.19 (d, J=1.8 Hz, 1H), 8.17 (d, J=2.0 Hz, 1H), 7.47 (d, J=8.4 Hz, 2H), 7.34 (d, J=8.4 Hz, 2H), 6.71 (dd, J=17.4, 11.0 Hz, 1H), 5.78 (d, J=17.6 Hz, 1H), 5.31 (d, J=11.0 Hz, 1H), 3.70-3.85 (m, 2H), 3.31-3.44 (m, 2H).

Step 10: 2-(3,3-Difluoro-1-(4-vinylphenyl)cyclobutyl)-1H-imidazo[4,5-b]pyridine-6-carbonitrile To a mixture of 6-bromo-2-(3,3-difluoro-1-(4-vinylphenyl)cyclobutyl)-1H-imidazo[4,5-b]pyridine (380 mg, 0.974 mmol), dppf (32 mg, 0.058 mmol) and zinc (13 mg, 0.20 mmol) in DMA (4 mL) were added Zn(CN)$_2$ (229 mg, 1.95 mmol) and Pd$_2$(dba)$_3$ (18 mg, 0.020 mmol) at RT. The resulting mixture was irradiated in the microwave at 150° C. for 30 min, then was poured into water (20 mL) and extracted with EtOAc (30 mL×2). The combined organic layers were washed with brine, dried over anhydrous Na$_2$SO$_4$, filtered and concentrated in vacuo to afford a residue, which was purified by column chromatography on silica gel (eluting with PE/ethyl acetate=8:1 to 5:1) to give the title compound. MS (EI) m/z 337 [M+H]$^+$.

Step 11. 2-(3,3-Difluoro-1-(4-formylphenyl)cyclobutyl)-1H-imidazo[4,5-b]pyridine-6-carbonitrile To a stirred solution of 2-(3,3-difluoro-1-(4-vinylphenyl)cyclobutyl)-1H-imidazo[4,5-b]pyridine-6-carbonitrile (190 mg, 0.565 mmol) in THF (20 mL) and water (1 mL) were added NaIO$_4$ (604 mg, 2.82 mmol) and osmium(VIII) oxide (14 mL, 1.4 mmol, 0.1 M).

The reaction mixture was stirred at RT for 1.5 h, then quenched with saturated aq. Na$_2$SO$_3$ (15 mL) and extracted with EtOAc (30 mL×3). The combined organic layers were washed with brine, dried over anhydrous Na$_2$SO$_4$, filtered and concentrated in vacuo to afford a residue, which was purified by prep-TLC (SiO$_2$, PE:ethyl acetate=1:1) to give the title compound. MS (EI) m/z 339 [M+H]$^+$.

Step 12. 4-(1-(6-Cyano-1H-imidazo[4,5-b]pyridin-2-yl)-3,3-difluorocyclobutyl)benzoic Acid (I-G)

To a stirred solution of 2-(3,3-difluoro-1-(4-formylphenyl)cyclobutyl)-1H-imidazo[4,5-b]pyridine-6-carbonitrile (100 mg, 0.296 mmol) in THF (3 mL) was added mCPBA (102 mg, 0.591 mmol). The reaction mixture was stirred at 60° C. for 16 h, then cooled to RT. The reaction was quenched with saturated aq. Na$_2$SO$_3$ (20 mL) and extracted with EtOAc (30 mL×3). The combined organic layers were washed with brine, dried over anhydrous Na$_2$SO$_4$, filtered and concentrated in vacuo to afford a residue, which was purified by prep-TLC (SiO$_2$, PE:ethyl acetate=1:1) to give the title compound (I-G). MS (EI) m/z 355 [M+H]$^+$.

Step 13. 4-(1-(6-Cyano-1H-imidazo[4,5-b]pyridin-2-yl)-3,3-difluorocyclobutyl)-N-cyclohexylbenzamide (Ex. 28)

To a stirred solution of I-G (20 mg, 0.056 mmol) in DMF (2 mL) were added HATU (33 mg, 0.087 mmol) and DIEA (0.03 mL, 0.172 mmol). The reaction mixture was stirred at RT for 0.5 h, followed by addition of the solution of cyclohexylamine (8.0 mg, 0.081 mmol) in DMF (1 mL). The reaction mixture was stirred at RT for 16 h, diluted with water (80 mL) and extracted with EtOAc (50 mL×2). The combined organic layers were washed with brine, dried over Na$_2$SO$_4$, filtered and concentrated in vacuo to afford a residue, which was purified by reversed phase HPLC, eluting with ACN/water (0.05% ammonia hydroxide v/v) to afford the title compound (Ex. 28). $^1$H NMR (400 MHz, CD$_3$OD) δ 8.6 (d, J=1.8 Hz, 1H), 8.3 (d, J=1.5 Hz, 1H), 7.8 (d, J=8.4 Hz, 2H), 7.5 (d, J=8.4 Hz, 2H), 3.9-3.7 (m, 3H), 3.6-3.3 (m, 2H), 1.9 (d, J=11.5 Hz, 2H), 1.8 (d, J=13.0 Hz, 2H), 1.7 (d, J=14.1 Hz, 1H), 1.5-1.2 (m, 5H). MS (EI) Calc'd for C$_{24}$H$_{24}$F$_2$N$_5$O [M+H]$^+$ 436; found 436.

Example 29: 4-(1-(6-Cyano-1H-imidazo[4,5-b]pyridin-2-yl)-3,3-difluorocyclobutyl)-N-(6-methylpyridin-2-yl)benzamide (Ex. 29)

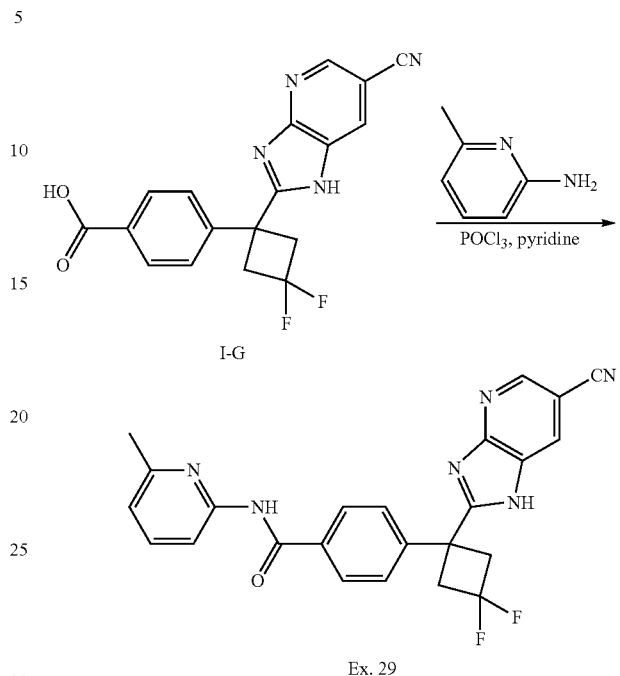

To a stirred solution of I-G (20 mg, 0.056 mmol) and 6-methylpyridin-2-amine (13 mg, 0.12 mmol) in pyridine (3 mL) was added POCl$_3$ (0.10 mL, 1.1 mmol) dropwise at 0° C. The reaction mixture was stirred at 0° C. for 1 h, then quenched by adding water (10 mL), and extracted with EtOAc (10 mL×2). The combined organic layers were washed with brine, dried over Na$_2$SO$_4$, filtered and concentrated in vacuo to afford a residue, which was purified by reversed phase HPLC, eluting with ACN/water (0.1% TFA) to afford the title compound (Ex. 29). $^1$H NMR (400 MHz, CD$_3$OD) δ 8.7 (d, J=1.8 Hz, 1H), 8.3 (d, J=1.8 Hz, 1H), 8.2-8.0 (m, 3H), 7.8 (d, J=8.4 Hz, 1H), 7.7 (d, J=8.6 Hz, 2H), 7.3 (d, J=7.7 Hz, 1H), 3.9-3.7 (m, 2H), 3.6-3.4 (m, 2H), 2.6 (s, 3H). MS (EI) Calc'd for C$_{24}$H$_{19}$F$_2$N$_6$O [M+H]$^+$ 445; found 445.

Examples 30-38

Examples 30-38 shown in the following table were prepared in an analogous fashion to Examples 27 and 28, using the corresponding amines.

| Ex. # | Structure | Chemical Name | Mass [M + H]+ |
|---|---|---|---|
| 30 | 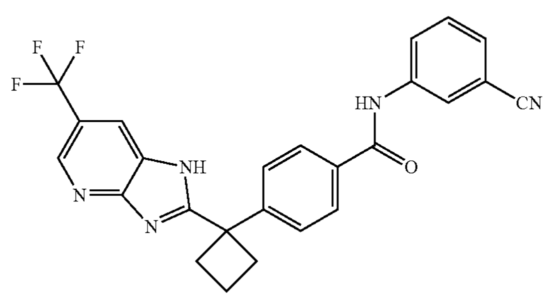 [SMILES: N#Cc1cccc(NC(=O)c2ccc(C3(c4nc5ncc(C(F)(F)F)cc5[nH]4)CCC3)cc2)c1] | N-(3-cyanophenyl)-4-{1-[6-(trifluoromethyl)-1H-imidazo[4,5-b]pyridin-2-yl]cyclobutyl}benzamide | Calc'd 462, found 462 |

-continued

| Ex. # | Structure | Chemical Name | Mass [M + H]+ |
|---|---|---|---|
| 31 | 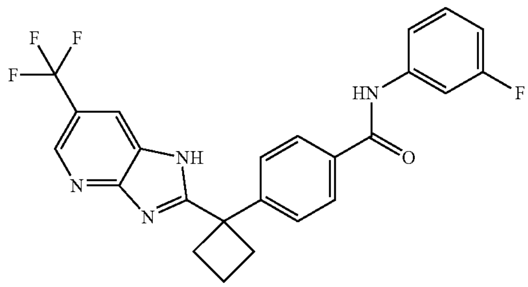 [SMILES: O=C(Nc1cccc(F)c1)c1ccc(C2(c3nc4ncc(C(F)(F)F)cc4[nH]3)CCC2)cc1] | N-(3-fluorophenyl)-4-{1-[6-(trifluoromethyl)-1H-imidazo[4,5-b]pyridin-2-yl]cyclobutyl}benzamide | Calc'd 455, found 455 |
| 32 | 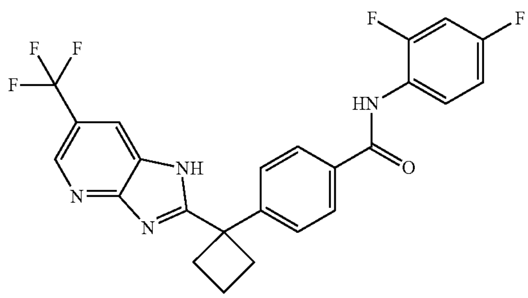 [SMILES: O=C(Nc1ccc(F)cc1F)c1ccc(C2(c3nc4ncc(C(F)(F)F)cc4[nH]3)CCC2)cc1] | N-(2,4-difluorophenyl)-4-{1-[6-(trifluoromethyl)-1H-imidazo[4,5-b]pyridin-2-yl]cyclobutyl}benzamide | Calc'd 473, found 473 |
| 33 | 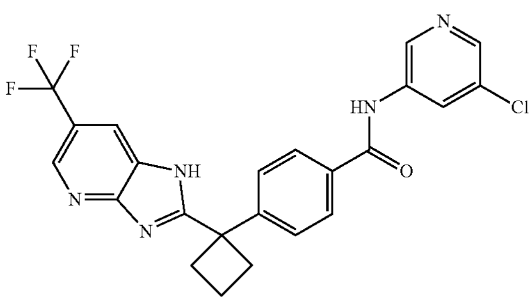 [SMILES: O=C(Nc1cncc(Cl)c1)c1ccc(C2(c3nc4ncc(C(F)(F)F)cc4[nH]3)CCC2)cc1] | N-(5-chloropyridin-3-yl)-4-{1-[6-(trifluoromethyl)-1H-imidazo[4,5-b]pyridin-2-yl]cyclobutyl}benzamide | Calc'd 472, found 472 |
| 34 | 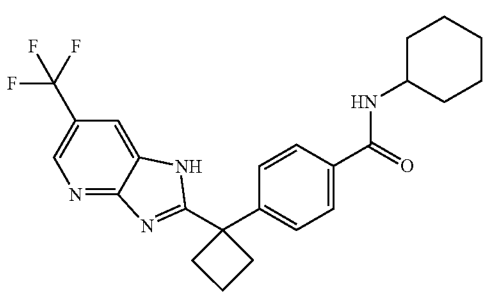 [SMILES: O=C(NC1CCCCC1)c1ccc(C2(c3nc4ncc(C(F)(F)F)cc4[nH]3)CCC2)cc1] | N-cyclohexyl-4-{1-[6-(trifluoromethyl)-1H-imidazo[4,5-b]pyridin-2-yl]cyclobutyl}benzamide | Calc'd 443, found 443 |
| 35 | 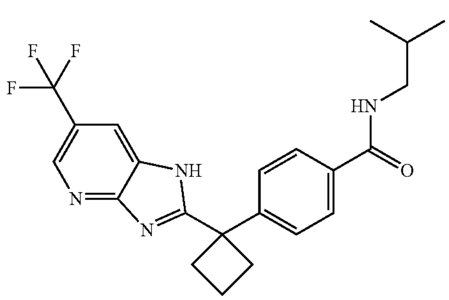 [SMILES: CC(C)CNC(=O)c1ccc(C2(c3nc4ncc(C(F)(F)F)cc4[nH]3)CCC2)cc1] | N-(2-methylpropyl)-4-{1-[6-(trifluoromethyl)-1H-imidazo[4,5-b]pyridin-2-yl]cyclobutyl}benzamide | Calc'd 417, found 417 |

| Ex. # | Structure | Chemical Name | Mass [M + H]+ |
|---|---|---|---|
| 36 | 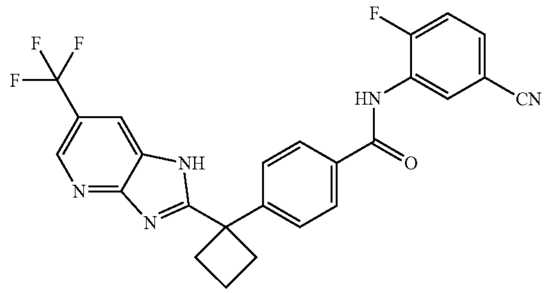 [SMILES: N#Cc1ccc(F)c(NC(=O)c2ccc(C3(c4nc5ncc(C(F)(F)F)cc5[nH]4)CCC3)cc2)c1] | N-(5-cyano-2-fluorophenyl)-4-{1-[6-(trifluoromethyl)-1H-imidazo[4,5-b]pyridin-2-yl]cyclobutyl}benzamide | Calc'd 480, found 480 |
| 37 | 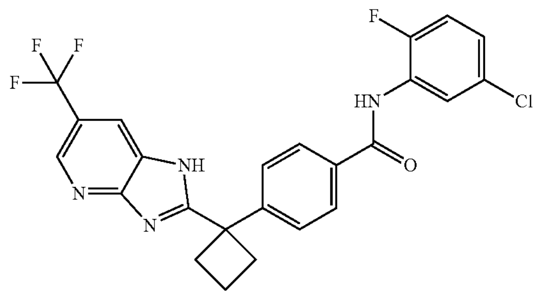 [SMILES: O=C(Nc1cc(Cl)ccc1F)c1ccc(C2(c3nc4ncc(C(F)(F)F)cc4[nH]3)CCC2)cc1] | N-(5-chloro-2-fluorophenyl)-4-{1-[6-(trifluoromethyl)-1H-imidazo[4,5-b]pyridin-2-yl]cyclobutyl}benzamide | Calc'd 489, found 489 |
| 38 | 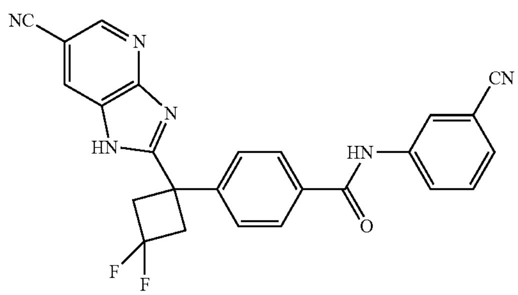 [SMILES: N#Cc1cccc(NC(=O)c2ccc(C3(c4nc5ncc(C#N)cc5[nH]4)CC(F)(F)C3)cc2)c1] | 4-[1-(6-cyano-1H-imidazo[4,5-b]pyridin-2-yl)-3,3-difluorocyclobutyl]-N-(3-cyanophenyl)benzamide | Calc'd 455, found 455 |

Example 39: 2-(1-(4-(6-Cyclopropyl-4-methylpyridin-3-yl)phenyl)cyclobutyl)-1H-imidazo[4,5-b]pyridine-6-carbonitrile (Ex. 39)

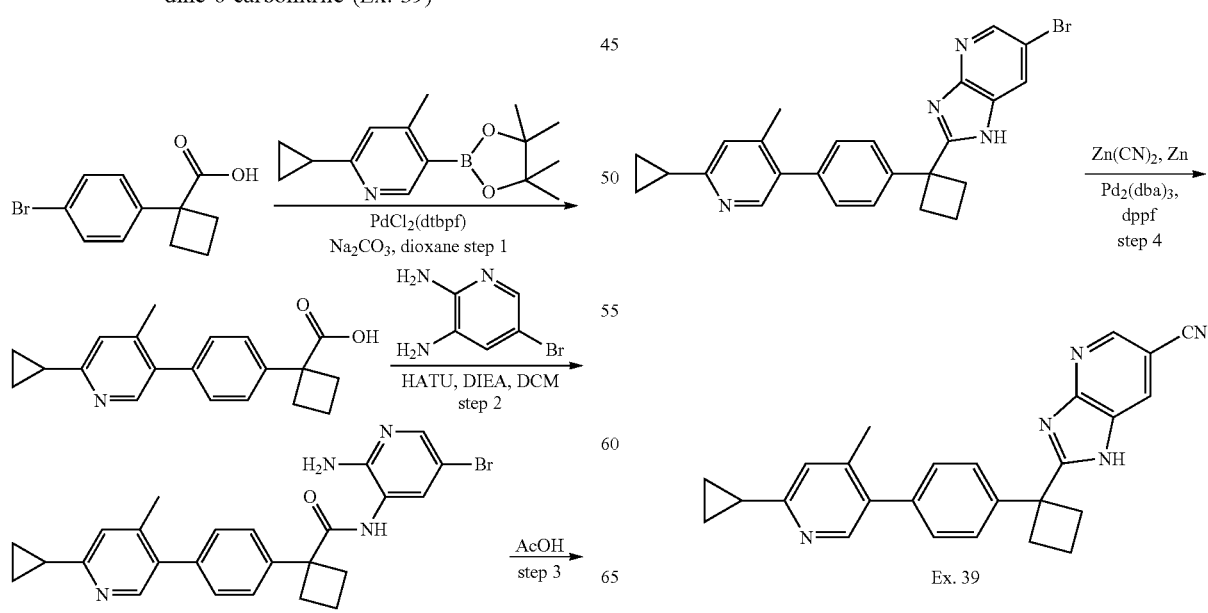

Step 1: 1-(4-(6-Cyclopropyl-4-methylpyridin-3-yl)phenyl)cyclobutane-1-carboxylic Acid To a vial were added 2-cyclopropyl-4-methyl-5-(4,4,5,5-tetramethyl-1,3,2-dioxaborolan-2-yl)pyridine (203 mg, 0.784 mmol), 1-(4-bromophenyl)cyclobutanecarboxylic acid (200 mg, 0.784 mmol), PdCl$_2$(dtbpf) (51 mg, 0.078 mmol), sodium carbonate (0.784 mL, 1.57 mmol) and 1,4-dioxane (2 mL). The reaction mixture was evacuated and back filled with N$_2$ three times and heated at 80° C. for 4 h. The reaction mixture was filtered and concentrated in vacuo to afford a residue, which was purified by column chromatography on silica gel (MeOH in DCM, 2-20% gradient) to give the title compound. MS (EI) 308 [M+H]$^+$.

Step 2: N-(2-amino-5-bromopyridin-3-yl)-1-(4-(6-cyclopropyl-4-methylpyridin-3-yl)phenyl)cyclobutane-1-carboxamide To a solution of 1-(4-(6-cyclopropyl-4-methylpyridin-3-yl)phenyl)cyclobutanecarboxylic acid (220 mg, 0.716 mmol) in DCM (5 mL) was added HATU (327 mg, 0.859 mmol). After stirring for 10 min, 5-bromopyridine-2,3-diamine (135 mg, 0.716 mmol), DIEA (0.375 mL, 2.15 mmol) were added and the reaction mixture was stirred for 12 h at RT. The reaction mixture was diluted with EtOAc, then extracted with 3 portions of aq. HCl (1 M), 2 portions of water, 1 portion of brine and 1 portion of sat. NaHCO$_3$. The organic phase was dried over Na$_2$SO$_4$, filtered and concentrated in vacuo to afford a residue, which was purified by column chromatography on silica gel (DCM in EtOAc, 10-100% gradient) to give the title compound. MS (EI) 477 [M+H]$^+$.

Step 3: 6-Bromo-2-(1-(4-(6-cyclopropyl-4-methylpyridin-3-yl)phenyl)cyclobutyl)-1H-imidazo[4,5-b]pyridine A solution of N-(2-amino-5-bromopyridin-3-yl)-1-(4-(6-cyclopropyl-4-methylpyridin-3-yl)phenyl)cyclobutanecarboxamide (103 mg, 0.216 mmol) in AcOH (2 mL) was irradiated in the microwave at 150° C. for 30 min. The reaction mixture was filtered and concentrated in vacuo to afford a residue, which was purified by reversed phase HPLC, eluting with ACN/water (0.1% TFA) to give the title compound. MS (EI) 459 [M+H]$^+$.

Step 4: 2-(1-(4-(6-Cyclopropyl-4-methylpyridin-3-yl)phenyl)cyclobutyl)-1H-imidazo[4,5-b]pyridine-6-carbonitrile (Ex. 39)

To a vial were added 6-bromo-2-(1-(4-(6-cyclopropyl-4-methylpyridin-3-yl)phenyl)cyclobutyl)-1H-imidazo[4,5-b]pyridine (100 mg, 0.218 mmol), Zn(CN)$_2$ (61.3 mg, 0.522 mmol), zinc powder (10.2 mg, 0.157 mmol), Pd$_2$(dba)$_3$ (32 mg, 0.035 mmol), dppf (39 mg, 0.070 mmol) and DMA (2 mL). The reaction mixture was evacuated and back filled with N$_2$ three times, then irradiated in the microwave at 130° C. for 2 h. The reaction mixture was filtered and purified by reversed phase HPLC, eluting with ACN/water (0.1% TFA) to afford the title compound (Ex. 39). $^1$H NMR (499 MHz, DMSO-d$_6$) δ 8.76-8.65 (m, 1H), 8.51 (s, 2H), 7.61 (s, 1H), 7.55 (d, J=8.1 Hz, 2H), 7.46 (d, J=8.1 Hz, 2H), 3.20-3.04 (m, 2H), 2.86-2.72 (m, 2H), 2.39 (s, 3H), 2.37-2.24 (m, 1H), 2.13-1.87 (m, 2H), 1.44-1.26 (m, 2H), 1.26-1.07 (m, 2H). MS (ESI) 406 [M+H]$^+$.

Example 40: 2-(3-(4-(6-Cyclopropyl-4-methylpyridin-3-yl)phenyl)oxetan-3-yl)-6-(trifluoromethyl)-1H-imidazo[4,5-b]pyridine (Ex. 40)

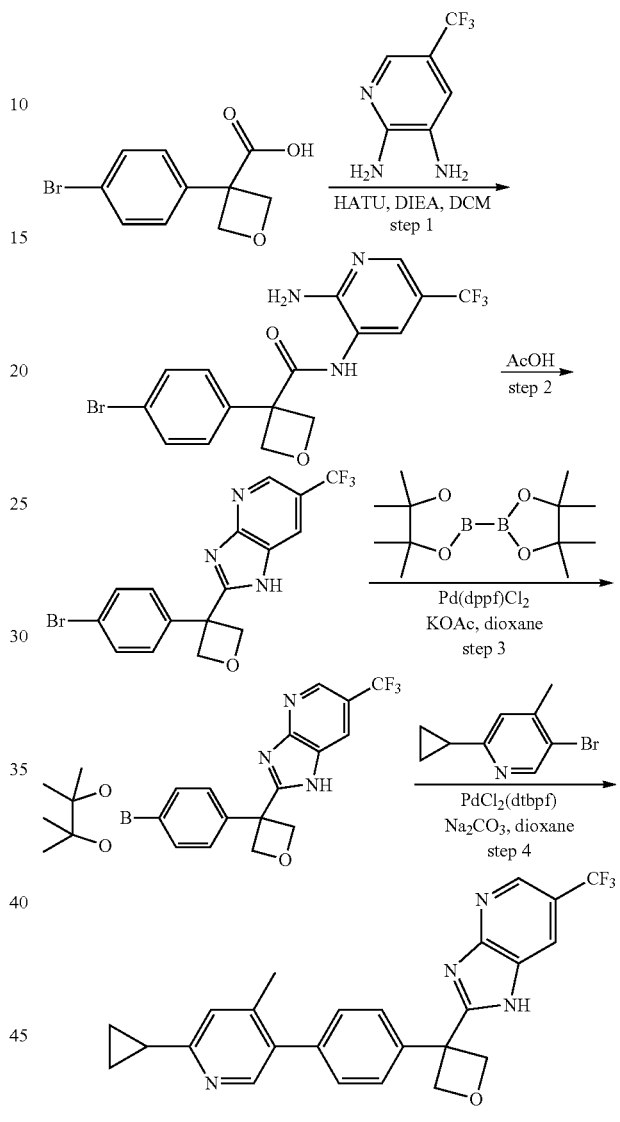

Ex. 40

Step 1: N-(2-amino-5-(trifluoromethyl)pyridin-3-yl)-3-(4-bromophenyl)oxetane-3-carboxamide To a solution of 3-(4-bromophenyl)oxetane-3-carboxylic acid (550.0 mg, 2.139 mmol) in DCM (15.0 mL) was added HATU (976 mg, 2.57 mmol). The reaction was stirred for 10 min. Then to the reaction mixture were added 5-(trifluoromethyl)pyridine-2,3-diamine (379 mg, 2.14 mmol), DIEA (1.12 mL, 6.42 mmol) and reaction was stirred at RT for 12 h. The reaction was diluted with EtOAc and washed with 3 portions of 1 N HCl, 2 portions of water, 1 portion of brine, 1 portion of NaHCO$_3$ (sat.). The organic layer was dried over Na$_2$SO$_4$, filtered, and concentrated in vacuo to afford a residue, which was purified by column chromatography on silica gel (EtOAc in DCM: 0-1005% gradient) to afford the title compound. MS (EI) m/z 416 [M+H]$^+$.

Step 2: 2-(3-(4-Bromophenyl)oxetan-3-yl)-6-(trifluoromethyl)-1H-imidazo[4,5-b]pyridine A solution of N-(2-amino-5-(trifluoromethyl)pyridin-3-yl)-3-(4-bromophenyl)oxetane-3-carboxamide (330 mg, 0.793 mmol) in AcOH (5.0 mL) was irradiated in microwave at 150° C. for 1 h. The mixture was evaporated in vacuo to afford residue, which was purified by column chromatography on silica gel (EtOAc/Hexane: 0-100% gradient) to afford 2-(3-(4-bromophenyl)oxetan-3-yl)-6-(trifluoromethyl)-1H-imidazo[4,5-b]pyridine. MS (EI) m/z 398 [M+H]+.

Step 3: 2-(3-(4-(4,4,5,5-Tetramethyl-1,3,2-dioxaborolan-2-yl)phenyl)oxetan-3-yl)-6-(trifluoromethyl)-1H-imidazo[4,5-b]pyridine A flask was charged with 2-(3-(4-bromophenyl)oxetan-3-yl)-6-(trifluoromethyl)-1H-imidazo[4,5-b]pyridine (180 mg, 0.452 mmol), bis(pinacolato)diboron (298 mg, 1.18 mmol), potassium acetate (131 mg, 1.34 mmol), PdCl$_2$(dppf)-DCM adduct (37 mg, 0.045 mmol) and dioxane (5.0 ml). The mixture was evacuated and back filled with N$_2$ 3 times, then heated at 80° C. for 4 h. The reaction mixture was cooled to RT and filtered through a Celite® pad. The filtrate was concentrated in vacuo. The residue was dissolved into DCM and washed with water and brine. The organic layer was dried over Na$_2$SO$_4$, filtered and concentrated in vacuo to afford a residue, which was purified by column chromatography on silica gel (EtOAc in hexane: 0-100% gradient) to afford the title compound. MS (EI) m/z 446 [M+H]+.

Step 4: 2-(3-(4-(6-Cyclopropyl-4-methylpyridin-3-yl)phenyl)oxetan-3-yl)-6-(trifluoromethyl)-1H-imidazo[4,5-b]pyridine (Ex. 40)

To a vial were added 5-bromo-2-cyclopropyl-4-methylpyridine (38.1 mg, 0.180 mmol), 2-(3-(4-(4,4,5,5-tetramethyl-1,3,2-dioxaborolan-2-yl)phenyl)oxetan-3-yl)-6-(trifluoromethyl)-1H-imidazo[4,5-b]pyridine (80.0 mg, 0.180 mmol), PdCl$_2$(dtbpf) (12 mg, 0.018 mmol), Na$_2$CO$_3$ (2M, 0.18 mL, 0.36 mmol) and 1,4-dioxane (2.0 mL). The mixture was evacuated and back filled with N$_2$ three times, then heated at 80° C. for 4 h. The solvents were removed in vacuo. The resulting residue was suspended in EtOAc/DCM, filtered through a Celite® pad, and washed with EtOAc and DCM. The combined filtrates were concentrated in vacuo to afford a residue, which was purified by reversed phase HPLC, eluting with water (0.1% TFA)-ACN to afford the title compound as a TFA salt (Ex. 40). $^1$H NMR (499 MHz, Methanol-d$_4$) δ 8.69 (s, 1H), 8.40 (s, 1H), 8.28 (s, 1H), 7.95-7.10 (m, 5H), 5.55 (d, J=6.2 Hz, 2H), 5.33 (d, J=6.2 Hz, 2H), 2.49 (s, 3H), 2.33 (dq, J=8.6, 5.0, 4.4 Hz, 1H), 1.55-1.38 (m, 2H), 1.38-1.12 (m, 2H); MS (EI) m/z 451 [M+H]+.

Examples 41-49

Examples 41-49 showed in the following table were prepared in an analogous fashion to Examples 40 by using the corresponding acids and amines.

| Ex. # | Structure | Chemical Name | Mass [M + H]+ |
|---|---|---|---|
| 41 | 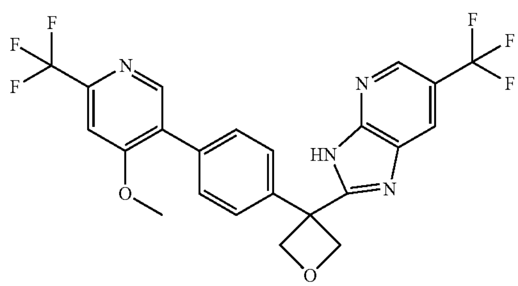 [SMILES: COc1cc(C(F)(F)F)ncc1-c1ccc(C2(c3nc4cc(C(F)(F)F)cnc4[nH]3)COC2)cc1] | 2-(3-{4-[4-methoxy-6-(trifluoromethyl)pyridin-3-yl]phenyl}oxetan-3-yl)-6-(trifluoromethyl)-3H-imidazo[4,5-b]pyridine | Calc'd 495, found 495 |
| 42 | 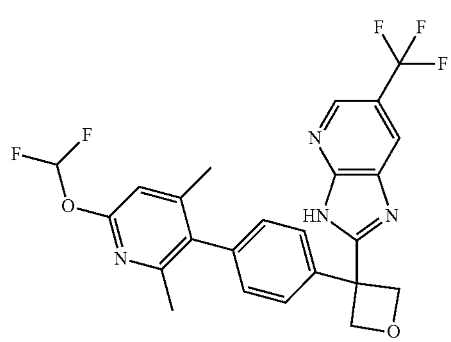 [SMILES: Cc1cc(OC(F)F)nc(C)c1-c1ccc(C2(c3nc4cc(C(F)(F)F)cnc4[nH]3)COC2)cc1] | 2-(3-{4-[6-(difluoromethoxy)-2,4-dimethylpyridin-3-yl]phenyl}oxetan-3-yl)-6-(trifluoromethyl)-3H-imidazo[4,5-b]pyridine | Calc'd 491, found 491 |

-continued

| Ex. # | Structure | Chemical Name | Mass [M + H]+ |
|---|---|---|---|
| 43 | 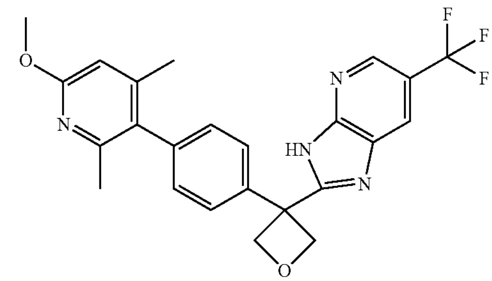 [SMILES: COc1cc(C)c(-c2ccc(C3(c4nc5cc(C(F)(F)F)cnc5[nH]4)COC3)cc2)c(C)n1] | 2-{3-[4-(6-methoxy-2,4-dimethylpyridin-3-yl)phenyl]oxetan-3-yl}-6-(trifluoromethyl)-3H-imidazo[4,5-b]pyridine | Calc'd 455, found 455 |
| 44 | 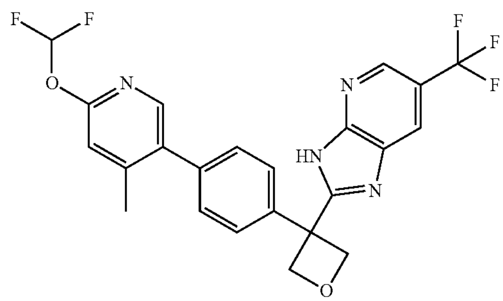 [SMILES: Cc1cc(OC(F)F)ncc1-c1ccc(C2(c3nc4cc(C(F)(F)F)cnc4[nH]3)COC2)cc1] | 2-(3-{4-[6-(difluoromethoxy)-4-methylpyridin-3-yl]phenyl}oxetan-3-yl)-6-(trifluoromethyl)-3H-imidazo[4,5-b]pyridine | Calc'd 477, found 477 |
| 45 | 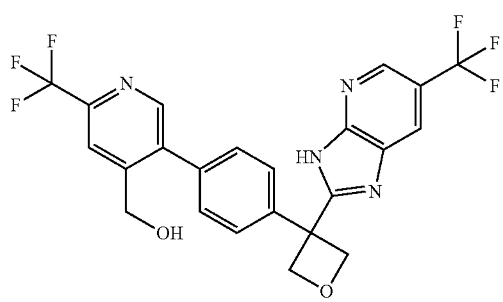 [SMILES: OCc1cc(C(F)(F)F)ncc1-c1ccc(C2(c3nc4cc(C(F)(F)F)cnc4[nH]3)COC2)cc1] | [2-(trifluoromethyl)-5-(4-{3-[6-(trifluoromethyl)-3H-imidazo[4,5-b]pyridin-2-yl]oxetan-3-yl}phenyl)pyridin-4-yl]methanol | Calc'd 495, found 495 |
| 46 | 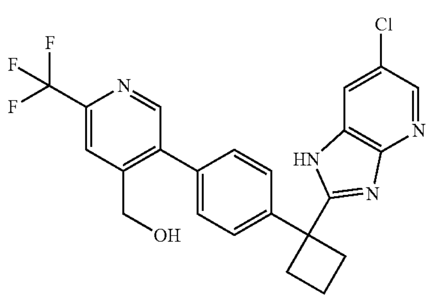 [SMILES: OCc1cc(C(F)(F)F)ncc1-c1ccc(C2(c3nc4ncc(Cl)cc4[nH]3)CCC2)cc1] | [5-{4-[1-(6-chloro-1H-imidazo[4,5-b]pyridin-2-yl)cyclobutyl]phenyl}-2-(trifluoromethyl)pyridin-4-yl]methanol | Calc'd 459, found 459 |
| 47 | 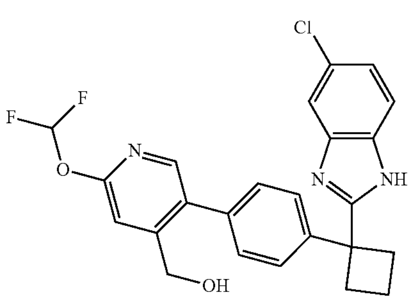 [SMILES: OCc1cc(OC(F)F)ncc1-c1ccc(C2(c3nc4cc(Cl)ccc4[nH]3)CCC2)cc1] | [5-{4-[1-(5-chloro-1H-benzimidazol-2-yl)cyclobutyl]phenyl}-2-(difluoromethoxy)pyridin-4-yl]methanol | Calc'd 456, found 456 |

| Ex. # | Structure | Chemical Name | Mass [M + H]+ |
|---|---|---|---|
| 48 | 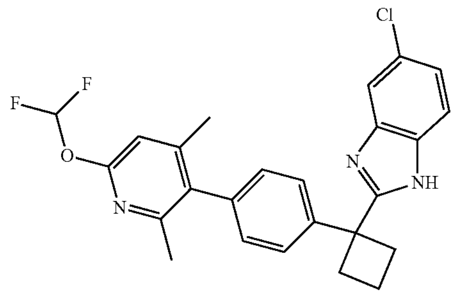 [SMILES: Cc1cc(OC(F)F)nc(C)c1-c1ccc(C2(c3nc4cc(Cl)ccc4[nH]3)CCC2)cc1] | 5-chloro-2-(1-{4-[6-(difluoromethoxy)-2,4-dimethylpyridin-3-yl]phenyl}cyclobutyl)-1H-benzimidazole | Calc'd 454, found 454 |
| 49 | 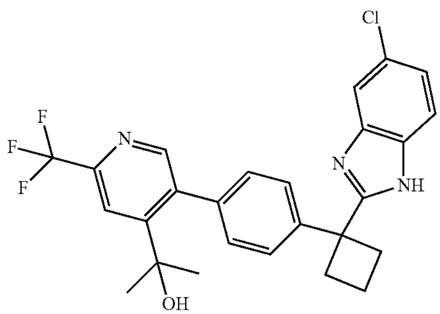 [SMILES: CC(C)(O)c1cc(C(F)(F)F)ncc1-c1ccc(C2(c3nc4cc(Cl)ccc4[nH]3)CCC2)cc1] | 2-[5-{4-[1-(5-chloro-1H-benzimidazol-2-yl)cyclobutyl]phenyl}-2-(trifluoromethyl)pyridin-4-yl]propan-2-ol | Calc'd 486, found 486 |

Intermediate I-H: 4-(((tert-butyldimethylsilyl)oxy)methyl)-5-(4,4,5,5-tetramethyl-1,3,2-dioxaborolan-2-yl)-2-(trifluoromethyl)pyridine

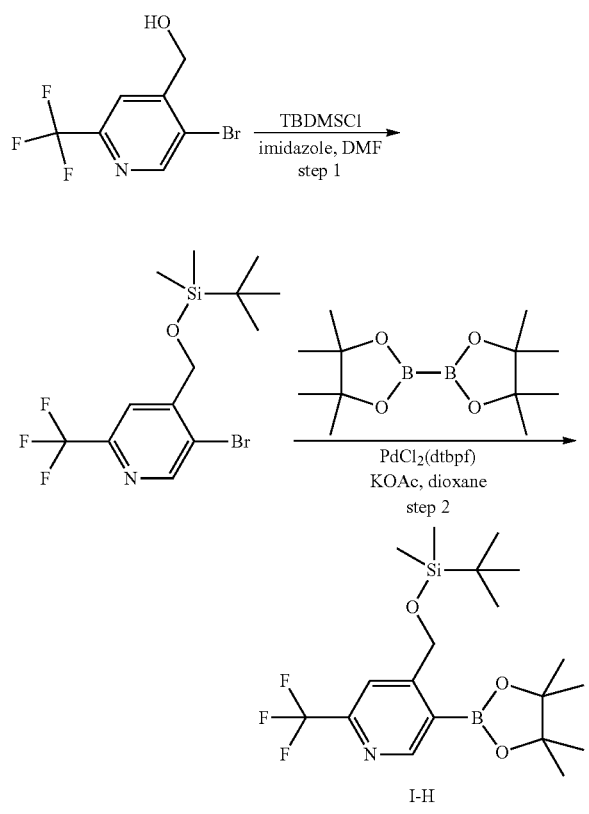

Step 1: 5-Bromo-4-(((tert-butyldimethylsilyl)oxy)methyl)-2-(trifluoromethyl)pyridine To a solution of (5-bromo-2-(trifluoromethyl)pyridin-4-yl)methanol (1.0 g, 3.9 mmol) in DMF (7.8 mL) were added imidazole (0.585 g, 8.59 mmol) and TBDMSCl (0.648 g, 4.30 mmol). The mixture was stirred at RT for 2 h. The reaction mixture was diluted with NaHCO$_3$ (sat.), and extracted with EtOAc. The combined organic layers were washed with brine, dried over MgSO$_4$, filtered and concentrated in vacuo to afford a residue, which was purified by column chromatography on silica gel (EtOAc in hexanes: 0-50% gradient) to give the title compound. MS (EI) m/z 370 [M+H]$^+$.

Step 2: 4-(((Tert-butyldimethylsilyl)oxy)methyl)-5-(4,4,5,5-tetramethyl-1,3,2-dioxaborolan-2-yl)-2-(trifluoromethyl)pyridine (I-H)

A mixture of 5-bromo-4-(((tert-butyldimethylsilyl)oxy)methyl)-2-(trifluoromethyl)pyridine (1.26 g, 3.40 mmol), bis(pinacolato)diboron (0.951 g, 3.74 mmol), PdCl$_2$(dtbpf) (0.222 g, 0.340 mmol), KOAc (0.668 g, 6.81 mmol) in 1,4-dioxane (11 mL) was evacuated and back filled with N$_2$ three times. The mixture was heated at 80° C. for 14 h. The reaction mixture was cooled to RT and filtered through a Celite® pad. The filtrate was diluted with water and extracted with EtOAc. The combined organic layers were washed with brine, dried over Na$_2$SO$_4$, filtered and concentrated in vacuo to give the title compound (I-H), which was used in next step without further purification. MS (EI) m/z 418 [M+H]$^+$.

Example 50: (5-(4-(3-(6-chloro-1H-imidazo[4,5-b]pyridin-2-yl)oxetan-3-yl)phenyl)-2-(trifluoromethyl)pyridin-4-yl)methanol (Ex. 50)

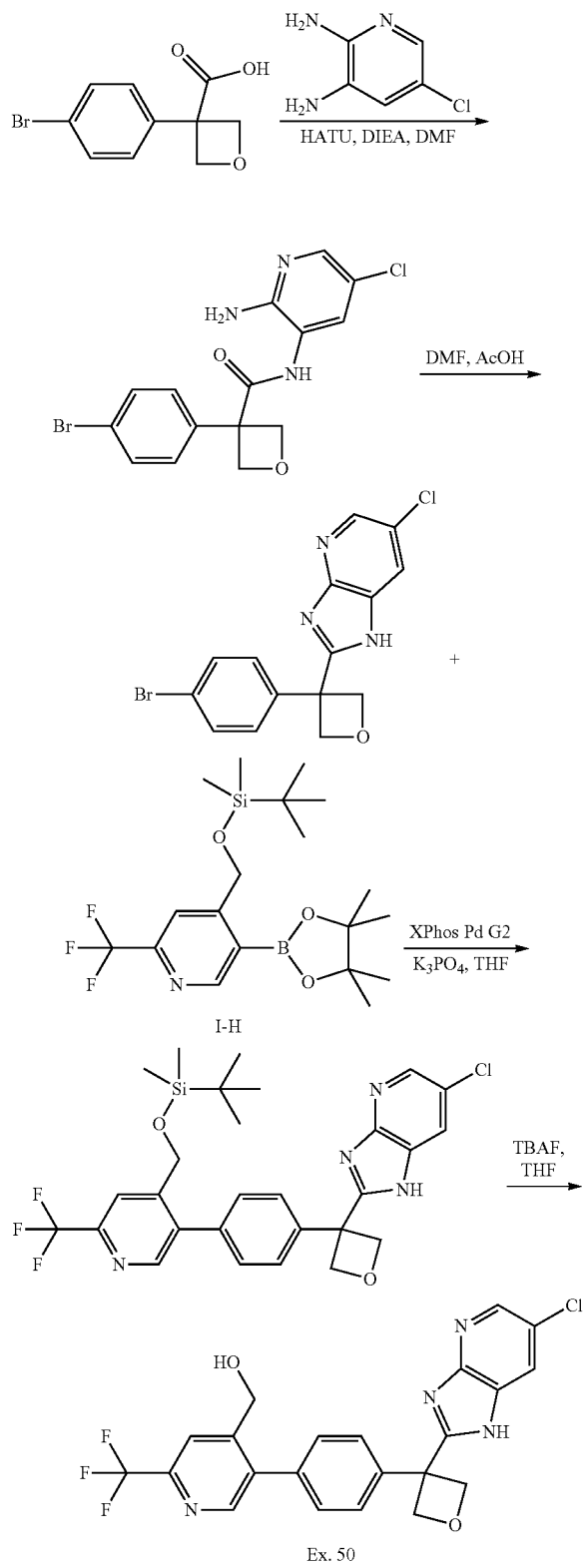

Step 1: N-(2-amino-5-chloropyridin-3-yl)-3-(4-bromophenyl)oxetane-3-carboxamide

To a vial were added 3-(4-bromophenyl)oxetane-3-carboxylic acid (200 mg, 0.778 mmol), 5-chloropyridine-2,3-diamine (134 mg, 0.934 mmol), HATU (444 mg, 1.17 mmol), DMF (5 mL) and DIEA (400 μl, 2.29 mmol). The mixture was stirred at RT for 18 h. The solvent was evaporated in vacuo. The residue was purified by column chromatography on silica gel (EtOAc in hexane: 0-70% gradient) to afford the title compound. MS (EI) m/z 382 [M+H]$^+$.

Step 2: 2-(3-(4-Bromophenyl)oxetan-3-yl)-6-chloro-1H-imidazo[4,5-b]pyridine

To a vial containing N-(2-amino-5-chloropyridin-3-yl)-3-(4-bromophenyl)oxetane-3-carboxamide (298 mg, 0.779 mmol) were added DMF (4.00 mL) and acetic acid (1 mL). The mixture was irradiated in microwave at 150° C. for 1 h. The solvent was evaporated in vacuo to afford a residue. To the residue were added EtOAc and NaHCO$_3$ (sat.), the organic phase were washed with brine, dried over Na$_2$SO$_4$, filtered and concentrated in vacuo to afford the title compound, which was used in next step directly. MS (EI) m/z 364 [M+H]$^+$.

Step 3: 2-(3-(4-(4-(((Tert-butyldimethylsilyl)oxy)methyl)-6-(trifluoromethyl)pyridin-3-yl)phenyl)oxetan-3-yl)-6-chloro-1H-imidazo[4,5-b]pyridine To a vial were added 2-(3-(4-bromophenyl)oxetan-3-yl)-6-chloro-1H-imidazo[4,5-b]pyridine (60 mg, 0.16 mmol), I-H (100 mg, 0.240 mmol), XPhos Pd G2 (chloro(2-dicyclohexylphosphino-2',4',6'-triisopropyl-1,1'-biphenyl)[2-(2'-amino-1,1'-biphenyl)]palladium(II), 13 mg, 0.016 mmol), THF (1 mL) and K$_3$PO$_4$ (1 M, 500 μl, 0.500 mmol). The mixture was evacuated and backfilled with N$_2$ for four times and heated at 60° C. for 1.5 h. The mixture was diluted with water and EtOAc. The aqueous layer was extracted with EtOAc three times. The combined organic layers were washed with brine, dried over Na$_2$SO$_4$, filtered and concentrated in vacuo to afford a residue, which was purified by column chromatography on silica gel (EtOAc in hexane: 0-60% gradient) to afford the title compound. MS (EI) m/z 575 [M+H]$^+$.

Step 4: (5-(4-(3-(6-Chloro-1H-imidazo[4,5-b]pyridin-2-yl)oxetan-3-yl)phenyl)-2-(trifluoromethyl)pyridin-4-yl)methanol (Ex. 50)

To a vial containing 2-(3-(4-(4-(((tert-butyldimethylsilyl)oxy)methyl)-6-(trifluoromethyl)pyridin-3-yl)phenyl)oxetan-3-yl)-6-chloro-1H-imidazo[4,5-b]pyridine (59.3 mg, 0.103 mmol) were added THF (300 μL) and TBAF (1 M in THF, 300 μL, 0.300 mmol). The mixture was stirred at RT for 1 h. The mixture was diluted with NaHCO$_3$ (sat.) and extracted with EtOAc. The combined organic layers were washed with brine, dried over Na$_2$SO$_4$, filtered and concentrated in vacuo to afford a residue, which was purified by reversed phase HPLC, eluting with water (0.1% TFA)-ACN to afford the title compound as a TFA salt (Ex. 50). $^1$H NMR (600 MHz, DMSO-d$_6$) δ 8.55 (s, 1H), 8.32 (s, 1H), 8.13 (s, 1H), 7.98 (s, 1H), 7.52 (s, 1H), 7.48 (s, 3H), 5.39 (d, J=6.1 Hz, 2H), 5.17 (d, J=6.2 Hz, 2H), 4.51 (s, 2H); MS (EI) m/z 461 [M+H]$^+$.

Examples 51-52

Examples 51 and 52 were prepared in an analogous fashion to Example 50 by using the corresponding acids and amines.

| Ex. # | Structure | Chemical Name | Mass [M + H]+ |
|---|---|---|---|
| 51 | 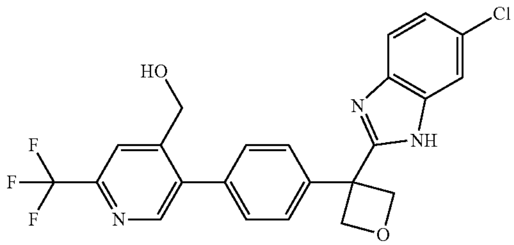 [SMILES: OCc1cc(C(F)(F)F)ncc1-c1ccc(C2(c3nc4ccc(Cl)cc4[nH]3)COC2)cc1] | [5-{4-[3-(6-chloro-1H-benzimidazol-2-yl)oxetan-3-yl]phenyl}-2-(trifluoromethyl)pyridin-4-yl]methanol | Calc'd 460, found 460 |
| 52 | 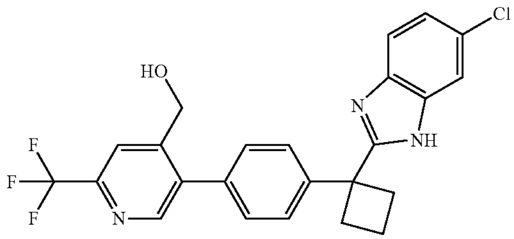 [SMILES: OCc1cc(C(F)(F)F)ncc1-c1ccc(C2(c3nc4ccc(Cl)cc4[nH]3)CCC2)cc1] | [5-{4-[1-(6-chloro-1H-benzimidazol-2-yl)cyclobutyl]phenyl}-2-(trifluoromethyl)pyridin-4-yl]methanol | Calc'd 458, found 458 |

Biological Assays
IDO1 Cellular Assay in HeLa Cells Stimulated with IFNγ

HeLa cells were cultured in complete HeLa culture medium (90% EMEM, 10% heat-inactivated fetal bovine serum) and expanded to about $1 \times 10^9$ cells. The cells were then collected and frozen down at $1 \times 10^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of $2 \times 10^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% $CO_2$ incubator. Afterwards, 12 μL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 cellular assay described above are summarized in the table below. Compounds disclosed herein generally have $IC_{50}$ of about 0.1 nM to about 5,000 nM, or more specifically, about 0.5 nM to about 2,000 nM, or more specifically, about 0.5 nM to about 1,000 nM, or more specifically, about 0.5 nM to about 500 nM, or still more specifically, about 1 nM to about 200 nM. Specific $IC_{50}$ activity data for the exemplified compounds disclosed herein is provided in the following table.

| Ex. # | IDO HeLa Cell Assay, $IC_{50}$, nM |
|---|---|
| 1 | 1.53 |
| 2 | 1.974 |
| 3 | 3.973 |
| 4 | 3.011 |
| 5 | 2.847 |
| 6 | 3.183 |
| 7 | 1.1 |
| 8 | 0.9742 |
| 9 | 1.386 |
| 10 | 3.245 |
| 11 | 1.556 |
| 12 | 1.727 |
| 13 | 7.183 |
| 14 | 140.3 |
| 15 | 15.91 |
| 16 | 1.165 |
| 17 | 1.707 |
| 18 | 0.736 |
| 19 | 0.9438 |
| 20 | 176 |
| 21 | 819.2 |
| 22 | 41.81 |

-continued

| Ex. # | IDO HeLa Cell Assay, IC$_{50}$, nM |
|---|---|
| 23 | 43.39 |
| 24 | 1.853 |
| 25 | 1.071 |
| 26 | 1.843 |
| 27 | 1.479 |
| 28 | 889.9 |
| 29 | 590.3 |
| 30 | 5.09 |
| 31 | 2.087 |
| 32 | 2.652 |
| 33 | 9.941 |
| 34 | 152 |
| 35 | 39.59 |
| 36 | 7.689 |
| 37 | 2.031 |
| 38 | 5.09 |
| 39 | 3.6 |
| 40 | |
| 41 | 7.636 |
| 42 | 2.158 |
| 43 | 2.814 |
| 44 | 2.22 |
| 45 | 15.43 |
| 46 | 2.281 |
| 47 | 3.938 |
| 48 | 2.441 |
| 49 | 1.702 |
| 50 | 3.034 |
| 51 | 1.756 |
| 52 | 1.101 |

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI medium using an Echo 555 acoustic liquid handler (Labcyte). LPS (lipopolysaccharide) and IFNγ was prepared in RPMI to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2, isotope labeled standard solutions of kunurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI medium in 1:1 ratio and proteins were precipitated out with two volumes of Acetonitrile. The plates were centrifuged at 4000×G for 60 min. 20 μL of supernatant was carefully transferred to a 384 well plate containing 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM (selected-reaction monitoring) chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and IC$_{50}$ values. Compounds were titrated and IC$_{50}$'s were calculated by 4 parameter sigmoidal curve fitting formula.

The biological activity data of selective compounds using the IDO1 human whole blood assay described above are summarized in the table below.

| Ex. # | IDO1 human whole blood assay, IC$_{50}$, nM |
|---|---|
| 1 | 74.73 |
| 3 | 75.09 |
| 5 | 191.9 |
| 7 | 40.3 |
| 8 | 133.9 |
| 9 | 52.15 |
| 10 | 132.4 |
| 11 | 22.87 |
| 16 | 35.47 |
| 17 | 117.8 |
| 18 | 103.4 |
| 19 | 43.74 |
| 24 | 119.6 |
| 25 | 47.55 |
| 26 | 182 |
| 27 | 169.5 |
| 39 | 181.9 |
| 42 | 444.6 |
| 43 | 605.8 |
| 44 | 1657 |
| 45 | 2702 |
| 46 | 237.9 |
| 47 | 190.6 |
| 48 | 130.4 |
| 49 | 72.94 |
| 50 | 4038 |
| 51 | 284.1 |
| 52 | 91.01 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

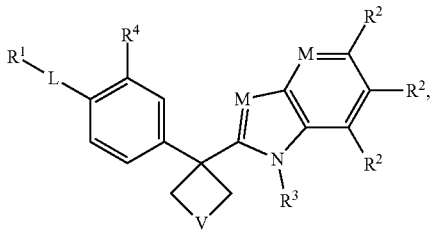

(I)

wherein:
L is selected from (1) —NHC(O)—, (2) —C(O)NH—, (3) —NH— and (4) —NHC(O)O—;
one M is —N═ and the other M is selected from (1) —CR$^a$═ and (2) —N═; wherein R$^a$ is selected from (a) H, (b) halogen and (c) C$_{1-6}$ alkyl;
V is selected from (1) —CR$^b$R$^b$—, (2) —NR$^c$— and (3) —O—; wherein each occurrence of R$^b$ is independently selected from (a) H, (b) —OH, (c) halogen and (d) C$_{1-6}$ alkyl; and R$^c$ is selected from (a) H and (b) C$_{1-6}$ alkyl;
R$^1$ is selected from (1) C$_{1-6}$ alkyl, (2) C$_{3-6}$ cycloalkyl, (3) aryl and (4) 5- or 6-membered heteroaryl;
wherein:
the C$_{1-6}$ alkyl of (1) is optionally substituted with —NH$_2$; and
each of the aryl of (3) and the heteroaryl of (4) is optionally substituted with 1 to 3 substituents independently selected from: (a) halogen, (b) —CN, (c) —NH$_2$, (d) C$_{1-6}$ alkyl optionally substituted with 1 to 3 substituents independently selected from halogen and —OH, (e) —O—C$_{1-6}$ alkyl optionally substituted with 1 to 3 halogens and (f) C$_{3-6}$ cycloalkyl;
each occurrence of R$^2$ is independently selected from (1) H, (2) —OH, (3) halogen, (4) —CN and (5) C$_{1-6}$ alkyl; wherein the C$_{1-6}$ alkyl of (5) is optionally substituted with 1 to 3 substituents independently selected from (a) —OH and (b) halogen;
R$^3$ is selected from (1) H and (2) C$_{1-6}$ alkyl optionally substituted with (a) halogen or (b) —OH; and
R$^4$ is selected from (1) H, (2) halogen, (3) —CN, (4) alkenyl and (5) C$_{1-6}$ alkyl optionally substituted with —OH.

2. The compound of claim 1, or a pharmaceutically acceptable salt thereof, wherein:
L is selected from (1) —NHC(O)— and (2) —C(O)NH—;
V is selected from (1) —CR$^b$R$^b$— and (2) —O—; wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—C$_{1-6}$ alkyl optionally substituted with 1 to 3 halogens and (g) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens;
R$^3$ is selected from (1) H and (2) C$_{1-6}$ alkyl; and
R$^4$ is selected from (1) H, (2) halogen, (3) —CN and (4) C$_{1-6}$ alkyl optionally substituted with —OH.

3. The compound of claim 1, or a pharmaceutically acceptable salt thereof, wherein:
one M is —N═ and the other M is selected from (1) —CH═ and (2) —N═;
V is selected from (1) —CR$^b$R$^b$— and (2) —O—, wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—CHF$_2$ and (g) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens;
R$^3$ is H; and
R$^4$ is selected from (1) H, (2) halogen, (3) —CN and (4) C$_{1-4}$ alkyl optionally substituted with —OH.

4. The compound of claim 1, or a pharmaceutically acceptable salt thereof, wherein:
L is selected from (1) —NHC(O)— and (2) —C(O)NH—;
V is selected from (1) —CH$_2$—, (2) —CHF—, (3) —CF$_2$— and (4) —O—;
R$^1$ is selected from (1) C$_{1-4}$ alkyl, (2) C$_{3-6}$ cycloalkyl, (3) phenyl and (4) 5- or 6-membered heteroaryl selected from isoxazolyl, oxadiazolyl, oxazolyl, oxoimidazolidinyl, pyranyl, pyrazinyl, pyrazolyl, pyridazinyl, pyridinyl, pyrimidinyl and pyrrolyl; wherein the phenyl of (3) and the heteroaryl of (4) is optionally substituted with 1 to 3 substituents independently selected from (a) halogen, (b) —CN, (c) —CF$_3$, (d) —NH$_2$, (e) C$_{1-6}$ alkyl optionally substituted with —OH, (f) —O—CHF$_2$ and (g) C$_{3-6}$ cycloalkyl; and
each occurrence of R$^2$ is independently selected from (1) H, (2) halogen, (3) —CN, (4) —CH$_3$ (5) ethyl and (6) —CF$_3$.

5. The compound of claim 1, or a pharmaceutically acceptable salt thereof, wherein:
L is selected from (1) —NHC(O)— and (2) —C(O)NH—;
V is selected from (1) —CH$_2$—, (2) —CHF—, (3) —CF$_2$— and (4) —O—;
R$^1$ is selected from (1) C$_{1-4}$ alkyl, (2) cyclopropyl, (3) phenyl and (4) 5- or 6-membered heteroaryl selected from pyrazinyl, pyrazolyl, pyridazinyl, pyridinyl and pyrimidinyl; wherein the phenyl of (3) and the heteroaryl of (4) is optionally substituted with 1 to 3 substituents independently selected from (a) halogen, (b) —CN, (c) —CF$_3$, (d) —NH$_2$, (e) —CH$_3$, (f) —CH$_2$OH, (g) —O—CHF$_2$ and (h) cyclopropyl; and
each occurrence of R$^2$ is independently selected from (1) H, (2) halogen, (3) —CN, (4) —CH$_3$ and (5) —CF$_3$, and
R$^4$ is selected from (1) H, (2) halogen, (3) —CN, (4) —CH$_3$ and (5) —CH$_2$OH.

6. The compound of claim 1, or a pharmaceutically acceptable salt thereof, of formula (Ia):

(Ia)

wherein:
L is selected from (1) —NHC(O)—, (2) —C(O)NH— and (3) —NHC(O)O—;
V is selected from (1) —CR$^b$R$^b$— and (2) —O—, wherein each occurrence of R$^b$ is independently selected from (a) H, (b) —OH and (c) halogen;
R$^1$ is selected from (1) C$_{1-6}$ alkyl, (2) C$_{3-6}$ cycloalkyl, (3) aryl and (4) 5- or 6-membered heteroaryl; wherein the aryl of (3) and the heteroaryl of (4) is optionally substituted with 1 to 3 substituents independently selected from (a) halogen, (b) —CN, (c) —NH$_2$, (d) C$_{1-6}$ alkyl optionally substituted with 1 to 3 substituents independently selected from halogen and —OH, (e) —O—C$_{1-6}$ alkyl optionally substituted with 1 to 3 halogens and (f) C$_{3-6}$ cycloalkyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^4$ is selected from (1) H, (2) halogen, (3) —CN and (4) C$_{1-4}$ alkyl optionally substituted with —OH.

7. The compound of claim 6, or a pharmaceutically acceptable salt thereof, wherein:
L is selected from (1) —NHC(O)— and (2) —C(O)NH—;
V is selected from (1) —CR$^b$R$^b$— and (2) —O—; wherein each occurrence of R$^b$ is independently selected from (a) H and (b) halogen;
R$^1$ is selected from (1) C$_{3-6}$ cycloalkyl, (2) phenyl and (3) 5- or 6-membered heteroaryl selected from isoxazolyl, oxadiazolyl, oxazolyl, oxoimidazolidinyl, pyranyl, pyrazinyl, pyrazolyl, pyridazinyl, pyridinyl, pyrimidinyl and pyrrolyl; wherein each of the phenyl of (2) and the heteroaryl of (3) is optionally substituted with 1 to 3 substituents independently selected from (a) halogen, (b) —CN, (c) —CF$_3$, (d) C$_{1-6}$ alkyl optionally substituted with —OH, (e) —O—CHF$_2$ and (f) cyclopropyl;
each occurrence of R$^2$ is independently selected from (1) H, (2) halogen, (3) —CN, (4) —CH$_3$ and (5) —CF$_3$; and
R$^4$ is selected from (1) H, (2) halogen, (3) —CN, (4) —CH$_3$ and (5) —CH$_2$OH.

8. The compound of claim 6, or a pharmaceutically acceptable salt thereof, wherein:
V is selected from (1) —CH$_2$—, (2) —CHF—, (3) —CF$_2$— and (4) —O—;
R$^1$ is selected from (1) C$_{3-6}$ cycloalkyl, (2) phenyl and (3) 5- or 6-membered heteroaryl selected from pyrazinyl, pyrazolyl, pyridazinyl, pyridinyl and pyrimidinyl; wherein the phenyl of (2) and the heteroaryl of (3) is optionally substituted with 1 to 3 substituents independently selected from (a) halogen, (b) —CN, (c) —CF$_3$, (d) —CH$_3$ (e) —CH$_2$OH, (f) —O—CHF$_2$ and (g) cyclopropyl;

each occurrence of R$^2$ is independently selected from (1) H, (2) halogen, (3) —CN and (4) —CF$_3$; and
R$^4$ is selected from (1) H, (2) halogen, (3) —CN and (4) —CH$_2$OH.

9. The compound of claim 6, or a pharmaceutically acceptable salt thereof, wherein R$^1$ is selected from (1) C$_{3-6}$ cycloalkyl, (2) phenyl and (3) 5- or 6-membered heteroaryl selected from pyrazolyl, pyridinyl and pyrimidinyl; wherein the phenyl of (2) and the heteroaryl of (3) is optionally substituted with 1 to 3 substituents independently selected from (a) halogen, (b) —CN, (c) —CF$_3$, (d) —CH$_3$, (e) —CH$_2$OH, (f) —O—CHF$_2$ and (g) cyclopropyl.

10. A compound of formula (Ib), or a pharmaceutically acceptable salt thereof:

(Ib)

wherein:
V is selected from (1) —CR$^b$R$^b$— and (2) —O—; wherein each occurrence of R$^b$ is independently selected from (a) H, (b) —OH and (c) halogen;
R$^1$ is selected from (1) C$_{3-6}$ cycloakyl, and (2) aryl; wherein the aryl of (2) is optionally substituted with 1 to 3 substituents independently selected from (a) halogen, (b) —CN, (c) C$_{1-6}$ alkyl optionally substituted with 1 to 3 substituents independently selected from halogen and —OH, (d) —O—C$_{1-6}$ alkyl optionally substituted with 1 to 3 halogens and (e) C$_{3-6}$ cycloakyl;
each occurrence of R$^2$ is independently selected from (1) H, (2) halogen, (3) —CN and (4) C$_{1-6}$ alkyl; wherein the C$_{1-6}$ alkyl is optionally substituted with 1 to 3 halogens; and
R$^4$ is selected from (1) H, (2) halogen, (3) —CN and (4) —CH$_2$OH.

11. The compound of claim 1, or a pharmaceutically acceptable salt thereof, selected from the group consisting of:
3-cyano-N-(4-(1-(6-(trifluoromethyl)-3H-imidazo[4,5-b]pyridin-2-yl)cyclobutyl)phenyl)benzamide,
3-cyano-N-(4-{1-[6-(trifluoromethyl)-1H-benzimidazol-2-yl]cyclobutyl}phenyl)benzamide,
N-{4-[1-(7-chloro-1H-benzimidazol-2-yl)cyclobutyl]phenyl}-3-cyanobenzamide,
3-cyano-N-{4-[1-(7-cyano-1H-benzimidazol-2-yl)cyclobutyl]phenyl}benzamide,
N-{4-[1-(6-chloro-1H-imidazo[4,5-b]pyridin-2-yl)cyclobutyl]phenyl}-3-cyanobenzamide,
N-(4-(3-(6-chloro-1H-benzo[d]imidazol-2-yl)oxetan-3-yl)phenyl)-3-cyanobenzamide,
3-bromo-N-(4-(1-(6-bromo-3H-imidazo[4,5-b]pyridin-2-yl)cyclobutyl)-2-chlorophenyl)benzamide,
N-(2-chloro-4-(1-(6-cyano-3H-imidazo[4,5-b]pyridin-2-yl)cyclobutyl)phenyl)-3-cyanobenzamide,
3-cyano-N-(4-(1-(6-cyano-3H-imidazo[4,5-b]pyridin-2-yl)cyclobutyl)-2-methylphenyl)benzamide,
N-(4-(1-(6-bromo-3H-imidazo[4,5-b]pyridin-2-yl)cyclobutyl)-2-fluorophenyl)-3-cyanobenzamide, 3-cyano-N-(4-(1-(6-cyano-3H-imidazo[4,5-b]pyridin-2-yl)cyclobutyl)-2-fluorophenyl)benzamide, N-{4-[1-(6-chloro-3H-imidazo[4,5-b]pyridin-2-yl)cyclobutyl]-2-fluorophenyl}-3-cyanobenzamide, 3-cyano-N-(2-fluoro-4-{1-[6-(trifluoromethyl)-3H-imidazo[4,5-b]pyridin-2-yl]cyclobutyl}phenyl)benzamide, 2-(1-(4-((1-Methyl-1H-pyrazol-3-yl)amino)-3-vinylphenyl)cyclobutyl)-3H-imidazo[4,5-b]pyridine-6-carbonitrile, 2-(1-(3-(Hydroxymethyl)-4-((1-methyl-1H-pyrazol-3-yl)amino)phenyl)cyclobutyl)-3H-imidazo[4,5-b]pyridine-6-carbonitrile, cyclopropyl (4-(1-(6-cyano-3H-imidazo[4,5-b]pyridin-2-yl)cyclobutyl)phenyl)carbamate, N-(4-(1-(6-chloro-1H-benzo[d]imidazol-2-yl)-3-hydroxycyclobutyl)phenyl)-3-cyanobenzamide, 3-chloro-N-(4-(1-(6-chloro-1H-imidazo[4,5-b]pyridin-2-yl)-3,3-difluorocyclobutyl)phenyl)benzamide, N-(4-(1-(6-chloro-1H-benzo[d]imidazol-2-yl)-3-fluorocyclobutyl)phenyl)-3-cyanobenzamide, 3-cyano-N-(4-(1-(6-cyano-1H-benzo[d]imidazol-2-yl)-3-fluorocyclobutyl)phenyl)benzamide, N-(3-chlorophenyl)-4-(1-(6-(trifluoromethyl)-1H-imidazo[4,5-b]pyridin-2-yl)cyclobutyl)benzamide, 4-(1-(6-cyano-1H-imidazo[4,5-b]pyridin-2-yl)-3,3-difluorocyclobutyl)-N-cyclohexylbenzamide, 4-(1-(6-cyano-1H-imidazo[4,5-b]pyridin-2-yl)-3,3-difluorocyclobutyl)-N-(6-methylpyridin-2-yl)benzamide, N-(3-cyanophenyl)-4-{1-[6-(trifluoromethyl)-1H-imidazo[4,5-b]pyridin-2-yl]cyclobutyl}benzamide, N-(3-fluorophenyl)-4-{1-[6-(trifluoromethyl)-1H-imidazo[4,5-b]pyridin-2-yl]cyclobutyl}benzamidem N-(2,4-difluorophenyl)-4-{1-[6-(trifluoromethyl)-1H-imidazo[4,5-b]pyridin-2-yl]cyclobutyl}benzamide, N-(5-chloropyridin-3-yl)-4-{1-[6-(trifluoromethyl)-1H-imidazo[4,5-b]pyridin-2-yl]cyclobutyl}benzamide, N-cyclohexyl-4-{1-[6-(trifluoromethyl)-1H-imidazo[4,5-b]pyridin-2-yl]cyclobutyl}benzamide, N-(2-methylpropyl)-4-{1-[6-(trifluoromethyl)-1H-imidazo[4,5-b]pyridin-2-yl]cyclobutyl}benzamide, N-(5-cyano-2-fluorophenyl)-4-{1-[6-(trifluoromethyl)-1H-imidazo[4,5-b]pyridin-2-yl]cyclobutyl}benzamide, N-(5-chloro-2-fluorophenyl)-4-{1-[6-(trifluoromethyl)-1H-imidazo[4,5-b]pyridin-2-yl]cyclobutyl}benzamide, and 4-[1-(6-cyano-1H-imidazo[4,5-b]pyridin-2-yl)-3,3-difluorocyclobutyl]-N-(3-cyanophenyl)benzamide.

12. A composition which comprises an inert carrier and a compound of claim 1 or a pharmaceutically acceptable salt thereof.

13. A method for treating an IDO-associated disease or disorder in a mammalian subject which comprises administering to the subject an effective amount of a compound of claim 1 or a pharmaceutically acceptable salt thereof.

14. A method for treating an IDO-associated disease or disorder in a mammalian subject which comprises administering to the subject an effective amount of a compound of claim 1 or a pharmaceutically acceptable salt thereof in combination with another anti-cancer agent.

15. The method of claim 14, wherein the IDO-associated disease or disorder is a cancer, viral infection, HCV infection, depression, neurodegenerative disorders, trauma, age-related cataracts, organ transplantation, and autoimmune diseases.

16. The method of claim 15, wherein the cancer is a cancer of the colon, pancreas, breast, prostate, lung, brain, ovary, cervix, testes, renal, head and neck, lymphoma, leukemia, and melanoma.

\* \* \* \* \*